(12) United States Patent
Wohlgemuth et al.

(10) Patent No.: US 7,645,575 B2
(45) Date of Patent: Jan. 12, 2010

(54) GENES USEFUL FOR DIAGNOSING AND MONITORING INFLAMMATION RELATED DISORDERS

(75) Inventors: Jay Wohlgemuth, Menlo Park, CA (US); Darren Tayama, San Francisco, CA (US); Dirk Walther, Rosenfelder Ring (DE); Preeti G. Lal, Santa Clara, CA (US)

(73) Assignee: XDX, Inc., Brisbane, CA (US)

( * ) Notice: Subject to any disclaimer, the term of this patent is extended or adjusted under 35 U.S.C. 154(b) by 0 days.

(21) Appl. No.: 11/223,492

(22) Filed: Sep. 8, 2005

(65) Prior Publication Data

US 2006/0051803 A1 Mar. 9, 2006

Related U.S. Application Data

(60) Provisional application No. 60/608,403, filed on Sep. 8, 2004.

(51) Int. Cl.
*C12Q 1/66* (2006.01)
*C12P 19/34* (2006.01)
*C07H 21/04* (2006.01)

(52) U.S. Cl. .................. 435/6; 435/91.2; 536/23.5; 536/24.31

(58) Field of Classification Search .................... None
See application file for complete search history.

(56) References Cited

U.S. PATENT DOCUMENTS

| | | | |
|---|---|---|---|
| 4,190,535 A | 2/1980 | Luderer |
| 4,215,051 A | 7/1980 | Palmer |
| 4,350,593 A | 9/1982 | Kessler |
| 4,358,535 A | 11/1982 | Falkow et al. |
| 4,376,110 A | 3/1983 | David |
| 4,582,789 A | 4/1986 | Sheldon, III et al. |
| 4,683,195 A | 7/1987 | Mullis et al. |
| 4,683,202 A | 7/1987 | Mullis et al. |
| 4,751,001 A | 6/1988 | Saunders |
| 4,762,780 A | 8/1988 | Spector et al. |
| 4,789,630 A | 12/1988 | Bloch et al. |
| 4,800,159 A | 1/1989 | Mullis et al. |
| 4,818,418 A | 4/1989 | Saunders |
| 4,843,155 A | 6/1989 | Chomczynski |
| 4,889,818 A | 12/1989 | Gelfand et al. |
| 4,908,318 A | 3/1990 | Lerner |
| 4,946,778 A | 8/1990 | Ladner |
| 4,946,952 A | 8/1990 | Kiefer |
| 4,965,188 A | 10/1990 | Mullis et al. |
| 5,053,134 A | 10/1991 | Luderer |
| 5,063,162 A | 11/1991 | Kiefer |
| 5,066,584 A | 11/1991 | Gyllensten et al. |
| 5,075,216 A | 12/1991 | Innis et al. |
| 5,079,352 A | 1/1992 | Gelfand et al. |
| 5,091,310 A | 2/1992 | Innis |
| 5,120,525 A | 6/1992 | Goldenberg |
| 5,142,033 A | 8/1992 | Innis |
| 5,143,854 A | 9/1992 | Pirrung et al. |
| 5,210,015 A | 5/1993 | Gelfand et al. |
| 5,212,071 A | 5/1993 | Fearon et al. |
| 5,215,882 A | 6/1993 | Bahl et al. |
| 5,219,727 A | 6/1993 | Wang et al. |
| 5,264,351 A | 11/1993 | Harley |
| 5,278,043 A | 1/1994 | Bannwarth et al. |
| 5,310,652 A | 5/1994 | Gelfand et al. |
| 5,314,809 A | 5/1994 | Erlich et al. |
| 5,322,770 A | 6/1994 | Gelfand |
| 5,340,720 A | 8/1994 | Stetler |
| 5,346,994 A | 9/1994 | Chomczynski |
| 5,352,600 A | 10/1994 | Gelfand et al. |
| 5,374,553 A | 12/1994 | Gelfand et al. |
| 5,385,824 A | 1/1995 | Hoet et al. |
| 5,389,512 A | 2/1995 | Sninsky et al. |
| 5,393,672 A | 2/1995 | Van Ness et al. |
| 5,405,774 A | 4/1995 | Abramson et al. |
| 5,407,800 A | 4/1995 | Gelfand et al. |
| 5,411,876 A | 5/1995 | Bloch et al. |
| 5,418,149 A | 5/1995 | Gelfand et al. |
| 5,420,029 A | 5/1995 | Gelfand et al. |
| 5,426,039 A | 6/1995 | Wallace et al. |
| 5,445,940 A | 8/1995 | Brenner et al. |
| 5,455,170 A | 10/1995 | Abramson et al. |
| 5,459,037 A | 10/1995 | Sutcliffe et al. |
| 5,466,591 A | 11/1995 | Abramson et al. |
| 5,468,613 A | 11/1995 | Erlich et al. |
| 5,476,774 A | 12/1995 | Wang et al. |
| 5,487,970 A | 1/1996 | Rowley et al. |
| 5,487,972 A | 1/1996 | Gelfand et al. |
| 5,491,063 A | 2/1996 | Fisher et al. |
| 5,491,086 A | 2/1996 | Gelfand et al. |

(Continued)

FOREIGN PATENT DOCUMENTS

EP 0217992 A2 4/1987

(Continued)

OTHER PUBLICATIONS

Chen et al. Identification of differentially expressed genes in rat aortic allograft vasculopathy. 1996. American Journal of PAthology. vol. 149 pp. 597-611.*

(Continued)

*Primary Examiner*—Carla Myers
*Assistant Examiner*—Amanda Shaw
(74) *Attorney, Agent, or Firm*—Morrison & Foerster LLP

(57) ABSTRACT

Described herein is a system for monitoring gene expression for diagnosing and monitoring inflammation disorders, and for monitoring gene expression in inflammation disorders in response to a particular drug treatment regimen. This system for detecting nucleic acid expression in a body fluid uses an isolated polynucleotide to detect expression of a nucleic acid comprising a nucleotide sequence selected from the group consisting of SEQ ID NO: 5; SEQ ID NO:11; SEQ ID NO:17; and SEQ ID NO: 23. These nucleic acids are differentially expressed in body fluid in an individual with a disease criterion for a disease as listed in Table 1 as compared to an individual without the disease criterion.

6 Claims, 4 Drawing Sheets

U.S. PATENT DOCUMENTS

| | | |
|---|---|---|
| 5,501,963 A | 3/1996 | Burckhardt et al. |
| 5,506,145 A | 4/1996 | Bull et al. |
| 5,512,462 A | 4/1996 | Cheng |
| 5,514,556 A | 5/1996 | Shearer et al. |
| 5,538,848 A | 7/1996 | Livak et al. |
| 5,561,058 A | 10/1996 | Gelfand et al. |
| 5,565,339 A | 10/1996 | Bloch et al. |
| 5,569,583 A | 10/1996 | Greenberg et al. |
| 5,571,673 A | 11/1996 | Picone |
| 5,573,906 A | 11/1996 | Bannwarth et al. |
| 5,604,099 A | 2/1997 | Erlich et al. |
| 5,618,703 A | 4/1997 | Gelfand et al. |
| 5,618,711 A | 4/1997 | Gelfand et al. |
| 5,624,833 A | 4/1997 | Gelfand et al. |
| 5,635,365 A | 6/1997 | Ansari et al. |
| 5,641,864 A | 6/1997 | Gelfand |
| 5,658,744 A | 8/1997 | Ochoa et al. |
| 5,665,551 A | 9/1997 | Gelfand et al. |
| 5,674,738 A | 10/1997 | Abramson et al. |
| 5,677,152 A | 10/1997 | Birch et al. |
| 5,693,517 A | 12/1997 | Gelfand et al. |
| 5,707,807 A | 1/1998 | Kato |
| 5,716,787 A | 2/1998 | Dunn et al. |
| 5,721,351 A | 2/1998 | Levinson |
| 5,728,822 A | 3/1998 | Macfarlane |
| 5,766,585 A | 6/1998 | Evans et al. |
| 5,773,258 A | 6/1998 | Birch et al. |
| 5,789,224 A | 8/1998 | Gelfand et al. |
| 5,795,762 A | 8/1998 | Abramson et al. |
| 5,804,375 A | 9/1998 | Gelfand et al. |
| 5,807,522 A | 9/1998 | Brown et al. |
| 5,811,284 A | 9/1998 | Chang et al. |
| 5,837,832 A | 11/1998 | Chee et al. |
| 5,939,270 A | 8/1999 | Haunso et al. |
| 5,939,292 A | 8/1999 | Gelfand et al. |
| 5,958,342 A | 9/1999 | Gamble et al. |
| 5,958,688 A | 9/1999 | Eberwine et al. |
| 5,965,366 A | 10/1999 | Ochoa et al. |
| 5,968,799 A | 10/1999 | Gelfand et al. |
| 5,973,137 A | 10/1999 | Covington |
| 5,981,481 A | 11/1999 | Fearon et al. |
| 5,994,056 A | 11/1999 | Higuchi |
| 5,994,076 A | 11/1999 | Chenchik et al. |
| 6,001,611 A | 12/1999 | Will |
| 6,004,755 A | 12/1999 | Wang |
| 6,010,853 A | 1/2000 | Kanteti et al. |
| 6,020,186 A | 2/2000 | Henco |
| 6,033,860 A | 3/2000 | Lockhart |
| 6,040,138 A | 3/2000 | Lockhart et al. |
| 6,040,166 A | 3/2000 | Erlich et al. |
| 6,045,996 A | 4/2000 | Cronin et al. |
| 6,048,695 A | 4/2000 | Bradley et al. |
| 6,048,709 A | 4/2000 | Falb |
| 6,060,240 A | 5/2000 | Kamb et al. |
| 6,066,322 A | 5/2000 | Levinson |
| 6,066,498 A | 5/2000 | Levinson |
| 6,084,083 A | 7/2000 | Levinson |
| 6,087,112 A | 7/2000 | Dale |
| 6,087,477 A | 7/2000 | Falb |
| 6,090,556 A | 7/2000 | Kato et al. |
| 6,099,823 A | 8/2000 | Falb |
| 6,124,433 A | 9/2000 | Falb et al. |
| 6,127,155 A | 10/2000 | Gelfand et al. |
| 6,132,997 A | 10/2000 | Shannon |
| 6,146,828 A | 11/2000 | Lapidus et al. |
| 6,150,121 A | 11/2000 | Hamawy et al. |
| 6,156,887 A | 12/2000 | Levinson |
| 6,162,604 A | 12/2000 | Jacob |
| 6,168,933 B1 | 1/2001 | Kaser et al. |
| 6,171,785 B1 | 1/2001 | Higuchi |
| 6,177,254 B1 | 1/2001 | Rattner et al. |
| 6,187,534 B1 | 2/2001 | Strom et al. |
| 6,190,857 B1 | 2/2001 | Ralph et al. |
| 6,190,872 B1 | 2/2001 | Slotman |
| 6,194,158 B1 | 2/2001 | Kroes et al. |
| 6,197,563 B1 | 3/2001 | Erlich et al. |
| 6,203,987 B1 | 3/2001 | Friend et al. |
| 6,204,371 B1 | 3/2001 | Levinson |
| 6,214,979 B1 | 4/2001 | Gelfand et al. |
| 6,218,122 B1 | 4/2001 | Friend et al. |
| 6,222,093 B1 | 4/2001 | Marton et al. |
| 6,225,084 B1 | 5/2001 | Falb et al. |
| 6,225,093 B1 | 5/2001 | Grant et al. |
| 6,228,628 B1 | 5/2001 | Gelfand et al. |
| 6,242,185 B1 | 6/2001 | Kaser et al. |
| 6,245,334 B1 | 6/2001 | Seilhammer et al. |
| 6,245,526 B1 | 6/2001 | Yue et al. |
| 6,245,527 B1 | 6/2001 | Busfield et al. |
| 6,248,527 B1 | 6/2001 | Chen et al. |
| 6,248,528 B1 | 6/2001 | Chen et al. |
| 6,251,597 B1 | 6/2001 | Shyjan |
| 6,262,244 B1 | 7/2001 | Houchins et al. |
| 6,274,312 B1 | 8/2001 | Gish et al. |
| 6,280,941 B1 | 8/2001 | Tsao et al. |
| 6,303,321 B1 | 10/2001 | Tracey et al. |
| 6,306,602 B1 | 10/2001 | Sillekens et al. |
| 6,365,352 B1 | 4/2002 | Yerramilli et al. |
| 6,403,304 B1 | 6/2002 | Stashenko et al. |
| 6,410,319 B1 | 6/2002 | Raubitschek et al. |
| 6,797,263 B2 | 9/2004 | Strom et al. |
| 6,811,973 B1 | 11/2004 | Reich |
| 6,900,015 B2 | 5/2005 | Avihingsanon et al. |
| 6,905,827 B2 | 6/2005 | Wohlgemuth |
| 6,964,850 B2 | 11/2005 | Bevilacqua et al. |
| 7,026,121 B1 | 4/2006 | Wohlgemuth |
| 7,118,865 B2 | 10/2006 | Behrens et al. |
| 2001/0021700 A1 | 9/2001 | Moore et al. |
| 2002/0042386 A1 | 4/2002 | Rosen et al. |
| 2003/0139466 A1 | 7/2003 | Peritt et al. |
| 2004/0072181 A1 | 4/2004 | Whitehead et al. |
| 2005/0281815 A1 | 12/2005 | Eshel et al. |
| 2006/0088836 A1 | 4/2006 | Wohlgemuth |
| 2006/0216707 A1 | 9/2006 | Stuhlmuller et al. |
| 2006/0263813 A1 | 11/2006 | Rosenberg et al. |
| 2007/0037166 A1 | 2/2007 | Wohlgemuth et al. |
| 2007/0037167 A1 | 2/2007 | Wohlgemuth et al. |
| 2007/0248978 A1 | 10/2007 | Lal et al. |
| 2008/0038746 A1 | 2/2008 | Rosenberg et al. |

FOREIGN PATENT DOCUMENTS

| | | |
|---|---|---|
| EP | 0217102 B1 | 1/1992 |
| EP | 1077254 A2 | 2/2001 |
| EP | 1162276 A2 | 12/2001 |
| WO | WO-91/18626 A1 | 12/1991 |
| WO | WO-94/23023 A1 | 10/1994 |
| WO | WO-95/17506 A1 | 6/1995 |
| WO | WO-96/39536 A1 | 12/1996 |
| WO | WO-97/16568 A1 | 5/1997 |
| WO | WO-97/30065 A1 | 8/1997 |
| WO | WO-98/24935 A1 | 6/1998 |
| WO | WO-99/04251 A1 | 1/1999 |
| WO | WO-99/10536 A1 | 3/1999 |
| WO | WO-99/11782 A1 | 3/1999 |
| WO | WO-99/11822 A1 | 3/1999 |
| WO | WO-99/15700 A1 | 4/1999 |
| WO | WO-99/52541 A2 | 10/1999 |
| WO | WO-99/57130 A1 | 11/1999 |
| WO | WO-00/04191 A1 | 1/2000 |
| WO | WO-00/12753 A1 | 3/2000 |
| WO | WO-0023573 A2 | 4/2000 |
| WO | WO-00/46372 A2 | 8/2000 |
| WO | WO-00/52209 A1 | 9/2000 |
| WO | WO-00/55375 A1 | 9/2000 |

| | | | |
|---|---|---|---|
| WO | WO-00/58473 A2 | 10/2000 |
| WO | WO-00/63372 A1 | 10/2000 |
| WO | WO-00/73498 A1 | 12/2000 |
| WO | WO-00/78808 A1 | 12/2000 |
| WO | WO-01/20004 A2 | 3/2001 |
| WO | WO-01/23426 A2 | 4/2001 |
| WO | WO-01/23564 A1 | 4/2001 |
| WO | WO-01/25473 A1 | 4/2001 |
| WO | WO-01/29269 A2 | 4/2001 |
| WO | WO-01/32927 A2 | 5/2001 |
| WO | WO-01/40302 A2 | 6/2001 |
| WO | WO-01/47944 A2 | 7/2001 |
| WO | WO-01/54733 A1 | 8/2001 |
| WO | WO-01/55164 A1 | 8/2001 |
| WO | WO-01/55201 A1 | 8/2001 |
| WO | WO-01/55203 A1 | 8/2001 |
| WO | WO-01/55205 A1 | 8/2001 |
| WO | WO-01/55328 A2 | 8/2001 |
| WO | WO-01/55368 A1 | 8/2001 |
| WO | WO-01/57182 A2 | 8/2001 |
| WO | WO-01/60860 A2 | 8/2001 |
| WO | WO-01/71005 A2 | 9/2001 |
| WO | WO-01/81916 A2 | 11/2001 |
| WO | WO-01/86003 A2 | 11/2001 |
| WO | WO-02/00677 A1 | 1/2002 |
| WO | WO-02/00928 A2 | 1/2002 |
| WO | WO-02/28999 A2 | 4/2002 |
| WO | WO-02/057414 A2 | 7/2002 |
| WO | WO-03/090694 A2 | 11/2003 |
| WO | WO-2004/042346 A2 | 5/2004 |
| WO | WO-2004/108899 A2 | 12/2004 |

OTHER PUBLICATIONS

Cheung, Vivian et al. Natural variation in human gene expression assessed in lymphoblastoid cells. 2003 Nature Genetics vol. 33 pp. 422-425.*
Wu, Thomas. Analyzing gene expression data from DNA microarrays to identify candidate genes. 2001. Journal of Pathology. vol. 195 pp. 53-65.*
Newton, Ma et al. On differential variability of expression ratios: improving statistical inference about gene expression changes from microarray data. Journal of Computational Biology 2001. vol. 8, No. 1 pp. 37-52.*
U.S. Appl. No. 10/006,290, filed Oct. 22, 2001, Wohlgemuth.
U.S. Appl. No. 10/325,899, filed Dec. 20, 2002, Wohlgemuth.
U.S. Appl. No. 10/512,028, filed Apr. 14, 2003, Wohlgemuth et al.
Amaro et al. (1995). "Plasma Leukocyte Elastase Concentration in Angiographically Diagnosed Coronary Artery Disease," Eur Heart J 16(5): 615-622.
Aukrust et al. (1999). "Enhanced Levels of Soluble and Membrane-Bound CD40 Ligand in Patients with Unstable Angina. Possible Reflection of T Lymphocyte and Platelet Involvement in the Pathogenesis of Acute Coronary Syndromes," Circulation 100(6): 614-620.
Belch et al. (1997). "The White Blood Cell Adhesion Molecule E-selectin Predicts Restenosis in Patients With Intermittent Claudication Undergoing Percutaneous Transluminal Angioplasty," Circulation 95(8): 2027-2031.
Jude et al. (1994). "Evidence for Time-Dependent Activation of Monocytes in the Systemic Circulation in Unstable Angina but not in Acute Myocardial Infarction or in Stable Angina," Circulation 90(4): 1662-1668.
Kassirer et al. (1999). "Increased Expression of the CD11b/CD18 Antigen on the Surface of Peripheral White Blood Cells in Patients with Ischemic Heart Disease: Further Evidence for Smoldering Inflammation in Patients with Atherosclerosis," Am Heart J 138: 555-559.
Ross et al. (1999). "Reduced Neutrophil Infiltration Protects Against Lung Reperfusion Injury After Transplantation," Ann Thorac Surg 67(5): 1428-1433.
Smith-Norowitz et al. (1999). "Lymphocyte Activation in Angina Pectoris," Clinical Immunology 93(2): 168-175.

Tibshirani et al. (2002) Diagnosis of multiple cancer types by shrunken centroids of gene expression. PNAS 99:6567-6572.
Tusher, V.G. et al. Significance analysis of microarrays applied to the ionizing radiation response. PNAS 98:5116-5121.
U.S. Appl. No. 60/241,994, filed Oct. 20, 2000, Wohlgemuth et al.
U.S. Appl. No. 60/296,764, filed Jun. 8, 2001, Wohlgemuth et al.
U.S. Appl. No. 60/608,403, filed Sep. 8, 2004, Wohlgemuth et al.
Alizadeh, A. A. et al. (2000). "Genomic-Scale Gene Expression Profiling of Normal and Malignant Immune Cells," *Current Opinion in Immunology* 12:219-225.
Alizadeh, A. et al. (1998). "Probing Lymphocyte Biology by Genomic-Scale Gene Expression Analysis," *Journal of Clinical Immunology* 18(6): 373-379.
Glynne, R. et al. (2000). "B-Lymphocyte Quiescence, Tolerance and Activation as Viewed by Global Gene Expression Profiling on Microarrays," *Immunological Reviews* 176:216-246.
Glynne, R. J. et al. (2000). "Genomic-Scale Gene Expression Analysis of Lymphocyte Growth, Tolerance and Malignancy," *Current Opinion in Immunology* 12:210-214.
Marrack, P. et al. (2000). "Genomic-Scale Analysis of Gene Expression in Resting and Activated T Cells," *Current Opinion in Immunology* 12:208-209.
Supplemental Partial European Search Report mailed Jul. 9, 2007, for EP Application No. 01997055.7 filed Oct. 22, 2001, 6 pages.
Ahern, H. (Jul. 24, 1595), "Biochemical, Reagent Kits Offer Scientists Good Return on Investment," *The Scientist* 9(15):20-24.
Dietz, A. B. et al. (2000). "Maturation of Human Monocyte-Derived Dendritic Cells Studies by Microarray Hybridation," *Biochemical and Biophysical Research Communications* 275:731-738.
Dugré, F. J. (Oct. 15, 2000) "Cytokine and Cytotoxic Molecule Gene Expression Determined in Peripheral Blood Mononuclear Cells in the Diagnosis of Acute Renal Rejection," *Transplantation* 70(7):1074-1080.
EMBL-EBI Accession No. AA053887, last updated Aug. 31, 2006, located at <http://www.ebi.ac.uk/cgi-bin/dbfetch?db=embl&id=AA053887&style=raw> visited on Oct. 31, 2007. (3 pages).
EMBL-EBI Accession No. AAC77576, located at <http://www.ebi.ac.uk/cgi-bin/dbfetch?db=emblcds&id=AAC77576&style=raw> visited on Oct. 31, 2007. (1 page).
EMBL-EBI Accession No. AAK80490, located at <http://www.ebi.ac.uk/cgi-bin/dbfetch?db=emblcds&id=AAK80490&style> visited on Oct. 31, 2007. (1 page).
EMBL-EBI Accession No. AI775145, last updated Jun. 21, 2002, located at <http://www.ebi.ac.uk/cgi-bin/dbfetch?db=embl&id=AI755145&style=raw> visited on Oct. 31, 2007. (2 pages).
EMBL-EBI Accession No. AK000354, last updated Sep. 12, 2006, located at <http://www.ebi.ac.uk/cgi-bin/dbfetch?db=embl&id=AK000354&style=raw> visited on Oct. 31, 2007. (3 pages).
EMBL-EBI Accession No. AV742425, last updated Oct. 10, 2000, located at <http://www.ebi.ac.uk/cgi-bin/dbfetch?db=embl&id=AV742425&style=raw> visited on Oct. 31, 2007. (2 pages).
EMBL-EBI Accession No. AW969353, last updated Jun. 8, 2000, located at <http://www.ebi.ac.uk/cgi-bin/dbfetch?db=embl&id=AW969353&style=raw> visited on Oct. 31, 2007. (1 page).
EMBL-EBI Accession No. G06338, last updated Mar. 4. 2000, located at <http://www.ebi.ac.uk/cgi-bin/dbfetch?db=embl&id=G06338&style=raw> visited on Oct. 31, 2007. (2 pages).
EMBL-EBI Accession No. L26474, last updated Jan. 9, 2007, located at <http://www.ebi.ac.uk/cgi-bin/dbfetch?db=embl&id=L26474&style=raw> visited on Oct. 31, 2007. (6 pages).
EMBL-EBI Accession No. M23068, last updated Nov. 14, 2006, located at <http://www.ebi.ac.uk/cgi-bin/dbfetch?db=embl&id=M23068&style=raw> visited on Oct. 31, 2007. (2 pages).
EMBL-EBI Accession No. V00497, last updated Nov. 20, 2004, located at <http://www.ebi.ac.uk/cgi-bin/dbfetch?db=embl&id=V00497&style=raw> visited on Oct. 31, 2007. (5 pages).
Finger, L. R. et al. (1997). "The Human PD-1 Gene: Complete cDNA, Genomic Organization, and Developmentally Regulated Expression in B cell Progenitors," *Gene* 197:177-187.
Fullerton, S. M. et al. (Mar. 1994). "Molecular and Population Genetic Analysis of Allelic Sequence Diversity at the Human Beta-Globin Locus," *Proceedings of the National Academy of Sciences* 91:1805-1809.

GenBank Accession No. Y10376, last updated May 14, 1997, located at <http://www.ncbi.nlm.nih.gov/entrez/viewer.fcgi?db=nuccore&id=2052057> visited on Apr. 8, 2008, 3 pages.

Gorcynski, R. M. (1996). "Correlation of Peripheral Blood Lymphocyte and Intragraft Cytokine mRNA Expression with Rejection in Orthotopic Liver Transplantation," *Surgery* 120(3):496-502.

Griffiths, G. M. et al. (1991). "Granzyme A and Perforin as Markers for Rejection in Cardiac Transplantation," *European Journal of Immunology* 21:687-692.

International Search Report and Written Opinion mailed Mar. 27, 2008, for PCT Application No. PCT/US05//31806 filed Sep. 8, 2005, 14 pages.

Jardi, M. et al. (1994). "Urokinase Receptor (UPAR) Expression During Hematopoietic Maturation," *Journal of Drug Targeting* 8(Suppl 1):51.

Joulin, V. et al. (Oct. 25, 1988). "Isolation and Characterization of the Human 2,3-Bisphosphoglycerate Mutase Gene," *The Journal of Biological Chemistry* 263(30):15785-15790.

Krause, S. W. (1998), "Carboxypeptidase M as a Marker of Macrophage Maturation," *Immunological Reviews* 161:119-127.

Le Naour, F. et al. (May 25, 2001). "Profiling Changes in Gene Expression during Differentiation and Maturation of Monocyte-Derived Dendritic Cells Using Both Oligonucleotide Microarrays and Proteomics," *The Journal of Biological Chemistry* 276(21):17920-17931.

Supplementary European Search Report mailed Oct. 18, 2007, for EP Application No. 03799755.8 filed Apr. 24, 2003, 17 pages.

Tamayo, P. et al. (Mar. 1999). "Interpreting Patterns of Gene Expression with Self-Organizing Maps: Methods and Application to Hematopoietic Differentiation," *Proceedings of the National Academy of Sciences* 96:2907-2912.

Vasconcellos, L. M. et al. (Sep. 15, 1998). "Cytotoxic Lymphocyte Gene Expression in Peripheral Blood Leukocytes Correlates with Rejecting Renal Allografts," *Transplantation* 66(5):562-566.

Willems, R. et al. (May 29, 1998). "Decrease in Nucleoside Diphosphate Kinase (NDPK/nm23) Expression During Hematopoietic Maturation," *The Journal of Biological Chemistry* 273(22):13663-13668.

Doi, S. et al. (1994). "Polymerase Chain Reaction Quantification of Cytokine Messenger RNA Expression in Peripheral Blood Monoculear Cells of Patients with Acute Exacerbations of Asthma: Effect of Glucocorticoid Therapy," *Clinical and Experimental Allergy* 24:854-867.

Dudek, A. Z. et al. (Jun. 2003), "Platelet Factor 4 Promotes Adhesion of Hematopoietic Progenitor Cells and Binds IL-8: Novel Mechanisms for Modulation of Hematopoiesis," *Blood* 101(12):4687-4694.

Edman, C. F. et al. (1997). "Electric Field Directed Nucleic Acid Hybridization on Microchips," *Nucleic Acids Research* 25(24):4907-4914.

Eisen, M. B. et al. (Dec. 1998). "Cluster Analysis and Display of Genome-Wide Expression Patterns," *Proceedings of the National Academy of Sciences* 95: 14863-14868.

Fandrey, J. et al. (Feb. 1, 1993). "In Vivo and In Vitro Regulation of Erythropoietin mRNA: Measurement by Competitive Polymerase Chain Reaction," *Blood* 81(3):617-623.

Felson, D. T. et al. (Jun. 1995). "American College of Rheumatology. Preliminary Definition of Improvement in Rheumatoid Arthritis," *Arthritis and Rheumatism* 38(6):727-735.

Fu, G. et al. (2002). "Representational Difference Analysis in a Lupus-Prone Mouse Strain Results in the Identification of an Unstable Region of the Genome on Chromosome 11," *Nucleic Acids Research* 30(6):1394-1400.

Gabay, C. et al. (1997). "Circulating Levels of Tumor Necrosis Factor Soluble Receptors in Systemic Lupus Erythematosus are Significantly Higher than in Other Rheumatic Diseases and Correlate with Disease Activity," *The Journal of Rheumatology* 24(2):303-308.

GenBank Accession No. AL591031, located at <http://www.ncbi.nlm.nih.gov/entrez/viewer.fcgi?db=nuccore&id=16073692> visited on Jun. 27, 2007. (41 pages).

Ghosh, A. et al. (Jul. 2001), "A Specific Isozyme of 2'-5' Oligoadenylate Synthetase is a Dual Function Proapoptotic Protein of the Bcl-2 Family," *The Journal of Biological Chemistry* 276(27):25477-25455.

Golder-Mason, L. et al. (2000). "Differential Expression of Lymphoid and Myeloid Markers on Differentiating Hematopoietic Stem Cells in Normal and Tumor-Bearing Adult Human Liver," *Hepatology* 31(6):1251-1256.

Golub, T. R. et al. (Oct. 1999). "Molecular Classification of Cancer: Class Disovery and Class Prediction by Gene Expression Monitoring," *Science* 286:531-537.

Grant, S. C. D. et al. (Aug. 1996). "Serum Cytokines in Human Heart Transplant Recipients," *Transplantation* 62(4):480-491.

Gullestad, L. et al. (1999). "Effect of High-Versus Low-Dose Angiotensin Converting Enzyme Inhibition on Cytokine Levels in Chronic Heart Failure." *Journal of the American College of Cardiology* 34(7):2061-2067.

Harlow, E. et al. (1988). *Antibodies: A Laboratory Manual*, Cold Spring Harbor Laboratory: New York, NY, 9 pages. (Table of Contents).

Hastie, T. et al. (Aug. 2000), "Gene Shaving' as a Method for Identifying Distinct Sets of Genes with Similar Expression Patterns, " *Genome Biology* 1(2):research0003.1-0003.21.

Hastie, T. et al. (Jan. 2001), "Supervised Harvesting of Expression Trees," *Genome Biology* 2(1):research0003.1-0003.12.

Hayward, A. L. et al. (1998). "Modeling and Analysis of Competitive RT-PCR," *Nucleic Acids Research* 26(11):2511-2518.

Hayward-Lester, A. et al. (1995). "Accurate and Absolute Ouantitative Measurement of Gene Expression by Single Tube RT-PCR and HPLC," *Genome Research* 5:494-499.

Heller, R. A. et al. (Mar. 1997). "Discovery and Analysis of Inflammatory Disease-Related Genes Using cDNA Microarrays," *Proceedings of the National Academy of Sciences* 94:2150-2155.

Hendricks, D. A. et al. (Nov. 1995). "Quantitation of HBV DNA in Human Serum Using a Branched DNA (bDNA) Signal Amplification Assay," *American Journal of Clinical Pathology* 104(5):537-546.

Higuchi, K. et al. (1998). "Serum 2'-5' Oligoadenylate Synthetase Activity in Children. 2. Serum 2'-5' Oligoadenylate Synthetase in Childhood Collagen Disease," 342625a, *Chemical Abstracts* 129(26):406.

Hooks, J. J. et al. (1979). "Immune Interferon in the Circulation of Patients with Autoimmune Disease," *The New England Journal of Medicine* 301(1):5-8.

Hooks, J. J. et al. (Apr. 1982). "Multiple Interferons in the Circulation of Patients with Systemic Lupus Erythematosus and Vasculitis," *Arthritis and Rheumatism* 25(4):396-400.

Hsieh, H.-G. et al. (2001). "IL-17 Expression as a Possible Predictive Parameter for Subclinical Renal Allograft Rejection," *Transplant International* 14:287-298.

Iida, K. et al. (May 1982). "Complement Receptor (CR1) Deficiency in Erythrocytes from Patients with Systemic Lupus Erythematosus," *The Journal of Experimental Medicine* 155:1427-1438.

International Search Report mailed Jul. 18, 2002, for PCT Application No. PCT/US01/47856 filed Oct. 22, 2001, 3 pages.

International Search Report mailed Mar. 1, 2001, for PCT Application No. PCT/US00/17846 filed Jun. 28, 2000, 2 pages.

International Search Report mailed Sep. 23, 2005, for PCT Application No. PCT/US03/12946 filed Apr. 24, 2003, 4 pages.

International Search Report mailed Sep. 30, 2004, for PCT Application No. PCT/US03/13015 filed Apr. 24, 2003, 5 pages.

Jagota, A. (2000), "Nearest Neighbor Classifiers" Chapter 11 In *Data Analysis and Classification for Bioinformatics*, Department of Computer Science, University of California, Santa Cruz, pp. 92-93.

Kang, J. J. et al, (2000). "Transcript Quantitation in Total Yeast Cellular RNA Using Kinetic PCR," *Nucleic Acids Research* 28(2):e2, 8 pages.

Kasprzycka, M. et al. (2002). "Expression of FastL Gene in T cells of Renal Allograft Recipients," *Immunology Letters* 80:9-13.

Katz, M. H. (1999). "Assumptions of Multiple Linear Regression, Multiple Logistic Regression, and Proportional Hazards Analysis" In *Multivariable Analysis: A Practical Guide for Clinicians*. Cambridge University Press: Cambridge, United Kingdom, pp. 36-42.

Kendler, K. S. et al. (Jun. 1998). "The Structure of Psychosis Latent Class Analysis of Probands from the Roscommon Family Study," *Archives of General Psychiatry* 55:492-499.

Khan, J. et al. (Jun. 2001). "Classification and Diagnostic Prediction of Cancers Using Gene Expression Profiling and Artificial Neural Networks," *Nature Medicine* 7(6):673-679.

Kimball, P. et al. (Feb. 1995). "Cytokine Panel Predicts Early Rejection of Therapeutic Response After Cardiac Transplantation," *Transplantation Proceedings* 27(1):1286-1287.

Kobashigawa, J. et al. (Aug. 1998). "A Randomized Active-Controlled Trial of Mycophenolate Mofetil in Heart Transplant Recipients," *Transplantation* 66(4):507-515.

Kumar, R. et al. (Oct. 1994). "Cell Cycle-Dependent Modulation of Alpha-Interferon-Inducible Gene Expression and Activation of Signaling Components in Daudi Cells," *The Journal of Biological Chemistry* 269(41):25437-25441.

Kumar, S. et al. (2000). "Expansion and Molecular Evolution of the Interferon-Induced 2'-5' Oligoadenylate Synthetase Gene Family," *Molecular Biology and Evolution* 17(5):738-750.

Lee, M.-T. et al. (Aug. 29, 2000). "Importance of Replication in Microarray Gene Expression Studies: Statistical Methods and Evidence from Repetitive cDNA Hybridizations," *Proceedings of the National Academy of Sciences* 97(18):9834-9839.

Legros-Maida, S. et al. (1994). "Granzyme B and Perforin Can Be Used as Predictive Markers of Acute Rejection in Heart Transplantation," *European Journal of Immunology* 24:229-233.

Li, B. et al. (Mar. 2001). "Noninvasive Diagnosis of Renal-Allograft Rejection by Measurement of Messenger RNA for Perforin and Granzyme B in Urine," *The New England Journal of Medicine* 344(13):947-954.

Liossis, S.-N. C. (Mar. 2001). "B-cell Kinase Lyn Deficiency in Patients with Systemic Lupus Erythematosus," *Journal of Investigative Medicine* 49(2):157-165.

Loftus, B. J. et al. (1999). "Genome Duplications and Other Features in 12 Mb of DNA sequence from Human Chromosome 16p and 16q," *Genomics* 60:295-308.

Magnusson, M. et al. (2001). "Importance of CpG Dinucleotides in Activation of Natural IFN-Alpha-Producing Cells by a Lupus-Related Oligodeoxynucleotide," *Scandinavian Journal of Immunology* 54:543-550.

Marcelin, A.-G. et al. (Nov. 2001). "Effects of Cyclosporine and Hydrocortisone on Kaposi's Sarcoma-Associated Herpesvirus Genome Replication and Cell Apoptosis Induction," *Transplantation* 72(10):1700-1703.

Metler, M. et al. (Nov. 2001). "Expression of the Chemokine Receptor CXCR3 and Its Ligand IP-10 During Human Cardiac Allograft Rejection," *Circulation* 104:2558-2564.

Mohler III, E. R. et al. (Jul. 1997). "Role of Cytokines in the Mechanism of Action of Amlodipine: The Praise Heart Failure Trial," *Journal of the American College of Cardiology* 30(1):35-41.

Morita, K. et al. (2001). "Early Chemokine Cascades in Murine Cardiac Grafts Regulate T Cell Recruitment and Progression of Acute Allograft Rejection," *The Journal of Immunology* 167:2979-2984.

Morris, D. L. et al. (Feb. 1997). "Immunophenotyping Analysis of Peripheral Blood, Splenic, and Thymic Lymphocytes in Male and Female Rats," *Journal of Pharmacological and Toxicological Methods* 37(1):37-46.

Neto, E. D. et al. (Mar. 2000). "Shotgun Sequencing of the Human Transcriptome with ORF Expressed Sequences Tags," *Proceedings of the National Academy of Sciences* 97(7);3491-3496.

Nickel, P. et al. (Sep. 2001). "Cytotoxic Effector Molecule Gene Expression in Acute Renal Allograft Rejection," *Transplantation* 72(6):1158-1161.

Oh, S.-I. et al. (Apr. 2001). "Correlation of Fas and Faa Ligand Expression with Rejection Status of Transplanted Heart in Human," *Transplantation* 71(7):906-909.

Perou, C. M. et al. (Aug. 2000). "Molecular Portraits of Human Breast Tumours," *Nature* 406:747-752.

Pickles, A. et al. (1995). "Latent-Class Analysis of Recurrence Risks for Complex Phenotypes with Selection and Measurement Error: A Twin and Family History Study of Autism," *American Journal of Human Genetics* 57:717-726.

Preble, O. T. et al. (Apr. 1982). "Systemic Lupus Erythematosus: Presence in Human Serum of an Unusual Acid-Labile Leukocyte Interferon," *Science* 216:429-431.

Pruitt, K. D. et al. (Jan. 2000). "Introducing RefSeq and LocusLink: Curated Human Genome Resources at the NCBI," *Trends in Genetics* 16(1):44-47.

Quattrone, A. et al. (1995). "Quantitation of bcl-2 Oncogene in Cultured Lymphoma/Leukemia Cell Lines and in Primary Leukemia B-Cells by a Highly Sensitive RT-PCR Method," *Haematologica* 80:495-504.

Raychaudhuri, S. et al. (May 2001). "Basic Microarray Analysis: Grouping and Feature Reduction," *Trends in Biotechnology* 19(5):189-193.

Rebouillat, D. et al. (Jan. 1999). "The 100-kDa 2',5'-Oligoadenylate Synthase Catalyzing Preferentially the Synthesis of Dimeric pppA2'p5'A Molecules Is Composed of Three Homologous Domains," *The Journal of Biological Chemistry* 274(3):1557-1565.

Rus, V. et al. (Mar. 2002). "Expression of Cytokine- and Chemokine-Related Genes in Peripheral Blood Mononuclear Cells from Lupus Patients by cDNA Array," *Clinical Immunology* 102(3):283-290.

Saiura, A. et al. (Jul. 2001). "A Comparison of Gene Expression In Murine Cardiac Allografts and Isografts by Means DNA Microarray Analysis," *Transplantation* 72(2):320-329.

Salmon, J. E. et al. (Mar. 1996). "Fc-gamma-RIIA Alleles are Heritable Risk Factors for Lupus in African Americans," *The Journal of Clinical Investigation* 97(5):1348-1354.

Schena, M. et al. (Oct. 1995). "Quantitative Monitoring of Gene Expression Patterns with a Complementary DNA Microarray," *Science* 270:467-470.

Schena, M. et al. (Oct. 1996). "Parallel Human Genome Analysis: Microarray-based Expression Monitoring of 1000 Genes," *Proceedings of the National Academy of Sciences* 93:10614-10619.

Schowengert, K. O. et al. (May 2000). "Increased Expression of the Lymphocyte Early Activation Marker CD69 in Peripheral Blood Correlates with Histologic Evidence of Cardiac Allograft Rejection," *Transplantation* 69(10):2102-2107.

Sharma, V. K. et al. (Dec. 1996). "Molecular Executors of Cell Death-Differential Intrarenal Expression of Fas Ligand, Fas, Granzyme B, and Perforin During Acute and/or Chronic Rejection of Human Renal Allografts," *Transplantation* 62(12):1860-1866.

Shin, Y. K. et al. (Apr. 2001). "Expression of Leukemia-Associated Antigen, JL1, in Bone Marrow and Thymus," *American Journal of Pathology* 158(4):1473-1480.

Shirali, G. S. et al (May 2001). "Association of Viral Genome with Graft Loss in Children after Cardiac Transplantation," *The New England Journal of Medicine* 344(20):1498-1503.

Shoker, A. et al, (Aug. 2000). "Heightened CD40 Ligand Gene Expression in Peripheral CD4+ T Cells from Patients with Kidney Allograft Rejection," *Transplantation* 70(3):497-505.

Shou-Nee, S. et al. (1987). "Serum Interferon in Systemic Lupus Erythematosus," *British Journal of Dermatology* 117:155-159.

Shulzhenko, N. et al. (2001), "Monitoring of Intragraft and Peripheral Blood TIRC7 Expression as a Diagnostic Tool for Acute Cardiac Rejection in Humans," *Human Immunology* 62:342-347.

Shulzhenko, N. et al. (Nov. 2001). "Intragraft Activation of Genes Encoding Cytotoxic T Lymphocyte Effector Molecules Precedes the Histological Evidence of Rejection in Human Cardiac Transplantation," *Transplantation* 72(10):1705-1708.

Staudt, L. M. et al. (2000). "Genomic Views of the Immune System," *Annual Review of Immunology* 18:829-859.

Stellrecht, C. M. et al. (1991). "Expression Pattern of a Hematopoietic Proteoglycan Core Protein Gene During Human Hematopoiesis," *Differentiation* 48:127-135.

Stites, D. P. et al. eds. (1991). *Basic and Clinical Immunology*. 7th Edition, Appleton & Lange: East Norwalk, CT, 6 pages. (Table of Contents).

Strehlau, J. et al. (Jan. 1997). "Quantitative Detection Immune Activation Transcripts as a Diagnostc Tool in Kidney Transplantation," *Proceedings of the National Academy of Sciences* 94:695-700.

Tan, E. M. et al. (Nov. 1982). "The 1982 Revised Criteria for the Classification of Systemic Lupus Erythematosus," *Arthritis and Rheumatism* 25(2):1271-1277.

Tan, L. et al. (Mar. 2001). "Sequential Monitoring of Peripheral T-Lymphocyte Cytokine Gene Expression in the Early Post Renal Allograft Period," *Transplantation* 71(6):751-759.

Thomas, E. et al. (Jul. 2000). "Subtyping of Juvenile Idiopathic Arthritis Using Latent Class Analysis," *Arthritis & Rheumatism* 43(7):1496-1503.

Toogoo, G. J. et al. (Sep. 1996). "The Immune Response Following Small Bowel Transplantation," *Transplantation* 62(6):851-855.

Toronen, P. et al. (1999). "Analysis of Gene Expression Data Using Self-Organizing Maps," *FEBS Letters* 451:142-146.

Torre-Amione, G. et al. (Apr. 1996). "Proinflammatory Cytokine Levels in Patients with Depressed Left Ventricular Ejection Fraction: A Report from the Studies of Left Ventricular Dysfunction (SOLVD)," *Journal of the American College of Cardiology* 27(5):1201-1206.

Tsutamoto, T. et al. (Mar. 2000). "Angiotensin II Type 1 Receptor Antagonist Decreases Plasma Levels of Tumor Necrosis Factor Alpha, Interleukin-6 and Soluble Adhesion Molecules in Patients with Chronic Heart Failure," *Journal of the American College of Cardiology* 35(3):714-721.

Umek, R. M. et al. (May 2001). "Electronic Detection of Nucleic Acids: A Versatile Platform for Molecular Diagnostics," *Journal of Molecular Diagnostics* 3(2):74-84.

Vallin, H. et al. (1999). "Anti-Double-Stranded DNA Antibodies and Immunostimulatory Plasmid DNA in Combination Mimic the Endogenous IFN-Alpha Inducer in Systemic Lupus Erythematosus," *The Journal of Immunology* 163:6306-6313.

Vandevyver, C. et al. (1998). "Cytokine mRNA Profile of Myelin Basic Protein Reactive T-Cell Clones in Patients with Multiple Sclerosis," *Autoimmunity* 28:77-89.

Vignali, D. A. A. (2000). "Multiplexed Particle-Based Flow Cytometric Assays," *Journal of Immunological Methods* 243:243-255.

Vincenti, F. et al. (May 2001). "Multicenter Trial Exploring Calcineurin Inhibitors Avoidance in Renal Transplantation," *Transplantation* 71(9):1282-1287.

Vu, H. K. (2000). "A Method for Quantification of Absolute Amounts of Nucleic Acids by (RT)-PCR and a New Mathematical Model for Data Analysis," *Nucleic Acids Research* 28(7):e18, 9 pages.

Watanabe-Fukunaga, R. et al. (Mar. 1992). "Lymphoproliferation Disorder in Mice Explained by Detects in Fas Antigen that Mediates Apoptosis," *Nature* 356:314-317.

Weast, R. C. ed. (1968). *Handbook of Chemistry and Physics*. 49th Edition, The Chemical Rubber Co.: Cleveland, Ohio, 2 pages.

Welsh, J. B. et al. (Jan. 2001). "Analysis of Gene Expression Profiles in Normal and Neoplastic Ovarian Tissue Samples Identifies Candidate Molecular Markers of Epithelial Ovarian Cancer," *Proceedings of the National Academy of Sciences* 98(3):1176-1181.

Westin, L et al (Feb. 2000). "Anchored Multiplex Amplification on a Microelectronic Chip Array," *Nature Biotechnology* 18:199-204.

Whitehead, J. (Date Unknown). "An Introduction to Logistic Regression," Department of Economics, East Carolina University, located at <http://arts.uwaterloo.ca/~wnrr/Soc710_421/Whitehead%20Logistic%20Regression.ppt> (48 pages).

Wu, J. et al. (Sep. 1996). "Fas Ligand Mutation in a Patient with Systemic Lupus Erythematosus and Lymphoproliferative Disease," *The Journal of Clinical Investigation* 98(3):1107-1113.

Xia, D. et al. (Sep. 2001). "Real-Time Polymerase Chain Reaction Analysis Reveals an Evolution of Cytokine mRNA Production in Allograft Acceptor Mice,"*Transplantation* 72(5):907-914.

Yu, F. et al. (Oct. 1999). "Protein Synthesis-Dependent and Independent Induction of p69 2'-5'-Oligoadenylate Synthetase by Interferon-Alpha," *Cytokine* 11(10):744-750.

Zhang, L. et al. (Oct. 1997). "IRF-7, a New Interferon Regulatory Factor Associated with Epstein-Barr Virus Latency," *Molecular and Cellular Biology* 17(10):5748-5757.

Zucker, S. et al. (1999). "Increased Serum Stromelysin-1 Levels in Systemic Lupus Erythematosus: Lack of Correlation with Disease Activity," *Journal of Rheumatology* 26(1):78-80.

Abdallah, A. N. et al. (1997). "Evaluation of Plasma Levels of Tumor Necrosis Factor Alpha and Interleukin-6 as Rejection Markers in a Cohort of 142 Heart-Grafted Patients Followed by Endomyocardial Biopsy," *European Heart Journal* 18:1024-1029.

Ajjan, R. A. et al. (1996). "Intrathyroidal Cytokine Gene Expression in Hashimoto's Thyroiditis," *Clinical and Experimental Immunology* 105:523-528.

Akalin, E. et al. (Sep. 2001). "Gene Expression Analysis in Human Renal Allograft Biopsy Samples Using High-Density Oligoarray Technology," *Transplantation* 72(5):948-953.

Alizadeh, A. A. et al. (Feb. 2000). "Distinct Types of Diffuse Large B-cell Lymphoma Identified by Gene Expression Profiling," *Nature* 403:503-511.

Alizadeh, A. et al. (1999). "The Lymphochip: A specialized cDNA Microarray for the Genomic-scale Analysis of Gene Expression in Normal and Malignant Lymphocytes," *Cold Spring Harbor Symposia on Quantitative Biology* 54:71-78.

Alpert. S. et al. (Dec. 1995). "The Relationship of Granzyme A and Perforin Expression to Cardiac Allograft Rejection and Dysfunction," *Transplantation* 60(12):1478-1485.

Arnett, F. C. et al. (Mar. 1988). "The American Rheumatism Association 1987 Revised Criteria for the Classification of Rheumatoid Arthritis," *Arthritis and Rheumatism* 31(3):315-324.

Australian Written Opinion and Search Report mailed Oct. 7, 2005, for Singapore Application No. SG 200406287-3 filed Apr. 24, 2003, 12 pages.

Autieri, M. V. et al. (2002). "Allograft Inflammatory Factor-1 Expression Correlates with Cardiac Rejection and Development of Cardiac Allograft Vasculopathy," *Circulation* 106:2218-2223.

Baechler, E. C. et al. (Mar. 2003). "Interferon-Inducible Gene Expression Signature in Peripheral Blood Cells of Patients with Severe Lupus," *Proceedings of the National Academy of Sciences* 100(5):2610-2615.

Bakke, A. C. et al. (2001). "Neutrophil CD64 Expression Distinguishing Acute Inflammatory Autoimmune Disease from Systemic Infections," *Clinical and Applied Immunology Reviews* 1:267-275.

Bass, C. A. (Oct. 1993). "Clinical Evaluation of a New Polymerase Chain Reaction Assay for Detection of Chlamydia trachomatis in Endocervical Specimens," *Journal of Clinical Microbiology* 31(10):2648-2653.

Bave, U. (2000). "The Combination of Apoptotic U937 Cells and Lupus IgG is a Potent IFN-Alpha Inducer," *The Journal of Immunology* 165:3519-3526.

Bave, U. (2001). "Activation of Natural Interferon-Alpha Producing Cells by Apoptotic U937 Cells Combined with Lupus IgG and its Regulation by Cytokines," *Journal of Autoimmunity* 17:71-80.

Bittner, M. et al. (Aug. 2000). "Molecular Classification of Cutaneous Malignant Melanoma by Gene Expression Profiling," *Nature* 406:536-540.

Boelaert, M. et al. (May 1999). "Latent Class Analysis Permits Unbiased Estimates of the Validity of DAT for the Diagnosis of Visceral Leishmaniasis," *Tropical Medicine & International Health* 4(5):395-401.

Bombardier, C. et al. (Jun. 1992). "Derivation of the SLEDAI-A Disease Activity Index for Lupus Patients," *Arthritis and Rheumatism* 35(6):630-640.

Bustin, S. A. (2000). "Absolute Quantification of mRNA Using Real-Time Reverse Transcription Polymerase Chain Reaction Assays," *Journal of Molecular Endocrinology* 25:169-193.

Chang, D. M. et al. (1996). "Cytokines and Cell Surface Markers in Prediction of Cardiac Allograft Rejection," *Immunological Investigations* 25(1&2):13-21.

Chebath, J. et al, (Mar. 1987). "Four Different Forms of Interferon-Induced 2', 5'-0ilgo(A) Synthetase Identified by Immunoblotting in Human Cells," *The Journal of Biological Chemistry* 262(8):3852-2857.

Creemers, P. et al. (2002). "Evaluation of Peripheral Blood CD4 and CD8 Lymphocyte Subsets, CD69 Expression and Histologic, Rejection Grade as Diagnostic Markers for the Presence of Cardiac Allograft Rejection," *Transplant Immunology* 10:285-292.

Damas, J. K. et al, (2001). "Enhanced Gene Expression of Chemokines and their Corresponding Receptors in Mononuclear Blood Cells in Chronic Heart Failure—Modulatory Effect of Intravenous Immunoglobin," *Journal of the American College of Cardiology* 38(1):187-193.

Davas, E. M. et al. (1999). "Serum IL-6, TNF-alpha, p55 srTNF-alpha, p75srTNF-alpha, srIL-2-alpha Levels and Disease Activity in Systemic Lupus Erythematosus," *Clinical Rheumatology* 18:17-22.

Deng, M. C. et al. (Nov. 1995). "The Relation of Interleukin-6, Tumor Necrosis Factor-Alpha, IL-2, and IL-2 Receptor Levels to Cellular Rejection, Allograft Dysfunction, and Clinical Events Early After Cardiac Transplantation," *Transplantation* 60(10):1118-1124.

Deuel, T. F. et al. (Jul. 1981). "Platelet Factor 4 is Chemotactic for Neutrophils and Monocytes," *Proceedings of the National Academy of Sciences* 78(7):4584-4587.

Deuel, T. F. et al. (Jun. 1977). "Amino Acid Sequence of Human Platelet Factor 4," *Proceedings of the National Academy of Sciences* 74(6):2256-2258.

Bertone, P. et al. (Dec. 24, 2004). "Global Identification of Human Transcribed Sequence with Genome Tiling Arrays," *Science* 306:2242-2246.

Flechner, S. M. et al. (2004). "Kidney Transplant Rejection and Tissue Injury by Gene Profiling of Biopsies and Peripherals Blood Lymphocytes," *American Journal of Transplantation* 4:1475-1489.

Galon, J. et al. (Jan. 2002). "Gene Profiling Reveals Unknown Enhancing and Suppressive Actions of Glucocorticoids on Immune Cells," *The FASEB Journal* 16:61-71.

International Search Report and Written Opinion mailed Aug. 25, 2008, for PCT Application No. PCT/US07/08909 filed Apr. 9, 2007, 10 pages.

International Search Report and Written Opinion mailed Jun. 25, 2008, for PCT Application No. PCT/US06/18381 filed May 11, 2006, 8 pages.

Mansfield, E. S. et al. (2004). "Arraying the Orchestration of Allograft Pathology," *American Journal of Transplantation* 4:853-862.

International Search Report and Written Opinion mailed Sep. 10, 2008, for PCT Application No. PCT/US07/18135 filed Aug. 14, 2007, 12 pages.

Keembiyehetty, C. et al. (Mar. 2006). "Mouse Glucose Transporter 9 Splice Variants Are Expressed in Adult Liver and Kidney and Are Up-regulated in Diabetes," *Molecular Endocrinology* 20(3):686-697.

Kelsen, S. et al. (2004). "The Chemokine Receptor CXCR3 and its Splice Variant are Expressed in Human Airway Epithelial Cells," *American Journal of Physiology-Lung Cellular and Molecular Physiology* 287:L584-L591.

Seiter, S. et al. (1998). "CD44 Variant Isoform Expression in a Variety of Skin-Associated Autoimmune Diseases," *Clinical Immunology and Immunopathology* 89(1):79-93.

Zhu, H. et al. (Nov. 2005). "The Role of Hyaluronan Receptor CD44 in MSC Migration in The Extracellular Matrix," *Stem Cells Express* 1-32.

Benner, S. A. et al. (Jul. 2001). "Evolution, Language and Analogy in Functional Genomics," *Trends in Genetics* 17(7):414-418.

Bennett, L. et al. (Mar. 17, 2003). "Interferon and Granulopoiesis Signatures in Systemic Lupus Erythematosus Blood," *The Journal of Experimental Medicine* 197(6):711-723.

Bergholdt, R. et al. (2000). "Characterization of New Polymorphisms in the 5' UTR of the Human Interleukin-1 Receptor Type 1 (IL1R1) Gene: Linkage to Type 1 Diabetes and Correlation to IL-1RI Plasma Level," *Genes and Immunity* 1:495-500

Centola, M. et al. (2006). "Genome-Scale Assessment of Molecular Pathology in Systemic Autoimmune Diseases Using Microarray Technology: A Potential Breakthrough Diagnostic and Individualized Therapy-Design Tool," *Scandinavian Journal of Immunology* 64:236-242.

Crow, M. K. et al. (2003). "Microarray Analysis of Gene Expression in Lupus," *Arthritis Research & Therapy* 5(6):279-287.

Dozmorov, M. G. et al. (2007). "5α-Androstane-3α, 17β-Diol Selectively Activates the Canonical PI3K/AKT Pathway: A Bioinformatics-Based Evidence for Androgen-Activated Cytoplasmic Signaling," *Genomic Medicine* 1:139-146.

Horwitz, P. A. et al. (2004). "Detection of Cardiac Allograft Rejection and Response to Immunosuppressive Therapy with Peripheral Blood Gene Expression," *Circulation* 110:3815-3821.

Ing, N. H. (2005). "Steroid Hormones Regulate Gene Expression Posttranscriptionally by Altering the Stabilities of Messenger RNAs," *Biology of Reproduction* 72:1290-1296.

Invitation to Pay Additional Fees mailed Apr. 27, 2009, for PCT Application No. PCT/US2007/023675 filed Nov. 9, 2007, 6 pages.

Kaufman, D. B. et al. (1997). "Functional Significance of Donor Islet Interleukin-1 Receptor Type 1 (IL-1Rt1) Expression in Islet Transplantation," *Transplantation Proceedings* 29:772-773.

Kirou, K. A et al. (Dec. 2004). "Coordinate Overexpression of Interferon-α-Induced Genes in Systemic Lupus Erythematosus," *Arthritis & Rheumatism* 50(12):3958-3967.

Mandel, M. et al. (2006). "Gene Expression Studies in Systemic Lupus Erythematosus," *Lupus* 15:451-456.

Smith, A. D. et al. eds. (1997). *Oxford Dictionary of Biochemistry and Molecular Biology*. Oxford University Press, Oxford, New York, p. 618.

Tanaka, J. et al. (1995). "Cytokine Receptor Gene Expression in Peripheral Blood Mononuclear Cells During Graft-Versus-Host Disease After Allogeneic Bone Marrow Transplantation," *Leukemia and Lymphoma* 19:281-287.

U.S. Office Action mailed May 29, 2009, for U.S. Appl. No. 11/784,998, filed Apr. 9, 2007, 28 pages.

U.S. Office Action mailed May 29, 2009, for U.S. Appl. No. 11/893,236, filed Aug. 14, 2007, 12 pages.

Vamvakopoulos, J. et al. (2002). "Genetic Control of IL-1β Bioactivity Through Differential Regulation of the IL-1 Receptor Antagonist," *European Journal of Immunology* 32:2988-2996.

\* cited by examiner

A.

B.

C.

D.

GENES USEFUL FOR DIAGNOSING AND MONITORING INFLAMMATION RELATED DISORDERS

RELATED APPLICATIONS

This application claims the benefit under 35 USC 119(e) of Provisional Application No. 60/608,403, filed Sep. 8, 2004 which is hereby incorporated by reference in its entirety.

FIELD OF THE INVENTION

This invention is in the field of expression profiling for monitoring organ transplantation and inflammation related disorders.

BACKGROUND OF THE INVENTION

Many of the current shortcomings in diagnosis, prognosis, risk stratification and treatment of disease can be approached through the identification of the molecular mechanisms underlying a disease and through the discovery of nucleotide sequences (or sets of nucleotide sequences) whose expression patterns predict the occurrence or progression of disease states, or predict a patient's response to a particular therapeutic intervention. In particular, identification of nucleotide sequences and sets of nucleotide sequences with such predictive value from cells and tissues that are readily accessible would be extremely valuable. For example, peripheral blood is attainable from all patients and can easily be obtained at multiple time points at low cost. This is a desirable contrast to most other cell and tissue types, which are less readily accessible, or accessible only through invasive and aversive procedures. In addition, the various cell types present in circulating blood are ideal for expression profiling experiments as the many cell types in the blood specimen can be separated if desired prior to analysis of gene expression. While blood provides a very attractive substrate for the study of diseases using expression profiling techniques, and for the development of diagnostic technologies and the identification of therapeutic targets, the value of expression profiling in blood samples rests on the degree to which changes in gene expression in these cell types are associated with a predisposition to, and pathogenesis and progression of a disease.

In particular, acute allograft rejection diagnosis and monitoring may benefit from such an approach. Current diagnosis and monitoring of acute allograft rejection is achieved through invasive allograft biopsy and assessment of the biopsy histology. This approach is sub-optimal because of the expense of the procedure, cost, pain and discomfort of the patient, the need for trained physician operators, the risk of complications of the procedure, the lack of insight into the functioning of the immune system and variability of pathological assessment. In addition, biopsy can diagnose acute allograft rejection only after significant cellular infiltration into the allograft has occurred. At this point, the process has already caused damage to the allograft. For all these reasons, a simple blood test that can diagnose and monitor acute rejection at an earlier stage in the process is needed. Allograft rejection depends on the presence of functioning cells of the immune system.

There is an extensive literature supporting the role of leukocytes, e.g., T- and B-lymphocytes, monocytes and granulocytes, including neutrophils, in a wide range of disease processes, including such broad classes as cardiovascular diseases, inflammatory, autoimmune and rheumatic diseases, infectious diseases, transplant rejection, cancer and malignancy, and endocrine diseases. For example, among cardiovascular diseases, such commonly occurring diseases as atherosclerosis, restenosis, transplant vasculopathy and acute coronary syndromes all demonstrate significant T cell involvement (Smith-Norowitz et al. (1999) *Clin Immunol* 93:168-175; Jude et al. (1994) *Circulation* 90:1662-8; Belch et al. (1997) *Circulation* 95:2027-31). These diseases are now recognized as manifestations of chronic inflammatory disorders resulting from an ongoing response to an injury process in the arterial tree (Ross et al. (1999) *Ann Thorac Surg* 67:1428-33). Differential expression of lymphocyte, monocyte and neutrophil genes and their products has been demonstrated clearly in the literature. Particularly interesting are examples of differential expression in circulating cells of the immune system that demonstrate specificity for a particular disease, such as arteriosclerosis, as opposed to a generalized association with other inflammatory diseases, or for example, with unstable angina rather than quiescent coronary disease.

A number of individual genes, e.g., CD11b/CD18 (Kassirer et al. (1999) *Am Heart J* 138:555-9); leukocyte elastase (Amaro et al. (1995) *Eur Heart J* 16:615-22; and CD40L (Aukrust et al. (1999) *Circulation* 100:614-20) demonstrate some degree of sensitivity and specificity as markers of various vascular diseases. In addition, the identification of differentially expressed target and fingerprint genes isolated from purified populations of monocytes manipulated in various in vitro paradigms has been proposed for the diagnosis and monitoring of a range of cardiovascular diseases, see, e.g., U.S. Pat. Nos. 6,048,709; 6,087,477; 6,099,823; and 6,124,433 "COMPOSITIONS AND METHODS FOR THE TREATMENT AND DIAGNOSIS OF CARDIOVASCULAR DISEASE" to Falb (see also, WO 97/30065). Lockhart, in U.S. Pat. No. 6,033,860 "EXPRESSION PROFILES IN ADULT AND FETAL ORGANS" proposes the use of expression profiles for a subset of identified genes in the identification of tissue samples, and the monitoring of drug effects.

The accuracy of technologies based on expression profiling for the diagnosis, prognosis, and monitoring of disease would be dramatically increased if numerous differentially expressed nucleotide sequences, each with a measure of sensitivity and specificity for a disease in question, could be identified and assayed in a concerted manner. Using the expression of multiple genes (gene sets) for diagnostic applications can help overcome assay and population variability. PCT application WO 02/057414 "LEUKOCYTE EXPRESSION PROFILING" to Wohlgemuth identifies one such set of differentially expressed nucleotides.

In order to achieve this improved accuracy, the sets of nucleotide sequences once identified need to be validated to identify those differentially expressed nucleotides within a given set that are most useful for diagnosis, prognosis, and monitoring of disease. The present invention addresses these and other needs, and applies to transplant rejection for which differential regulation of genes, or other nucleotide sequences, of peripheral blood can be demonstrated.

SUMMARY OF THE INVENTION

The present invention is thus directed to a system for monitoring gene expression for diagnosing and monitoring inflammation disorders. Gene expression is monitored by detecting the expression levels of one or more nucleotide sequences. The present invention is directed to a system for monitoring gene expression in inflammation disorders in response to a particular drug treatment regimen. Particular genes and nucleic acids of interest which find use in the system of the invention include those described in U.S. Pat. No. 6,905,827, U.S. patent application Ser. Nos. 10/006,290; 10/131,827; 60/296,764, 60/241,994, 10/131,831; 10/511,937; 10/512,028 and 10/325,899 and incorporated herein by reference in their entirety and those described herein. Any drug treatment may be monitored using the system and methods of the invention. Of particular interest are immunosuppressive drugs. Such immunosuppressive drugs may include steroids, cyclosporine, tacrolimus and other drugs.

Gene expression may be monitored using the system and methods of the invention to measure or determine the efficacy or effectiveness of a particular drug regimen. Gene expression monitoring may involve monitoring the expression of certain genes, certain sets of genes or genes involved in specific pathways. Such monitoring could be done in vivo through blood sampling of patients or in vitro through treatment of cells.

The system and methods of the invention find particular use in monitoring transplant rejection patients. In particular, the system and methods of the invention may be utilized to monitor the effects of immunosuppressive drugs on transplant patients. The methods find use in identifying specific genes, gene sets and pathways whose expression correlates with certain immunosuppressive drugs and levels of certain immunosuppressive drugs. Such genes are particularly useful in immunosuppressive drug monitoring.

The present invention is further directed to a system for detecting differential gene expression using one or more of a set of four genes identified in this specification as having utility in monitoring transplant rejection and other inflammation related disorders. In one aspect, the invention is directed to a method of diagnosing or monitoring transplant rejection and other inflammation related disorders in a patient by detecting the expression level of one or more genes in the patient to diagnose or monitor transplant rejection in the patient, wherein the one or more genes include a nucleotide sequence selected from SEQ ID NO:5, SEQ ID NO:11, SEQ ID NO:17 and SEQ ID NO:23. In one variation, the invention is further directed to detecting the expression level of one or more additional genes in the patient to diagnose or monitor transplant rejection in the patient, wherein the one or more additional genes are differentially expressed in response to changes in transplant rejection or other inflammation related disorders. By way of example, the invention is directed to an improved method of diagnosing or monitoring transplant rejection and other inflammation related disorders in a patient by detecting the expression level of one or more genes in the patient to diagnose or monitor transplant rejection in a patient, wherein in the one or more genes include a nucleotide sequence selected from Table 8 in U.S. patent application Ser. No. 10/006,290 (such table herein incorporated by reference in its entirety), wherein the improvement includes detecting the expression level of one or more additional genes in the patient to diagnose or monitor transplant rejection in a patient, wherein the one or more genes include a nucleotide sequence selected from SEQ ID NO:5, SEQ ID NO:11, SEQ ID NO:17 and SEQ ID NO:23.

In a further variation, the invention is directed to a method of diagnosing or monitoring cardiac transplant rejection in a patient by detecting the expression level of one or more genes in the patient to diagnose or monitor cardiac transplant rejection in the patient wherein the one or more genes include a nucleotide sequence selected from SEQ ID NO:5, SEQ ID NO:11, SEQ ID NO:17 and SEQ ID NO:23. In one variation, the method includes detecting the expression level of one or more additional genes in the patient to diagnose or monitor cardiac transplant rejection in the patient, wherein the one or more additional genes are differentially expressed in response to changes in cardiac transplant rejection.

The invention is also directed to a method of diagnosing or monitoring lung transplant rejection in a patient by detecting the expression level of one or more genes in the patient to diagnose or monitor lung transplant rejection in the patient wherein the one or more genes include a nucleotide sequence selected from SEQ ID NO:5, SEQ ID NO:11, SEQ ID NO:17 and SEQ ID NO:23. In one variation, the method further includes detecting the expression level of one or more additional genes in the patient to diagnose or monitor lung transplant rejection in a patient, wherein the one or more additional genes are differentially expressed in response to changes in lung transplant rejection.

The invention is also directed to a method of diagnosing or monitoring kidney transplant rejection in a patient by detecting the expression level of one or more genes in the patient to diagnose or monitor kidney transplant rejection in the patient wherein the one or more genes include a nucleotide sequence selected from SEQ ID NO:5, SEQ ID NO:11, SEQ ID NO:17 and SEQ ID NO:23. In one variation, the method further includes detecting the expression level of one or more additional genes in the patient to diagnose or monitor kidney transplant rejection in a patient, wherein the one or more additional genes are differentially expressed in response to changes in kidney transplant rejection.

In another aspect, the methods of diagnosing or monitoring transplant rejection include detecting the expression level of at least two, at least three, or all four of the genes in the group consisting of SEQ ID NO:5, SEQ ID NO:11, SEQ ID NO:17 and SEQ ID NO:23. In another variation, methods of diagnosing or monitoring transplant rejection include detecting the expression level of at least two genes, at least three genes, at least four genes, at least five genes, at least six genes, at least eight genes, at least ten genes, at least fifteen genes, or at least twenty genes, wherein at least one, at least two, at least three, or all four of the genes include a nucleotide sequence selected from SEQ ID NO:5, SEQ ID NO:11, SEQ ID NO:17 and SEQ ID NO:23. In a further variation, the methods of diagnosing or monitoring transplant rejection include detecting the expression level of at least one hundred of the genes. In still a further variation, the methods of diagnosing or monitoring transplant rejection include detecting the expression level of all the listed genes.

The present invention is further directed to a system for detecting nucleic acid expression in a body fluid comprising an isolated polynucleotide wherein the isolated polynucleotide detects expression of a nucleic acid wherein the nucleic acid comprises a nucleotide sequence wherein the nucleotide sequence is selected from SEQ ID NO: 5; SEQ ID NO:11; SEQ ID NO:17; and SEQ ID NO: 23 and such nucleic acid is differentially expressed in body fluid in an individual with at least one disease criterion for a disease selected from Table 1 compared to the expression of the nucleic acid in body fluid of the individual without the at least one disease criterion.

TABLE 1

| Disease Classification | Disease/Patient Group |
| --- | --- |
| Cardiovascular | Atherosclerosis |
| | Myocardial Infarction |
| | Restinosis after angioplasty |
| | Congestive Heart Failure |
| | Myocarditis |
| | Endocarditis |
| | Endothelial Dysfunction |
| | Cardiomyopathy |

TABLE 1-continued

| Disease Classification | Disease/Patient Group |
|---|---|
| Infectious Disease | Cardiovascular drug use |
| | Hepatitis A, B, C, D, E, G |
| | Malaria |
| | Tuberculosis |
| | HIV |
| | Pneumocystis Carinii |
| | Giardia |
| | Toxoplasmosis |
| | Lyme Disease |
| | Rocky Mountain Spotted Fever |
| | Cytomegalovirus |
| | Epstein Barr Virus |
| | Herpes Simplex Virus |
| | Clostridium Dificile Colitis |
| | Meningitis (all organisms) |
| | Pneumonia (all organisms) |
| | Urinary Tract Infection (all organisms) |
| | Infectious Diarrhea (all organisms) |
| | Anti-infectious drug use |
| Angiogenesis | Pathological Angiogenesis |
| | Physiologic Angiogenesis |
| | Trastement induced angiogenesis |
| | Pro or anti-angiogenic drug use |
| Transplant Rejection | Heart |
| | Lung |
| | Liver |
| | Pancreas |
| | Bowel |
| | Bone Marrow |
| | Stem Cell |
| | Graft versus host disease |
| | Transplant vasculopathy |
| | Skin |
| | Cornea |
| | Islet Cells |
| Transplant Rejection (continued) | Kidney |
| | Xenotransplants |
| | Mechanical Organ |
| | Immunosuppressive Organ |
| Hematological Disorders | Anemia - Iron Deficiency |
| | Anemia - B12, Folate deficiency |
| | Anemia - Aplastic |
| | Anemia - hemolytic |
| | Anemia - Renal failure |
| | Anemia - Chronic disease |
| | Polycythemia rubra vera |
| | Pernicious anemia |
| | Idiophic Thrrombocytopenic purpura |
| | Thrombotic Thrombocytopenic purpura |
| | Essential thrombocytosis |
| | Leukemia |
| | Cytopenias due to immunosupression |
| | Cytopenias due to Chemotherapy |
| | Myelodysplasia |
| Endocrine Disease | Diabetes Mellitus I and II |
| | Thyroiditis |
| | Autoimmune polyglandular syndrome |
| | Autoimmune oophoritis |
| | Autoimmune hypophysitis |
| | Addisson's Disease |
| Inflammatory/Rheumatic Disease | Rheumatoid Arthritis |
| | Systemic Lupus Erythematosis |
| | Sjogrens Disease |
| | CREST syndrome |
| | Scleroderma |
| | Ankylosing Spondylitis |
| | Crohn's |
| | Ulcerative Colitis |
| | Primary Sclerosing Cholangitis |
| Inflammatory/Rheumatic Disease | Appendicitis |
| | Diverticulitis |
| | Primary Biliary Sclerosis |
| | Wegener's Granulomatosis |
| | Polyarteritis nodosa |
| | Whipple's Disease |
| | Psoriasis |
| | Microscopic Polyanngiitis |
| | Takayasu's Disease |
| | Kawasaki's Disease |
| | Autoimmune hepatitis |
| Inflammatory/Rheumatic Disease(continued) | Asthma |
| | Churg-Strauss Disease |
| | Beurger's Disease |
| | Raynaud's Disease |
| | Cholecystitis |
| | Sarcoidosis |
| | Asbestosis |
| | Pneumoconioses |
| | Otic inflammatory disease |
| | Ophthalmic inflammatory disease |
| | Antinflammatory drug use |
| Neurological Disease | Alzheimer's Dementia |
| | Pick's Disease |
| | Multiple Sclerosis |
| | Guillain Barre Syndrome |
| | Post-viral neuropathies |
| | Peripheral Neuropathy |

The present invention is further directed to a method of diagnosing or monitoring transplant rejection or other inflammation related disorder in a patient, including detecting the expression level of a nucleic acid in the patient to diagnose or monitor transplant rejection or other inflammation related disorder in the patient wherein the nucleic acid comprises a nucleotide sequence selected from the group consisting of SEQ ID NO: 5; SEQ ID NO: 11; SEQ ID NO:17 and SEQ ID NO: 23.

In another variation, transplant rejection may be selected from heart transplant rejection, kidney transplant rejection, liver transplant rejection, pancreas transplant rejection, pancreatic islet transplant rejection, lung transplant rejection, bone marrow transplant rejection, stem cell transplant rejection, xenotransplant rejection, and mechanical organ replacement rejection.

In another aspect, the methods of detecting transplant rejection include detecting the expression level by measuring the RNA level expressed by one or more genes. The method may further including isolating RNA from the patient prior to detecting the RNA level expressed by the one or more genes.

In one variation, the RNA level is detected by PCR. In a still further variation, the PCR uses primers consisting of pairs of nucleotide sequences selected from the group consisting of SEQ ID NOs: 1 and 2, SEQ ID NOs:7 and 8, SEQ ID NOs: 13 and 14, and SEQ ID NOs:19 and 20. The RNA level may be detected by hybridization to the probes. In a further variation, the RNA level is detected by hybridization to an oligonucleotide. Examples of oligonucleotide include oligonucleotides having a nucleotide sequence selected from SEQ ID NO:3, SEQ ID NO:9, SEQ ID NO:15, and SEQ ID NO:21. The oligonucleotide may be DNA, RNA, cDNA, PNA, genomic DNA, or synthetic oligonucleotides.

In another aspect, the methods of detecting transplant rejection include detecting the expression level by measuring one or more proteins expressed by the one or more genes. In one variation, the one or more proteins include an amino acid sequence selected from SEQ ID NO:6, SEQ ID NO:12, SEQ ID NO:18, and SEQ ID NO:24.

In another aspect, the method of diagnosing or monitoring cardiac transplant rejection in a patient includes detecting the expression level of one or more genes in the patient to diagnose or monitor cardiac transplant rejection in the patient by measuring one or more proteins expressed by the one or more genes. The one or more proteins may include an amino acid sequence selected from SEQ ID NO:6, SEQ ID NO:12, SEQ ID NO:18, and SEQ ID NO:24.

In another aspect, the method of diagnosing or monitoring kidney transplant rejection in a patient includes detecting the expression level of one or more genes in the patient to diagnose or monitor kidney transplant rejection in the patient by measuring one or more proteins encoded by the one or more genes. In one variation, the one or more proteins include an amino acid sequence selected from SEQ ID NO:6, SEQ ID NO:12, SEQ ID NO:18, and SEQ ID NO:24.

Protein detection may be accomplished by measuring serum. In another variation, the protein is a cell surface protein. In a further variation, the measuring includes using a fluorescence activated cell sorter.

In another aspect, the invention is directed to a substantially purified oligonucleotide having the nucleotide sequence selected from SEQ ID NO:5, SEQ ID NO:11, SEQ ID NO:17, and SEQ ID NO:23, a substantially purified oligonucleotides having at least 90% sequence identity to an oligonucleotide having the nucleotide sequence selected from SEQ ID NO:5, SEQ ID NO:11, SEQ ID NO:17 and SEQ ID NO:23, or a substantially purified oligonucleotide that hybridizes at high stringency to an oligonucleotide having the nucleotide sequence selected from SEQ ID NO:5, SEQ ID NO:11, SEQ ID NO:17 and SEQ ID NO:23. The sequences may be used as diagnostic oligonucleotides for transplant rejection and/or cardiac transplant rejection. The sequences may also be used to design diagnostic oligonucleotides for transplant rejection and/or cardiac transplant rejection. The oligonucleotide may have nucleotide sequence including DNA, cDNA, PNA, genomic DNA, or synthetic oligonucleotides.

In another aspect, the invention is directed to a method of diagnosing or monitoring transplant rejection in a patient wherein the expression level of one or more genes in a patient's bodily fluid is detected. In a further variation, the bodily fluid is peripheral blood.

In another aspect, the invention is directed to a method of diagnosing or monitoring transplant rejection in a patient, comprising detecting the expression level of four or more genes in the patient to diagnose or monitor transplant rejection in the patient wherein the four or more genes include a nucleotide sequence selected from SEQ ID NO:5, SEQ ID NO:11, SEQ ID NO:17 and SEQ ID NO:23.

In another aspect, the invention is directed to a method of diagnosing or monitoring kidney transplant rejection in a patient by detecting one or more proteins in a bodily fluid of the patient to diagnose or monitor transplant rejection in the patient wherein the one or more proteins have a protein sequence selected from SEQ ID NO:6, SEQ ID NO:12, SEQ ID NO:18, and SEQ ID NO:24.

In a further aspect, the invention is also directed to a system for detecting gene expression in body fluid including at least two isolated polynucleotides wherein the isolated polynucleotides detect expression of a gene wherein the gene includes a nucleotide sequence selected from SEQ ID NO:5, SEQ ID NO:11, SEQ ID NO:17 and SEQ ID NO:23 and the gene is differentially expressed in body fluid in an individual rejecting a transplanted organ compared to the expression of the gene in leukocytes in an individual not rejecting a transplanted organ.

BRIEF DESCRIPTION OF THE SEQUENCE LISTING

SEQ ID NO: 1, 7, 13, and 19 are forward (sense strand) PCR primers.

SEQ ID NO: 2, 8, 14, and 20 are reverse PCR primers.

SEQ ID NO: 3, 9, 15, and 21 are Taqman Tm probe sequences.

SEQ ID NO: 4, 10, 16, and 22 are the amplicon sequences for the four Taqman Tm assays.

SEQ ID NO: 5, 11, 17 and 23 are the sequences used to design the Taqman Tm assays.

SEQ ID NO: 6, 12, 18 and 24 are the proteins coded by the genes.

SEQ ID NO: 25-41 are genes and primers discussed in the Examples.

SEQ ID NO: 1-6 correspond to the diagnostic gene—Homo sapiens signal-regulatory protein beta 1 (SIRPB1).

SEQ ID NO: 7-12 correspond to the diagnostic gene—Homo sapiens S100 calcium binding protein A9 (calgranulin B) (S100A9).

SEQ ID NO: 13-18 correspond to the diagnostic gene—Homo sapiens zinc finger protein, subfamily 1A, 1 (Ikaros) (ZNFN1A1).

SEQ ID NO: 19-24 correspond to the diagnostic gene—Homo sapiens immunoglobulin J polypeptide, linker protein for immunoglobulin alpha and mu polypeptides (IGJ).

The Sequence Listings and genes described in U.S. patent application Ser. Nos. 10/006,290; 10/131,827; 10/131,831 and 10/325,899 are also incorporated by reference herein in their entirety.

BRIEF DESCRIPTION OF THE FIGURES

FIG. 1A shows a β-GUS gel image. Lane 3 is the image for primers F178 and R242. Lanes 2 and 1 correspond to the no-template control and -RT control, respectively. FIG. 1B shows the electropherogram of β-GUS primers F178 and R242, a graphical representation of Lane 3 from the gel image. FIG. 1C shows a β-Actin gel image. Lane 3 is the image for primers F75 and R178. Lanes 2 and 1 correspond to the no-template control and -RT control, respectively. FIG. 1D shows the electropherogram of β-Actin primers F75 and R178, a graphical representation of Lane 3 from the gel image.

FIG. 3 shows real-time PCR control gene analysis. Eleven candidate control genes were tested using real-time PCR on 6 whole blood samples (PAX) paired with 6 mononuclear samples (CPT) from the same patient. Each sample was tested twice. For each gene, the variability of the gene across the samples is shown on the vertical axis (top graph). The average Ct value for each gene is also shown (bottom graph). 2 ug RNA was used for PAX samples and 0.5 ug total RNA was used for the mononuclear samples (CPT).

BRIEF DESCRIPTION OF THE TABLES

Figure 1:
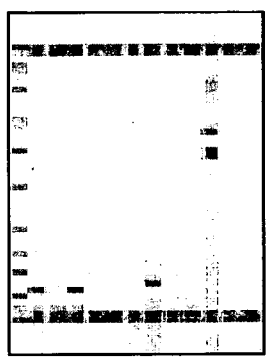
FIG. 1 shows endpoint testing of PCR primers where electrophoresis and microfluidics are used to assess the product of gene specific PCR primers.
Figure 1:
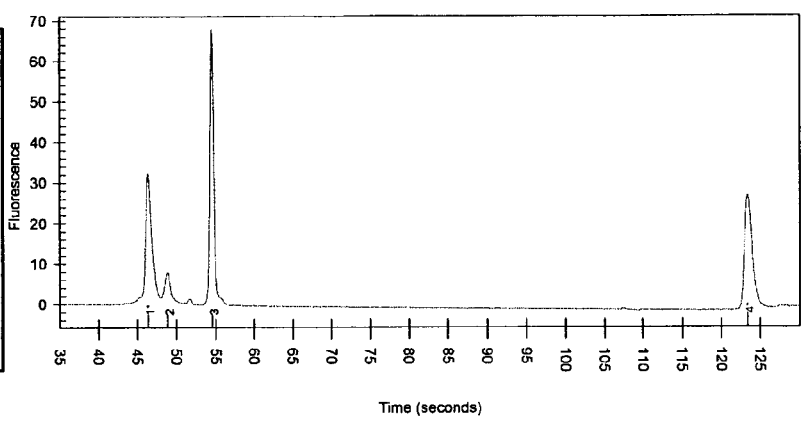
Figure 1:
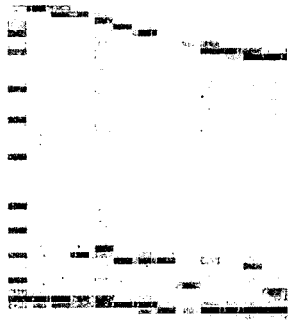
Figure 1:
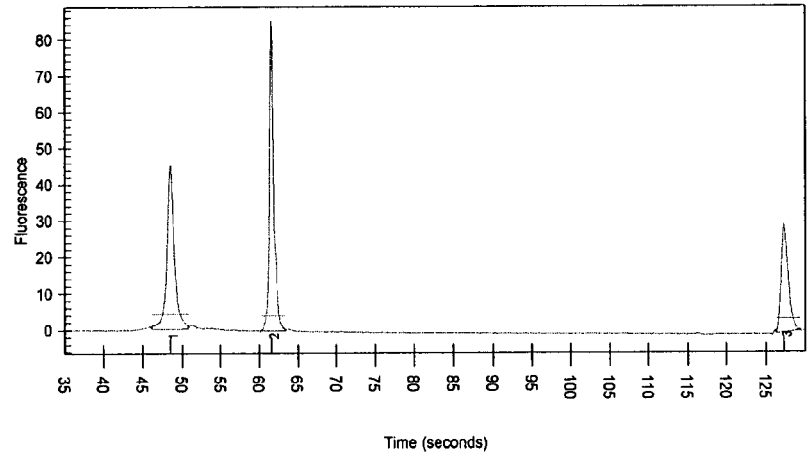

Table 1: Table 1 lists diseases or conditions amenable to study by leukocyte profiling.

Table 2: Table 2 shows gene expression data for patients treated with cyclosporine Table 3: Table 3 shows real-time PCR assay reporter and quencher dyes. Various combinations of reporter and quencher dyes are useful for real-time PCR assays. Reporter and quencher dyes work optimally in specific combinations defined by their spectra. For each reporter, appropriate choices for quencher dyes are given.

DESCRIPTION OF THE PREFERRED EMBODIMENTS OF THE INVENTION

Definitions

Unless defined otherwise, all scientific and technical terms are understood to have the same meaning as commonly used in the art to which they pertain. For the purpose of the present invention, the following terms are defined below.

In the context of the invention, the term "gene expression system" refers to any system, device or means to detect gene expression and includes diagnostic agents, diagnostic oligonucleotides, and diagnostic oligonucleotide sets or probe sets. Genes are referenced herein by particular nucleotide sequences.

The term "monitoring" is used herein to describe the use of individual genes or gene sets to provide useful information about an individual or an individual's health or disease status. "Monitoring" can include, determination of prognosis, risk-stratification, selection of drug therapy, assessment of ongoing drug therapy, prediction of outcomes, determining response to therapy, diagnosis of a disease or disease complication, following progression of a disease or providing any information relating to a patients health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example a cascade of tests from a non-invasive blood test to a more invasive option such as biopsy, or testing to assess side effects of drugs used to treat another indication.

The term "diagnostic oligonucleotide" or "diagnostic oligonucleotide set" generally refers to an oligonucleotide or a set of two or more oligonucleotides that, when evaluated for differential expression of their corresponding diagnostic gene(s), collectively yields predictive data. Such predictive data typically relates to diagnosis, prognosis, monitoring of therapeutic outcomes, and the like. In general, the components of a diagnostic oligonucleotide or a diagnostic oligonucleotide set are distinguished from nucleotide sequences that are evaluated by analysis of the DNA to directly determine the genotype of an individual as it correlates with a specified trait or phenotype, such as a disease, in that it is the pattern of expression of the components of the diagnostic oligonucleotide or the diagnostic oligonucleotide set, rather than mutation or polymorphism of the DNA sequence that provides predictive value. It will be understood that a particular component (or member) of a diagnostic oligonucleotide set can, in some cases, also present one or more mutations, or polymorphisms that are amenable to direct genotyping by any of a variety of well known analysis methods, e.g., Southern blotting, RFLP, AFLP, SSCP, SNP, and the like.

A "diagnostic gene" is a gene whose expression may be detected by a diagnostic oligonucleotide or other method directed to detecting RNA or protein produced therefrom and such expression may be used to monitor transplant rejection or inflammation based disorders in a patient.

A "disease specific target oligonucleotide sequence" is a gene or other oligonucleotide that encodes a polypeptide, most typically a protein, or a subunit of a multi-subunit protein, that is a therapeutic target for a disease, or group of diseases.

The term "disease criterion" is used herein to designate an indicator of a disease, such as a diagnostic factor, a prognostic factor, a factor indicated by a medical or family history, a genetic factor, or a symptom, as well as an overt or confirmed diagnosis of a disease associated with several indicators such as those selected from the above list. A disease criterian includes data describing a patient's health status, including retrospective or prospective health data, e.g. in the form of the patient's medical history, laboratory test results, diagnostic test result, clinical events, medications, lists, response(s) to treatment and risk factors, etc.

The terms "molecular signature" or "expression profile" refers to the collection of expression values for a plurality (e.g., at least 2, but frequently about 10, about 100, about 1000, or more) of members of a library or set of diagnostic genes. In many cases, the molecular signature represents the expression pattern for all of the diagnostic genes in a library or array of potential diagnostic oligonucleotides or diagnostic oligonucleotides or diagnostic genes. Alternatively, the molecular signature represents the expression pattern for one or more subsets of the diagnostic gene library. The term "oligonucleotide" refers to two or more nucleotides. Nucleotides may be DNA or RNA, naturally occurring or synthetic.

The term "healthy individual," as used herein, is relative to a specified disease or disease criterion. That is, the individual does not exhibit the specified disease criterion or is not diagnosed with the specified disease. It will be understood, that the individual in question, can, of course, exhibit symptoms, or possess various indicator factors for another disease.

Similarly, an "individual diagnosed with a disease" refers to an individual diagnosed with a specified disease (or disease criterion). Such an individual may, or may not, also exhibit a disease criterion associated with, or be diagnosed with another (related or unrelated) disease.

An "array" is a spatially or logically organized collection, e.g., of oligonucleotide sequences or nucleotide sequence products such as RNA or proteins encoded by an oligonucleotide sequence. In some embodiments, an array includes antibodies or other binding reagents specific for products of a diagnostic gene library.

When referring to a pattern of expression, a "qualitative" difference in gene expression refers to a difference that is not assigned a relative value. That is, such a difference is designated by an "all or nothing" valuation. Such an all or nothing variation can be, for example, expression above or below a threshold of detection (an on/off pattern of expression). Alternatively, a qualitative difference can refer to expression of different types of expression products, e.g., different alleles (e.g., a mutant or polymorphic allele), variants (including sequence variants as well as post-translationally modified variants), etc.

In contrast, a "quantitative" difference, when referring to a pattern of gene expression, refers to a difference in expression that can be assigned a value on a graduated scale, (e.g., a 0-5 or 1-10 scale, a +−+++scale, a grade 1-grade 5 scale, or the like; it will be understood that the numbers selected for illustration are entirely arbitrary and in no-way are meant to be interpreted to limit the invention).

Gene Expression Systems of the Invention

The present invention is thus directed to a system for monitoring gene expression for diagnosing and monitoring inflammation disorders. Gene expression is monitored by detecting the expression levels of one or more nucleotide sequences. The present invention is directed to a system for monitoring gene expression in inflammation disorders in response to a particular drug treatment regimen. Particular genes of interest which find use in the system of the invention include those described in U.S. patent application Ser. Nos. 10/006,290; 10/131,827; 10/131,831; 10/511,937; 10/512,028; and 10/325,899 and those described herein. Any drug treatment may be monitored using the system and methods of the invention. Of particular interest are immunosuppressive drugs. Such immunosuppressive drugs may include steroids, cyclosporine, tacrolimus and other drugs.

Gene expression may be monitored using the system and methods of the invention to measure or determine the efficacy or effectiveness of a particular drug regimen. Gene expression monitoring may involve monitoring the expression of certain genes, certain sets of genes or genes involved in specific pathways. Such monitoring could be done in vivo through blood sampling of patients or in vitro through treatment of cells.

The system and methods of the invention find particular use in monitoring transplant rejection patients. In particular, the system and methods of the invention may be utilized to monitor the effects of immunosuppressive drugs on transplant patients. The methods find use in identifying specific genes, gene sets and pathways whose expression correlates with certain immunosuppressive drugs and levels of certain immunosuppressive drugs. Such genes are particularly useful in immunosuppressive drug monitoring.

The invention is directed to a gene expression system having at least one, at least two, at least three or four oligonucleotides wherein the at least one, at least two, at least three or four oligonucleotides has a nucleotide sequence which each detects the expression of a different one of the genes corresponding to SEQ ID NO:5, SEQ ID NO:11, SEQ ID NO:17, or SEQ ID NO:23. The gene expression systems may in addition include oligonucleotides which detect diagnostic genes other than the genes corresponding to SEQ ID NO:5, SEQ ID NO:11, SEQ ID NO:17, or SEQ. ID NO:23. In one format, the oligonucleotide detects expression of a gene that is differentially expressed in leukocytes. The gene expression system may be a diagnostic agent, a diagnostic oligonucleotide, a diagnostic oligonucleotide set or a diagnostic probe set. The oligonucleotide molecules may be genomic DNA, RNA, protein nucleic acid (PNA), cDNA or synthetic oligonucleotides. Following the procedures taught herein, one can identity sequences of interest for analyzing gene expression in leukocytes. Such sequences may be predictive of a disease state. Examples of additional diagnostic genes that may be used with the diagnostic genes of the present invention listed above include the genes referenced in U.S. patent application Ser. Nos. 10/006,290, 10/131,827, 10/131,831, and 10/328,899, and in PCT Application Nos: PCT/US03/13015 and PCT/US03/12946. All of the foregoing applications are hereby incorporated by reference in their entirety.

Diagnostic Oligonucleotides of the Invention

The invention relates to diagnostic oligonucleotides or diagnostic oligonucleotide set(s) including at least one oligonucleotide that detects the expression of one of the diagnostic genes that include the nucleotide sequence in SEQ ID NO:5, SEQ ID NO:11, SEQ ID NO:17, or SEQ ID NO:23, for which a correlation exists between the health status of an individual, the individual's expression of RNA or protein products corresponding to the nucleotide sequence, and the diagnosis and prognosis of transplant rejection, or is otherwise useful in monitoring an inflammation related disorder or condition. In some instances, only one oligonucleotide is necessary for such detection. Other members of a diagnostic oligonucleotide set may be identified by any means capable of detecting expression of RNA or protein products, including but not limited to differential expression screening, PCR, RT-PCR, SAGE analysis, high-throughput sequencing, microarrays, liquid or other arrays, protein-based methods (e.g., western blotting, proteomics, and other methods described herein), and data mining methods, as further described herein.

In one embodiment, a diagnostic oligonucleotide set include at least two, at least three or four oligonucleotides that each detects the expression of a different one of the diagnostic genes that include the nucleotide sequence in SEQ ID NO:5, SEQ ID NO:11, SEQ ID NO:17, or SEQ ID NO:23, which are differentially expressed in leukocytes in an individual with at least one disease criterion for at least one leukocyte-implicated disease relative to the expression in individual without the at least one disease criterion, wherein expression of the two or more nucleotide sequences is correlated with at least one disease criterion, as described below. In some embodiments, the diagnostic oligonucleotide set is immobilized on an array.

In another embodiment, diagnostic oligonucleotides (or oligonucleotide sets) are related to the diagnostic genes that include the nucleotide sequence in SEQ ID NO:5, SEQ ID NO:11, SEQ ID NO:17, or SEQ ID NO:23, for which a correlation exists between the health status, diagnosis and prognosis of transplant rejection (or disease criterion) of an individual. The diagnostic oligonucleotides are partially or totally contained in (or derived from) full-length transcript sequences (or predicted full-length transcript sequences both pre- and post-processing such as hnRNA and mRNA) for the diagnostic genes that include the nucleotide sequence in SEQ ID NO:5, SEQ ID NO:11, SEQ ID NO:17, or SEQ ID NO:23. In some cases, oligonucleotide sequences are designed from EST or Chromosomal sequences from a public database. In these cases the full-length gene sequences may not be known. Full-length sequences in these cases can be predicted using gene prediction algorithms. Alternatively the full-length can be determined by cloning and sequencing the full-length gene or genes that contain the sequence of interest using standard molecular biology approaches described here. The same is true for oligonucleotides designed from our sequencing of cDNA libraries where the cDNA does not match any sequence in the public databases.

The diagnostic oligonucleotides may also be derived from other genes that are coexpressed with the correlated sequence or full-length gene. Genes may share expression patterns because they are regulated in the same molecular pathway. Because of the similarity of expression behavior genes are identified as surrogates in that they can substitute for a diagnostic gene or a diagnostic gene in a diagnostic gene set.

As used herein the term "gene cluster" or "cluster" refers to a group of genes related by expression pattern. In other words, a cluster of genes is a group of genes with similar regulation across different conditions, such as graft non-rejection versus graft rejection or inflammation flare-up versus no flare-up. The expression profile for each gene in a cluster should be correlated with the expression profile of at least one other gene in that cluster. Correlation may be evaluated using a variety of statistical methods. As used herein the term "surrogate" refers to a gene with an expression profile such that it can substitute for a diagnostic gene in a diagnostic assay. Such genes are often members of the same gene cluster as the diagnostic gene. For each diagnostic gene or member of a diagnostic gene set, a set of potential surrogates can be identified through identification of genes with similar expression patterns as described below.

Many statistical analyses produce a correlation coefficient to describe the relatedness between two gene expression patterns. Patterns may be considered correlated if the correlation coefficient is greater than or equal to 0.5. In preferred embodiments, the correlation coefficient should be greater than 0.6, 0.7, 0.8, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Patterns may also be considered similar if they cluster closely upon hierarchical clustering of gene expression data (Eisen et al. 1998). Similar patterns may be those genes that are among the 1, 2, 5, 10, 20, 50 or 100 nearest neighbors in a hierarchical clustering or have a similarity score (Eisen et al. 1998) of >0.5, 0.7, 0.8, 0.9, 0.95 or 0.99. Similar patterns may also be identified as those genes found to be surrogates in a classification tree by CART (Breiman et al. 1994). Often, but not always, members of a gene cluster have similar biological functions in addition to similar gene expression patterns.

Correlated genes, clusters and surrogates are identified for the diagnostic genes of the invention. These surrogates may be used as diagnostic genes in an assay instead of, or in addition to, the diagnostic genes for which they are surrogates.

The invention also provides individual diagnostic probes or diagnostic probe sets. It is understood that a probe includes any reagent capable of specifically identifying a nucleotide sequence of the diagnostic gene or set of diagnostic genes, including but not limited to amplified DNA, amplified RNA, cDNA, synthetic oligonucleotide, partial or full-length nucleic acid sequences. In addition, the probe may identify the protein product of a diagnostic oligonucleotide sequence, including, for example, antibodies and other affinity reagents.

It is also understood that each probe can correspond to one gene, or multiple probes can correspond to one gene, or both, or one probe can correspond to more than one gene.

Homologs and variants of the disclosed nucleic acid molecules may be used in the present invention. Homologs and variants of these nucleic acid molecules will possess a relatively high degree of sequence identity when aligned using standard methods. The sequences encompassed by the invention have at least 40-50, 50-60, 70-80, 80-85, 85-90, 90-95 or 95-100% sequence identity to the sequences disclosed herein.

It is understood that for expression profiling, variations in the disclosed sequences will still permit detection of gene expression. The degree of sequence identity required to detect gene expression varies depending on the length of the oligomer. For a 60 mer, 6-8 random mutations or 6-8 random deletions in a 60 mer do not affect gene expression detection. Hughes, T R, et al. "Expression profiling using microarrays fabricated by an ink-jet oligonucleotide synthesizer. Nature Biotechnology, 19:343-347(2001). As the length of the DNA sequence is increased, the number of mutations or deletions permitted while still allowing gene expression detection is increased.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

The minimum length of an oligonucleotide probe necessary for specific hybridization in the human genome can be estimated using two approaches. The first method uses a statistical argument that the probe will be unique in the human genome by chance. Briefly, the number of independent perfect matches (Po) expected for an oligonucleotide of length L in a genome of complexity C can be calculated from the equation (Laird C D, Chromosoma 32:378 (1971):

$$Po=(1/4)^L*2C$$

In the case of mammalian genomes, $2C=\sim 3.6\times 10^9$, and an oligonucleotide of 14-15 nucleotides is expected to be represented only once in the genome. However, the distribution of nucleotides in the coding sequence of mammalian genomes is nonrandom (Lathe, R. J. Mol. Biol. 183:1 (1985) and longer oligonucleotides may be preferred in order to in increase the specificity of hybridization. In practical terms, this works out to probes that are 19-40 nucleotides long (Sambrook J et al., infra). The second method for estimating the length of a specific probe is to use a probe long enough to hybridize under the chosen conditions and use a computer to search for that sequence or close matches to the sequence in the human genome and choose a unique match. Probe sequences are chosen based on the desired hybridization properties as described in Chapter 11 of Sambrook et al, infra. The PRIMER3 program is useful for designing these probes (S. Rozen and H. Skaletsky 1996, 1997; Primer3 code is available on the web as open-source code. The sequences of these probes are then compared pair wise against a database of the human genome sequences using a program such as BLAST or MEGABLAST (Madden, T. L et al. (1996) Meth. Enzymol. 266:131-141). Since the entire human genome is now contained in the database, the number of matches will be determined. Probe sequences are chosen that are unique to the desired target sequence.

In some embodiments, a diagnostic probe or diagnostic probe set is immobilized on an array. The array is optionally includes one or more of: a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip.

In some embodiments, the leukocyte-implicated disease is selected from the diseases listed in Table 1. In other embodiments, the disease is atherosclerosis or cardiac allograft rejection. In other embodiments, the disease is congestive heart failure, angina, and myocardial infarction.

In some embodiments, one or more of the diagnostic oligonucleotides of the invention are used in combination with genes that are known to be associated with a disease state ("known markers") as a diagnostic gene set. The use of the diagnostic oligonucleotides in combination with the known markers can provide information that is not obtainable through the known markers alone. The known markers include those identified by the prior art listing provided.

General Molecular Biology References

In the context of the invention, nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Q-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomell et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563. Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company, The Great American Gene Company ExpressGen, Inc., Operon Technologies, Inc. and many others.

Similarly, commercial sources for nucleic acid and protein microarrays are available, and include, e.g., Agilent Technologies, Palo Alto, Calif. Affymetrix, Santa Clara, Calif.; and others.

One area of relevance to the present invention is hybridization of oligonucleotides. Those of skill in the art differentiate hybridization conditions based upon the stringency of hybridization. For example, highly stringent conditions could include hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3). Moderate stringency conditions could include, e.g., washing in 0.2×SSC/0.1% SDS at 42° C. (Ausubel et al., 1989, supra).

The invention also includes nucleic acid molecules, preferably DNA molecules, that hybridize to, and are therefore the complements of, the DNA sequences of the present invention. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target nucleotide sequence antisense molecules, useful, for example, in target nucleotide sequence regulation and/or as antisense primers in amplification reactions of target nucleotide sequence nucleic acid sequences. Further, such sequences may be used as part of ribozyme and/or triple helix sequences, also useful for target nucleotide sequence regulation. Still further, such molecules may be used as components of diagnostic methods whereby the presence of a disease-causing allele, may be detected.

Expression Profiling of Blood and Other bodily Fluid Samples

Leukocytes

The term leukocyte is used generically to refer to any nucleated blood cell that is not a nucleated erythrocyte. More specifically, leukocytes can be subdivided into two broad classes. The first class includes granulocytes, including, most prevalently, neutrophils, as well as eosinophils and basophils at low frequency. The second class, the non-granular or mononuclear leukocytes, includes monocytes and lymphocytes (e.g., T cells and B cells). There is an extensive literature in the art implicating leukocytes, e.g., neutrophils, monocytes and lymphocytes in a wide variety of disease processes, including inflammatory and rheumatic diseases, neurodegenerative diseases (such as Alzheimer's dementia), cardiovascular disease, endocrine diseases, transplant rejection, malignancy and infectious diseases, and other diseases listed in Table 1. Mononuclear cells are involved in the chronic immune response, while granulocytes, which make up approximately 60% of the leukocytes, have a non-specific and stereotyped response to acute inflammatory stimuli and often have a life span of only 24 hours.

In addition to their widespread involvement and/or implication in numerous disease related processes, leukocytes are particularly attractive substrates for clinical and experimental evaluation for a variety of reasons. Most importantly, they are readily accessible at low cost from essentially every potential subject. Collection is minimally invasive and associated with little pain, disability or recovery time. Collection can be performed by minimally trained personnel (e.g., phlebotomists, medical technicians, etc.) in a variety of clinical and non-clinical settings without significant technological expenditure. Additionally, leukocytes are renewable, and thus available at multiple time points for a single subject.

Detection of Non-Leukocyte Expressed Genes

When measuring gene expression levels in a blood sample, RNAs may be measured that are not derived from leukocytes. Examples are viral genes, free RNAs that have been released from damaged non-leukocyte cell types or RNA from circulating non-leukocyte cell types. For example, in the process of acute allograft rejection, tissue damage may result in release of allograft cells or RNAs derived from allograft cells into the circulation. In the case of cardiac allografts, such transcripts may be specific to muscle (myoglobin) or to cardiac muscle (Troponin I, Toponin T, CK-MB). Presence of cardiac specific mRNAs in peripheral blood may indicate ongoing or recent cardiac cellular damage (resulting from acute rejection). Therefore, such genes may be excellent diagnostic markers for allograft rejection.

Identification of the Diagnostic Oligonucleotide (Sets) of the Invention

The diagnostic oligonucleotides and probes that detect one or more of the four diagnostic genes of the present invention may be used in conjunction with the diagnostic oligonucleotides and priobes that detect other diagnostic genes. In general, one of skill in the art would be able to identify such additional diagnostic genes by referring to published literature and by identifying and validating new diagnostic genes. Many methods are available such as expression profiling of patients with one of the disorders in Table 1. U.S. patent application Ser. No. 10/006,290 discloses extensive methods for expression profiling (such methods are herein incorporated by reference in their entirety)

Identification of diagnostic oligonucleotides and diagnostic oligonucleotide sets and disease specific target nucleotide sequence proceeds by correlating the leukocyte expression profiles with data regarding the subject's health status to produce a data set designated a "molecular signature." Examples of data regarding a patient's health status, also termed "disease criteria(ion)", is described below and in the Section titled "selected diseases," below. Methods useful for correlation analysis are well known in the art.

Generally, relevant data regarding the subject's health status includes retrospective or prospective health data, e.g., in the form of the subject's medical history, as provided by the subject, physician or third party, such as, medical diagnoses, laboratory test results, diagnostic test results, clinical events, or medication lists, as further described below. Such data may include information regarding a patient's response to treatment and/or a particular medication and data regarding the presence of previously characterized "risk factors." For example, cigarette smoking and obesity are previously identified risk factors for heart disease. Further examples of health status information, including diseases and disease criteria, is described in the section titled Selected diseases, below.

Typically, the data describes prior events and evaluations (i.e., retrospective data). However, it is envisioned that data collected subsequent to the sampling (i.e., prospective data) can also be correlated with the expression profile. The tissue sampled, e.g., peripheral blood, bronchial lavage, etc., can be obtained at one or more multiple time points and subject data is considered retrospective or prospective with respect to the time of sample procurement.

Data collected at multiple time points, called "longitudinal data", is often useful, and thus, the invention encompasses the analysis of patient data collected from the same patient at different time points. Analysis of paired samples, such as samples from a patient at different times, allows identification of differences that are specifically related to the disease state since the genetic variability specific to the patient is controlled for by the comparison. Additionally, other variables that exist between patients may be controlled for in this way, for example, the presence or absence of inflammatory diseases (e.g., rheumatoid arthritis) the use of medications that may effect leukocyte gene expression, the presence or absence of co-morbid conditions, etc. Methods for analysis of paired samples are further described below. Moreover, the analysis of a pattern of expression profiles (generated by collecting multiple expression profiles) provides information relating to changes in expression level over time, and may permit the determination of a rate of change, a trajectory, or an expression curve. Two longitudinal samples may provide information on the change in expression of a gene over time, while three longitudinal samples may be necessary to determine the "trajectory" of expression of a gene. Such information may be relevant to the diagnosis of a disease. For example, the expression of a gene may vary from individual to individual, but a clinical event, for example, a heart attack, may cause the level of expression to double in each patient. In this example, clinically interesting information is gleaned from the change in expression level, as opposed to the absolute level of expression in each individual.

When a single patient sample is obtained, it may still be desirable to compare the expression profile of that sample to some reference expression profile. In this case, one can determine the change of expression between the patient's sample and a reference expression profile that is appropriate for that patient and the medical condition in question. For example, a reference expression profile can be determined for all patients without the disease criterion in question who have similar characteristics, such as age, sex, race, diagnoses etc.

Diagnostic Classification

Once a discriminating set of genes is identified, the diagnostic classifier (a mathematical function that assigns samples to diagnostic categories based on expression data) is applied to unknown sample expression levels.

Methods that can be used for this analysis include the following non-limiting list:

CLEAVER is an algorithm used for classification of useful expression profile data. See Raychaudhuri et al. (2001) *Trends Biotechnol* 19:189-193. CLEAVER uses positive training samples (e.g., expression profiles from samples known to be derived from a particular patient or sample diagnostic category, disease or disease criteria), negative training samples (e.g., expression profiles from samples known not to be derived from a particular patient or sample diagnostic category, disease or disease criteria) and test samples (e.g., expression profiles obtained from a patient), and determines whether the test sample correlates with the particular disease or disease criteria, or does not correlate with a particular disease or disease criteria. CLEAVER also generates a list of the 20 most predictive genes for classification.

Artificial neural networks (hereinafter, "ANN") can be used to recognize patterns in complex data sets and can discover expression criteria that classify samples into more than 2 groups. The use of artificial neural networks for discovery of gene expression diagnostics for cancers using expression data generated by oligonucleotide expression microarrays is demonstrated by Khan et al. (2001) *Nature Med.* 7:673-9. Khan found that 96 genes provided 0% error rate in classification of the tumors. The most important of these genes for classification was then determined by measuring the sensitivity of the classification to a change in expression of each gene. Hierarchical clustering using the 96 genes results in correct grouping of the cancers into diagnostic categories.

Golub uses cDNA microarrays and a distinction calculation to identify genes with expression behavior that distinguishes myeloid and lymphoid leukemias. See Golub et al. (1999) *Science* 286:531-7. Self organizing maps were used for new class discovery. Cross validation was done with a "leave one out" analysis. 50 genes were identified as useful markers. This was reduced to as few as 10 genes with equivalent diagnostic accuracy.

Hierarchical and non-hierarchical clustering methods are also useful for identifying groups of genes that correlate with a subset of clinical samples such as with transplant rejection grade. Alizadeh used hierarchical clustering as the primary tool to distinguish different types of diffuse B-cell lymphomas based on gene expression profile data. See Alizadeh et al. (2000) *Nature* 403:503-11. Alizadeh used hierarchical clustering as the primary tool to distinguish different types of diffuse B-cell lymphomas based on gene expression profile data. A cDNA array carrying 17856 probes was used for these experiments, 96 samples were assessed on 128 arrays, and a set of 380 genes was identified as being useful for sample classification.

Perou demonstrates the use of hierarchical clustering for the molecular classification of breast tumor samples based on expression profile data. See Perou el al. (2000) *Nature* 406: 747-52. In this work, a cDNA array carrying 8102 gene probes was used. 1753 of these genes were found to have high variation between breast tumors and were used for the analysis.

Hastie describes the use of gene shaving for discovery of expression markers. Hastie et al. (2000) *Genome Biol.* 1(2): RESEARCH 0003.1-0003.21. The gene shaving algorithm identifies sets of genes with similar or coherent expression patterns, but large variation across conditions (RNA samples, sample classes, patient classes). In this manner, genes with a tight expression pattern within a transplant rejection grade, but also with high variability across rejection grades are grouped together. The algorithm takes advantage of both characteristics in one grouping step. For example, gene shaving can identify useful marker genes with co-regulated expression. Sets of useful marker genes can be reduced to a smaller set, with each gene providing some non-redundant value in classification. This algorithm was used on the data set described in Alizadeh et al., supra, and the set of 380 informative gene markers was reduced to 234.

Supervised harvesting of expression trees (Hastie 2001) identifies genes or clusters that best distinguish one class from all the others on the data set. The method is used to identify the genes/clusters that can best separate one class versus all the others for datasets that include two or more classes or all classes from each other. This algorithm can be used for discovery or testing of a diagnostic gene set.

CART is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. CART identifies surrogates for each splitter (genes that are the next best substitute for a useful gene in classification.

Multiple Additive Regression Trees (Friedman, J H 1999, MART) is similar to CART in that it is a classification algorithm that builds decision trees to distinguish groups. MART builds numerous trees for any classification problem and the resulting model involves a combination of the multiple trees. MART can select variables as it build models and thus can be used on large data sets, such as those derived from an 8000 gene microarray. Because MART uses a combination of many trees and does not take too much information from any one tree, it resists over training. MART identifies a set of genes and an algorithm for their use as a classifier.

A Nearest Shrunken Centroids Classifier can be applied to microarray or other data sets by the methods described by Tibshirani et al. 2002. This algorithm also identified gene sets for classification and determines their 10 fold cross validation error rates for each class of samples. The algorithm determines the error rates for models of any size, from one gene to all genes in the set. The error rates for either or both sample classes can be minimized when a particular number of genes are used. When this gene number is determined, the algorithm associated with the selected genes can be identified and employed as a classifier on prospective sample.

Once a set of genes and expression criteria for those genes have been established for classification, cross validation is done. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples.

Clinical data are gathered for every patient sample used for expression analysis. Clinical variables can be quantitative or non-quantitative. A clinical variable that is quantitative can be used as a variable for significance or classification analysis. Non-quantitative clinical variables, such as the sex of the patient, can also be used in a significance analysis or classification analysis with some statistical tool. It is appreciated that the most useful diagnostic gene set for a condition may be optimal when considered along with one or more predictive clinical variables. Clinical data can also be used as supervising vectors for a correlation analysis. That is to say that the clinical data associated with each sample can be used to divide the samples into meaningful diagnostic categories for analysis. For example, samples can be divided into 2 or more groups based on the presence or absence of some diagnostic criterion (a). In addition, clinical data can be utilized to select patients for a correlation analysis or to exclude them based on some undesirable characteristic, such as an ongoing infection, a medicine or some other issue. Clinical data can also be used to assess the pre-test probability of an outcome. For example, patients who are female are much more likely to be diagnosed as having systemic lupus erythematosis than patients who are male.

Once a set of genes are identified that classify samples with acceptable accuracy, these genes are validated as a set using new samples that were not used to discover the gene set. These samples can be taken from frozen archives from the discovery clinical study or can be taken from new patients prospectively. Validation using a "test set" of samples can be done using expression profiling of the gene set with microarrays or using real-time PCR for each gene on the test set samples. Alternatively, a different expression profiling technology can be used.

Immune Monitoring

Leukocyte gene expression can be used to monitor the immune system. Immune monitoring examines both the level of gene expression for an individual gene or a set of genes in a given cell type and for a gene or genes which are expressed in a cell type selective manner. Gene expression monitoring will also detect the presence or absence of new cell types, progenitor cells, differentiation of cells and the like. Gene expression patterns may be associated with activation or the resting state of cells of the immune system that are responsible for or responsive to a disease state. For example, in the process of transplant rejection, cells of the immune system are activated by the presence of the foreign tissue. Genes and gene sets that monitor and diagnose this process are providing a measure of the level and type of activation of the immune system. Genes and gene sets that are useful in monitoring the immune system may be useful for diagnosis and monitoring of all diseases that involve the immune system. Some examples are transplant rejection, rheumatoid arthritis, lupus, inflammatory bowel diseases, multiple sclerosis, HIV/AIDS, and viral, bacterial and fungal infection. All disorders and diseases disclosed herein are contemplated. Genes and gene sets that monitor immune activation are useful for monitoring response to immunosuppressive drug therapy, which is used to decrease immune activation. Genes are found to correlate with immune activation by correlation of expression patterns to the known presence of immune activation or quiescence in a sample as determined by some other test.

Selected Diseases

In principle, individual diagnostic oligonucleotides and diagnostic oligonucleotide sets of the invention may be developed and applied to essentially any disease, or disease criterion, as long as at least one nucleotide sequence or subset of nucleotide sequences is differentially expressed in samples derived from one or more individuals with a disease criteria or disease and one or more individuals without the disease criteria or disease, wherein the individual may be the same individual sampled at different points in time, or the individuals may be different individuals (or populations of individuals). For example, the nucleotide sequence or subset of nucleotide sequences may be differentially expressed in the sampled tissues of subjects with the disease or disease criterion (e.g., a patient with a disease or disease criteria) as compared to subjects without the disease or disease criterion (e.g., patients without a disease (control patients)). Alternatively, or in addition, the subset of nucleotide sequence(s) may be differentially expressed in different samples taken from the same patient, e.g at different points in time, at different disease stages, before and after a treatment, in the presence or absence of a risk factor, etc.

Expression profiles corresponding to individual nucleotide sequences or sets of nucleotide sequences that correlate not with a diagnosis, but rather with a particular aspect of a disease can also be used to identify the individual diagnostic oligonucleotides, diagnostic oligonucleotide sets and disease specific target nucleotide sequences of the invention. For example, such an aspect, or disease criterion, can relate to a subject's medical or family history, e.g., childhood illness, cause of death of a parent or other relative, prior surgery or other intervention, medications, symptoms (including onset and/or duration of symptoms), etc. Alternatively, the disease criterion can relate to a diagnosis, e.g., hypertension, diabetes, atherosclerosis, or prognosis (e.g., prediction of future diagnoses, events or complications), e.g., acute myocardial infarction, restenosis following angioplasty, reperfusion injury, allograft rejection, rheumatoid arthritis or systemic lupus erythematosis disease activity or the like. In other cases, the disease criterion corresponds to a therapeutic outcome, e.g., transplant rejection, bypass surgery or response to a medication, restenosis after stent implantation, collateral vessel growth due to therapeutic angiogenesis therapy, decreased angina due to revascularization, resolution of symptoms associated with a myriad of therapies, and the like. Alternatively, the disease criteria correspond with previously identified or classic risk factors and may correspond to prognosis or future disease diagnosis. As indicated above, a disease criterion can also correspond to genotype for one or more loci. Disease criteria (including patient data) may be collected (and compared) from the same patient at different points in time, from different patients, between patients with a disease (criterion) and patients representing a control population, etc. Longitudinal data, i.e., data collected at different time points from an individual (or group of individuals) may be used for comparisons of samples obtained from an individual (group of individuals) at different points in time, to permit identification of differences specifically related to the disease state, and to obtain information relating to the change in expression over time, including a rate of change or trajectory of expression over time. The usefulness of longitudinal data is further discussed in the section titled "Identification of diagnostic oligonucleotide sets of the invention".

It is further understood that individual diagnostic oligonucleotides and diagnostic oligonucleotide sets may be identified and developed for use in diagnosing conditions for which there is no present means of diagnosis. For example, in rheumatoid arthritis, joint destruction is often well under way before a patient experience symptoms of the condition. An individual diagnostic oligonucleotides or diagnostic oligonucleotide set may be developed that diagnoses rheumatic joint destruction at an earlier stage than would be possible using present means of diagnosis, which rely in part on the presentation of symptoms by a patient. Individual diagnostic oligonucleotides and diagnostic oligonucleotide sets may also be developed to replace or augment current diagnostic procedures. For example, the use of an individual diagnostic oligonucleotide or diagnostic oligonucleotide set to diagnose cardiac allograft rejection may replace the current diagnostic test, a graft biopsy.

It is understood that the following discussion of diseases is exemplary and non-limiting, and further that the general criteria discussed above, e.g. use of family medical history, are generally applicable to the specific diseases discussed below.

In addition to leukocytes, as described throughout, the general method is applicable to nucleotide sequences that are differentially expressed in any subject tissue or cell type, by the collection and assessment of samples of that tissue or cell type. However, in many cases, collection of such samples presents significant technical or medical problems given the current state of the art.

Organ Transplant Rejection and Success

A frequent complication of organ transplantation is recognition of the transplanted organ as foreign by the immune system resulting in rejection. Individual diagnostic oligonucleotides or diagnostic oligonucleotide sets can be identified and validated for monitoring organ transplant success, rejection and treatment. Medications currently exist that suppress the immune system, and thereby decrease the rate of and severity of rejection. However, these drugs also suppress the physiologic immune responses, leaving the patient susceptible to a wide variety of opportunistic infections and cancers. At present there is no easy, reliable way to diagnose transplant rejection. Organ biopsy is the preferred method, but this is expensive, painful and associated with significant risk and has inadequate sensitivity for focal rejection.

Individual diagnostic oligonucleotides and diagnostic oligonucleotide sets of the present invention can be developed and validated for use as diagnostic tests for transplant rejection and success. It is appreciated that the methods of identifying individual diagnostic oligonucleotides and diagnostic oligonucleotide sets are applicable to any organ transplant population. For example, individual diagnostic oligonucleotides and diagnostic oligonucleotide sets are developed for cardiac allograft rejection and success.

In some cases, disease criteria correspond to acute stage rejection diagnosis based on organ biopsy and graded using the International Society for Heart and Lung Transplantation ("ISHLT") criteria. This grading system classifies endomyocardial biopsies on the histological level as Grade 0, 1A, 1B, 2, 3A, 3B, or 4. Grade 0 biopsies have no evidence of rejection, while each successive grade has increased severity of leukocyte infiltration and/or damage to the graft myocardial cells. It is appreciated that there is variability in the Grading systems between medical centers and pathologists and between repeated readings of the same pathologist at different times. When using the biopsy grade as a disease criterion for leukocyte gene expression correlation analysis, it may be desirable to have a single pathologist read all biopsy slides or have multiple pathologists read all slides to determine the variability in this disease criterion. It is also appreciated that cardiac biopsy, in part due to variability, is not 100% sensitive or 100% specific for diagnosing acute rejection. When using the cardiac biopsy grade as a disease criterion for the discovery of diagnostic genes and gene sets, it may be desirable to divide patient samples into diagnostic categories based on the grades. Examples of such classes are those patients with: Grade 0 vs. Grades 1A-4, Grade 0 vs. Grades 1B-4, Grade 0 vs. Grades 2-4, Grade 0-1 vs. Grade 2-4, Grade 0-1 vs. Grade 3A-4, or Grade 0 vs. Grade 3A-4.

Other disease criteria correspond to the cardiac biopsy results and other criteria, such as the results of cardiac function testing by echocardiography, hemodynamics assessment by cardiac catheterization, CMV infection, weeks post transplant, medication regimen, demographics and/or results of other diagnostic tests.

Other disease criteria correspond to information from the patient's medical history and information regarding the organ donor. Alternatively, disease criteria include the presence or absence of cytomegalovirus (CMV) infection, Epstein-Barr virus (EBV) infection, allograft dysfunction measured by physiological tests of cardiac function (e.g., hemodynamic measurements from catheterization or echocardiograph data), and symptoms of other infections. Alternatively, disease criteria correspond to therapeutic outcome, e.g. graft failure, re-transplantation, death, hospitalization, need for intravenous immunosuppression, transplant vasculopathy, response to immunosuppressive medications, etc. Disease criteria may further correspond to a rejection episode of at least moderate histologic grade, which results in treatment of the patient with additional corticosteroids, anti-T cell antibodies, or total lymphoid irradiation; a rejection with histologic grade 2 or higher; a rejection with histologic grade<2; the absence of histologic rejection and normal or unchanged allograft function (based on hemodynamic measurements from catheterization or on echocardiographic data); the presence of severe allograft dysfunction or worsening allograft dysfunction during the study period (based on hemodynamic measurements from catheterization or on echocardiographic data); documented CMV infection by culture, histology, or PCR, and at least one clinical sign or symptom of infection; specific graft biopsy rejection grades; rejection of mild to moderate histologic severity prompting augmentation of the patient's chronic immunosuppressive regimen; rejection of mild to moderate severity with allograft dysfunction prompting plasmaphoresis or a diagnosis of "humoral" rejection; infections other than CMV, especially infection with Epstein Barr virus (EBV); lymphoproliferative disorder (also called post-transplant lymphoma); transplant vasculopathy diagnosed by increased intimal thickness on intravascular ultrasound (IVUS), angiography, or acute myocardial infarction; graft failure or retransplantation; and all cause mortality.

In another example, individual diagnostic oligonucleotides and diagnostic oligonucleotide sets are developed and validated for use in diagnosis and monitoring of kidney allograft recipients. Rejection criteria correspond to, e.g., results of biopsy analysis for kidney allograft rejection, serum creatine level, creatinine clearance, radiological imaging results for the kidney and urinalysis results. Another rejection criterion corresponds to the need for hemodialysis, retransplantation, death or other renal replacement therapy. Individual diagnostic oligonucleotides and diagnostic oligonucleotide sets are developed and validated for use in diagnosis and treatment of bone marrow transplant and liver transplantation pateints, respectively. Rejection criteria for bone marrow transplant correspond to the diagnosis and monitoring of graft rejection and/or graft versus host disease, the recurrence of cancer, complications due to immunosuppression, hematologic abnormalities, infection, hospitalization and/or death. Rejection criteria for liver transplant rejection include levels of serum markers for liver damage and liver function such as AST (aspartate aminotransferase), ALT (alanine aminotransferase), Alkaline phosphatase, GGT, (gamma-glutamyl transpeptidase) Bilirubin, Albumin and Prothrombin time. Further rejection criteria correspond to hepatic encephalopathy, medication usage, ascites, graft failure, retransplantation, hospitalization, complications of immunosuppression, results of diagnostic tests, results of radiological testing, death and histological rejection on graft biopsy. In addition, urine can be utilized for at the target tissue for profiling in renal transplant, while biliary and intestinal secretions and feces may be used favorably for hepatic or intestinal organ allograft rejection. Individual diagnostic oligonucleotides and diagnostic nucleotide sets can also be discovered and developed for the diagnosis and monitoring of chronic renal allograft rejection.

In the case of renal allografts, gene expression markers may be identified that are secreted proteins. These proteins may be detected in the urine of allograft recipients using standard immunoassays. Proteins are more likely to be present in the urine if they are of low molecular weight. Lower molecular weight proteins are more likely to pass through the glomerular membrane and into the urine.

In another example, individual diagnostic oligonucleotides and diagnostic oligonucleotide sets are developed and validated for use in diagnosis and treatment of xenograft recipients. This can include the transplantation of any organ from a non-human animal to a human or between non-human animals. Considerations for discovery and application of diagnostics and therapeutics and for rejection criterion are substantially similar to those for allograft transplantation between humans.

In another example, individual diagnostic oligonucleotides and diagnostic oligonucleotide sets are developed and validated for use in diagnosis and treatment of artificial organ recipients. This includes, but is not limited to mechanical circulatory support, artificial hearts, left ventricular assist devices, renal replacement therapies, organ prostheses and the like. Rejection criteria are thrombosis (blood clots), infection, death, hospitalization, and worsening measures of organ function (e.g., hemodynamics, creatinine, liver function testing, renal function testing, functional capacity).

In another example, individual diagnostic oligonucleotides and diagnostic oligonucleotide sets are developed and validated for use in matching donor organs to appropriate recipients. Individual diagnostic oligonucleotides and diagnostic gene sets can be discovered that correlate with successful matching of donor organ to recipient. Rejection criteria include graft failure, acute and chronic rejection, death, hospitalization, immunosuppressive drug use, and complications of immunosuppression. Genes and gene sets may be assayed from the donor or recipient's peripheral blood, organ tissue or some other tissue.

In another example, individual diagnostic oligonucleotides and diagnostic oligonucleotide sets are developed and validated for use in diagnosis and induction of patient immune tolerance (decrease rejection of an allograft by the host immune system). Rejection criteria include actual rejection, assays of immune activation, need for immunosuppression and all rejection criteria noted above for transplantation of each organ.

Pharmacogenomics

Pharmacogenomics is the study of the individual propensity to respond to a particular drug therapy (combination of therapies). In this context, response can mean whether a particular drug will work on a particular patient, e.g. some patients respond to one drug but not to another drug. Response can also refer to the likelihood of successful treatment or the assessment of progress in treatment. Titration of drug therapy to a particular patient is also included in this description, e.g. different patients can respond to different doses of a given medication. This aspect may be important when drugs with side-effects or interactions with other drug therapies are contemplated.

Transplant recipients often undergo immunosuppressive drug therapy to decrease the likelihood of rejection. Conventional approaches use serum drug levels to monitor drug therapy, but often the drug level does not correlate with the efficacy of immunosuppression. Therefore, alternative methods of monitoring are needed. Gene expression may be monitored using the system and methods of the invention to measure or determine the efficacy or effectiveness of a particular drug regimen. For example, Table 2 shows that high levels of cyclosporine correlate to the downregulation of genes involved in cytotoxicity and cell surface mediation. The genes listed in this table, KLRF1, Perforin 1L, KLRC1, GZMB, FCGR3A, CD47, and FCGR3B, some or all of which are described in are described in U.S. patent application Ser. Nos. 10/006,290; 10/131,827; 10/131,831; 10/511,937; 10/512,028 and 10/325,899.

TABLE 2

| Pathway | Gene | Function | Change in Expression | p-value |
|---------|------|----------|---------------------|---------|
| Cytotoxic T-cell and NK Activity | KLRF1 | Killer Cell Receptor F | ↓ | 0.002 |
| | Perforin1L | Perforin | ↓ | 0.009 |
| | KLRC1 | Killer Cell Receptor C | ↓ | 0.015 |
| | GZMB | Granzyme B | ↓ | 0.045 |
| Cell surface | FCGR3A | CD16 Receptor | ↓ | 0.007 |
| Immune Modulators | CD47 | Integrin Signal Transducer | ↓ | 0.009 |
| | FCGR3B | CD 16 Receptor | ↓ | 0.016 |

Individual diagnostic oligonucleotides and diagnostic oligonucleotide sets are developed and validated for use in assessing whether a patient will respond to a particular therapy and/or monitoring response of a patient to drug therapy (therapies). Rejection, inflammation or disease criteria correspond to presence or absence of clinical symptoms or clinical endpoints, presence of side-effects or interaction with other drug(s). The individual diagnostic oligonucleotides and diagnostic oligonucleotide set may further comprise nucleotide sequences that are targets of drug treatment or markers of active rejection, inflammation or disease.

Validation and Accuracy of Diagnostic Oligonucleotide Sets

Prior to widespread application of the diagnostic probes and probe sets of the invention the predictive value of the probe or probe set is validated. Example 1 demonstrates the validation of the diagnostic probes to the four diagnostic genes of the present invention. When the diagnostic probe or probe set is discovered by microarray based expression analysis, the differential expression of the gene or member genes may be validated by a less variable and more quantitive and accurate technology such as real time PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T = C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethidium bromide or other DNA-binding dyes and many modifications of the fluorescent dye/quencher dye Taqman chemistry, for example scorpions.

Real-time PCR validation can be done as described in Example 7.

Typically, the oligonucleotide sequence of each probe is confirmed, e.g. by DNA sequencing using an oligonucleotide-specific primer. Partial sequence obtained is generally sufficient to confirm the identity of the oligonucleotide probe. Alternatively, a complementary polynucleotide is fluorescently labeled and hybridized to the array, or to a different array containing a resynthesized version of the oligo nucleotide probe, and detection of the correct probe is confirmed.

Typically, validation is performed by statistically evaluating the accuracy of the correspondence between the molecular signature for a diagnostic probe or probe set and a selected indicator. For example, the expression differential for a nucleotide sequence between two subject classes can be expressed as a simple ratio of relative expression. The expression of the nucleotide sequence in subjects with selected indicator can be compared to the expression of that nucleotide sequence in subjects without the indicator, as described in the following equations.

$$\Sigma E_x ai/N = E_x A \text{ the average expression of nucleotide sequence } x \text{ in the members of group } A;$$

$$\Sigma E_x bi/M = E_x B \text{ the average expression of nucleotide sequence } x \text{ in the members of group } B;$$

$$E_x A/ExB = \Delta E_x AB \text{ the average differential expression of nucleotide sequence } x \text{ between groups } A \text{ and } B;$$

where $\Sigma$ indicates a sum; Ex is the expression of nucleotide sequence x relative to a standard; ai are the individual members of group A, group A has N members; bi are the individual members of group B, group B has M members.

The expression of at least two nucleotide sequences, e.g., nucleotide sequence X and nucleotide sequence Y are measured relative to a standard in at least one subject of group A (e.g., with a disease or inflammation related disorder) and group B (e.g., without the disease or inflammation related disorder). Ideally, for purposes of validation the indicator is independent from (i.e., not assigned based upon) the expression pattern. Alternatively, a minimum threshold of gene expression for nucleotide sequences X and Y, relative to the standard, are designated for assignment to group A. For nucleotide sequence x, this threshold is designated $\Delta Ex$, and for nucleotide sequence y, the threshold is designated $\Delta Ey$.

The following formulas are used in the calculations below:

Sensitivity=(true positives/true positives+false negatives)

Specificity=(true negatives/true negatives+false positives)

If, for example, expression of nucleotide sequence x above a threshold: $x > \Delta Ex$, is observed for 80/100 subjects in group A and for 10/100 subjects in group B, the sensitivity of nucleotide sequence x for the assignment to group A, at the given expression threshold $\Delta Ex$, is 80%, and the specificity is 90%.

If the expression of nucleotide sequence y is $> \Delta Ey$ in 80/100 subjects in group A, and in 10/100 subjects in group B, then, similarly the sensitivity of nucleotide sequence y for the assignment to group A at the given threshold $\Delta Ey$ is 80% and the specificity is 90%. If in addition, 60 of the 80 subjects in group A that meet the expression threshold for nucleotide sequence y also meet the expression threshold $\Delta Ex$ and that 5 of the 10 subjects in group B that meet the expression threshold for nucleotide sequence y also meet the expression threshold $\Delta Ex$, the sensitivity of the test (x>$\Delta Ex$ and y>$\Delta Ey$) for assignment of subjects to group A is 60% and the specificity is 95%.

Alternatively, if the criteria for assignment to group A are change to: Expression of x>$\Delta Ex$ or expression of y>$\Delta Ey$, the sensitivity approaches 100% and the specificity is 85%.

Clearly, the predictive accuracy of any diagnostic probe or probe set is dependent on the minimum expression threshold selected. The expression of nucleotide sequence X (relative to a standard) is measured in subjects of groups A (with disease or inflammation related disorder) and B (without disease or inflammation related disorder). The minimum threshold of nucleotide sequence expression for x, required for assignment to group A is designated $\Delta Ex$ 1.

If 90/100 patients in group A have expression of nucleotide sequence x>$\Delta Ex$ 1 and 20/100 patients in group B have expression of nucleotide sequence x>$\Delta Ex$ 1, then the sensitivity of the expression of nucleotide sequence x (using $\Delta Ex$ 1 as a minimum expression threshold) for assignment of patients to group A will be 90% and the specificity will be 80%.

Altering the minimum expression threshold results in an alteration in the specificity and sensitivity of the nucleotide sequences in question. For example, if the minimum expression threshold of nucleotide sequence x for assignment of subjects to group A is lowered to $\Delta Ex$ 2, such that 100/100 subjects in group A and 40/100 subjects in group B meet the threshold, then the sensitivity of the test for assignment of subjects to group A will be 100% and the specificity will be 60%.

Thus, for 2 nucleotide sequences X and Y: the expression of nucleotide sequence x and nucleotide sequence y (relative to a standard) are measured in subjects belonging to groups A (with disease or inflammation related disorder) and B (without disease or inflammation related disorder). Minimum thresholds of nucleotide sequence expression for nucleotide sequences X and Y (relative to common standards) are designated for assignment to group A. For nucleotide sequence x, this threshold is designated $\Delta Ex$ 1 and for nucleotide sequence y, this threshold is designated $\Delta Ey1$.

If in group A, 90/100 patients meet the minimum requirements of expression $\Delta Ex1$ and $\Delta Ey1$, and in group B, 10/100 subjects meet the minimum requirements of expression $\Delta Ex1$ and $\Delta Ey1$, then the sensitivity of the test for assignment of subjects to group A is 90% and the specificity is 90%.

Increasing the minimum expression thresholds for X and Y to $\Delta Ex2$ and $\Delta Ey2$, such that in group A, 70/100 subjects meet the minimum requirements of expression $\Delta Ex2$ and $\Delta Ey2$, and in group B, 3/100 subjects meet the minimum requirements of expression $\Delta Ex2$ and $\Delta Ey2$. Now the sensitivity of the test for assignment of subjects to group A is 70% and the specificity is 97%.

If the criteria for assignment to group A is that the subject in question meets either threshold, $\Delta Ex2$ or $\Delta Ey2$, and it is found that 100/100 subjects in group A meet the criteria and 20/100 subjects in group B meet the criteria, then the sensitivity of the test for assignment to group A is 100% and the specificity is 80%.

Individual components of a diagnostic probe or probe set each have a defined sensitivity and specificity for distinguishing between subject groups. Such individual nucleotide sequences can be employed in concert as a diagnostic probe set to increase the sensitivity and specificity of the evaluation. The database of molecular signatures is queried by algorithms to identify the set of nucleotide sequences (i.e., corresponding to members of the probe set) with the highest average differential expression between subject groups. Typically, as the number of nucleotide sequences in the diagnostic probe set increases, so does the predictive value, that is, the sensitivity and specificity of the probe set. When the probe sets are defined they may be used for diagnosis and patient monitoring as discussed below. The diagnostic sensitivity and specificity of the probe sets for the defined use can be determined for a given probe set with specified expression levels as demonstrated above. By altering the expression threshold required for the use of each nucleotide sequence as a diagnostic, the sensitivity and specificity of the probe set can be altered by the practitioner. For example, by lowering the magnitude of the expression differential threshold for each nucleotide sequence in the set, the sensitivity of the test will increase, but the specificity will decrease. As is apparent from the foregoing discussion, sensitivity and specificity are inversely related and the predictive accuracy of the probe set is continuous and dependent on the expression threshold set for each nucleotide sequence. Although sensitivity and specificity tend to have an inverse relationship when expression thresholds are altered, both parameters can be increased as nucleotide sequences with predictive value are added to the diagnostic oligonucleotide set. In addition a single or a few markers may not be reliable expression markers across a population of patients. This is because of the variability in expression and measurement of expression that exists between measurements, individuals and individuals over time. Inclusion of a large number of nucleotide sequences or large numbers of nucleotide sequences in a diagnostic oligonucleotide set allows for this variability as not all nucleotide sequences need to meet a threshold for diagnosis. Generally, more markers are better than a single marker. If many markers are used to make a diagnosis, the likelihood that all expression markers will not meet some thresholds based upon random variability is low and thus the test will give fewer false negatives.

It is appreciated that the desired diagnostic sensitivity and specificity of the individual diagnostic oligonucleotide or diagnostic oligonucleotide set may vary depending on the intended use of the probe or probe set. For example, in certain uses, high specificity and high sensitivity are desired. For example, an individual diagnostic oligonucleotide or a diagnostic oligonucleotide set for predicting which patient population may experience side effects may require high sensitivity so as to avoid treating such patients. In other settings, high sensitivity is desired, while reduced specificity may be tolerated. For example, in the case of a beneficial treatment with few side effects, it may be important to identify as many patients as possible (high sensitivity) who will respond to the drug, and treatment of some patients who will not respond is tolerated. In other settings, high specificity is desired and reduced sensitivity may be tolerated. For example, when identifying patients for an early-phase clinical trial, it is important to identify patients who may respond to the particular treatment. Lower sensitivity is tolerated in this setting as it merely results in reduced patients who enroll in the study or requires that more patients are screened for enrollment.

Methods of Using Diagnostic Oligonucleotide (Sets)

The invention also provide methods of using the diagnostic oligonucleotides and diagnostic oligonucleotide sets to: diagnose or monitor disease or inflammation related disorder; assess severity of disease or inflammation related disorder; predict future occurrence of disease or inflammation related disorder; predict future complications of disease or inflammation related disorder; determine disease or inflammation related disorder prognosis; evaluate the patient's risk, or "stratify" a group of patients; assess response to current drug therapy; assess response to current non-pharmacological therapy; determine the most appropriate medication or treatment for the patient; predict whether a patient is likely to respond to a particular drug; and determine most appropriate additional diagnostic testing for the patient, among other clinically and epidemiologically relevant applications.

The diagnostic oligonucleotides and diagnostic oligonucleotide sets of the invention can be utilized for a variety of purposes by physicians, healthcare workers, hospitals, laboratories, patients, companies and other institutions. As indicated previously, essentially any disease, condition, or status for which at least one nucleotide sequence is differentially expressed in leukocyte populations (or sub-populations) can be evaluated, e.g., diagnosed, monitored, etc. using the individual diagnostic oligonucleotides or diagnostic oligonucleotide sets and methods of the invention. In addition to assessing health status at an individual level, the individual diagnostic oligonucleotides and diagnostic oligonucleotide sets of the present invention are suitable for evaluating subjects at a "population level," e.g., for epidemiological studies, or for population screening for a condition or disease.

Collection and Preparation of Sample

RNA, protein and/or DNA are prepared using methods well-known in the art, as further described herein. It is appreciated that subject samples collected for use in the methods of the invention are generally collected in a clinical setting, where delays may be introduced before RNA samples are prepared from the subject samples of whole blood, e.g. the blood sample may not be promptly delivered to the clinical lab for further processing. Further delay may be introduced in the clinical lab setting where multiple samples are generally being processed at any given time. For this reason, methods that feature lengthy incubations of intact leukocytes at room temperature are not preferred, because the expression profile of the leukocytes may change during this extended time period. For example, RNA can be isolated from whole blood using a phenol/guanidine isothiocyanate reagent or another direct whole-blood lysis method, as described in, e.g., U.S. Pat. Nos. 5,346,994 and 4,843,155. This method may be less preferred under certain circumstances because the large majority of the RNA recovered from whole blood RNA extraction comes from erythrocytes since these cells outnumber leukocytes 1000:1. Care must be taken to ensure that the presence of erythrocyte RNA and protein does not introduce bias in the RNA expression profile data or lead to inadequate sensitivity or specificity of probes.

Alternatively, intact leukocytes may be collected from whole blood using a lysis buffer that selectively lyses erythrocytes, but not leukocytes, as described, e.g., in (U.S. Pat. Nos. 5,973,137, and 6,020,186). Intact leukocytes are then collected by centrifugation, and leukocyte RNA is isolated using standard protocols, as described herein. However, this method does not allow isolation of sub-populations of leukocytes, e.g. mononuclear cells, which may be desired. In addition, the expression profile may change during the lengthy incubation in lysis buffer, especially in a busy clinical lab where large numbers of samples are being prepared at any given time.

Alternatively, specific leukocyte cell types can be separated using density gradient reagents (Boyum, A, 1968.). For example, mononuclear cells may be separated from whole blood using density gradient centrifugation, as described, e.g., in U.S. Pat. Nos. 4,190,535, 4,350,593, 4,751,001, 4,818,418, and 5,053,134. Blood is drawn directly into a tube containing an anticoagulant and a density reagent (such as Ficoll or Percoll). Centrifugation of this tube results in separation of blood into an erythrocyte and granulocyte layer, a mononuclear cell suspension, and a plasma layer. The mononuclear cell layer is easily removed and the cells can be collected by centrifugation, lysed, and frozen. Frozen samples are stable until RNA can be isolated. Density centrifugation, however, must be conducted at room temperature, and if processing is unduly lengthy, such as in a busy clinical lab, the expression profile may change.

Alternatively, cells can be separated using fluorescence activated cell sorting (FACS) or some other technique, which divides cells into subsets based on gene or protein expression. This may be desirable to enrich the sample for cells of interest, but it may also introduce cell manipulations and time delays, which result in alteration of gene expression profiles (Cantor et al. 1975; Galbraith et al. 1999).

The quality and quantity of each clinical RNA sample is desirably checked before amplification and labeling for array hybridization, using methods known in the art. For example, one microliter of each sample may be analyzed on a Bioanalyzer (Agilent 2100 Palo Alto, Calif. USA) using an RNA 6000 nano LabChip (Caliper, Mountain View, Calif. USA). Degraded RNA is identified by the reduction of the 28S to 18S ribosomal RNA ratio and/or the presence of large quantities of RNA in the 25-100 nucleotide range.

It is appreciated that the RNA sample for use with a diagnostic oligonucleotide or a diagnostic oligonucleotide set may be produced from the same or a different cell population, sub-population and/or cell type as used to identify the diagnostic oligonucleotide or diagnostic oligonucleotide set. For example, an individual diagnostic oligonucleotide or a diagnostic oligonucleotide set identified using RNA extracted from mononuclear cells may be suitable for analysis of RNA extracted from whole blood or mononuclear cells, depending on the particular characteristics of the individual diagnostic oligonucleotide or members of the diagnostic oligonucleotide set. Generally, diagnostic oligonucleotide sets must be tested and validated when used with RNA derived from a different cell population, sub-population or cell type than that used when obtaining the diagnostic gene set. Factors such as the cell-specific gene expression of diagnostic oligonucleotide set members or, redundancy of the information provided by members of the diagnostic oligonucleotide set, expression level of the member of the diagnostic oligonucleotide set, and cell-specific alteration of expression of a member of the diagnostic oligonucleotide set will contribute to the usefullness of using a different RNA source than that used when identifying the members of the diagnostic oligonucleotide set. It is appreciated that it may be desirable to assay RNA derived from whole blood, obviating the need to isolate particular cell types from the blood.

Rapid Method of RNA Extraction Suitable for Production in a Clinical Setting of High Quality RNA for Expression Profiling In a clinical setting, obtaining high quality RNA preparations suitable for expression profiling, from a desired population of leukocytes poses certain technical challenges, including: the lack of capacity for rapid, high-throughput sample processing in the clinical setting, and the possibility that delay in processing (in a busy lab or in the clinical setting) may adversely affect RNA quality, e.g. by permitting the expression profile of certain nucleotide sequences to shift. Also, use of toxic and expensive reagents, such as phenol, may be disfavored in the clinical setting due to the added expense associated with shipping and handling such reagents.

A useful method for RNA isolation for leukocyte expression profiling would allow the isolation of monocyte and lymphocyte RNA in a timely manner, while preserving the expression profiles of the cells, and allowing inexpensive production of reproducible high-quality RNA samples. Accordingly, the invention provides a method of adding inhibitor(s) of RNA transcription and/or inhibitor(s) of protein synthesis, such that the expression profile is "frozen" and RNA degradation is reduced. A desired leukocyte population or sub-population is then isolated, and the sample may be frozen or lysed before further processing to extract the RNA. Blood is drawn from subject population and exposed to ActinomycinD (to a final concentration of 10 ug/ml) to inhibit transcription, and cycloheximide (to a final concentration of 10 ug/ml) to inhibit protein synthesis. The inhibitor(s) can be injected into the blood collection tube in liquid form as soon as the blood is drawn, or the tube can be manufactured to contain either lyophilized inhibitors or inhibitors that are in solution with the anticoagulant. At this point, the blood sample can be stored at room temperature until the desired leukocyte population or sub-population is isolated, as described elsewhere. RNA is isolated using standard methods, e.g., as described above, or a cell pellet or extract can be frozen until further processing of RNA is convenient.

The invention also provides a method of using a low-temperature density gradient for separation of a desired leukocyte sample. In another embodiment, the invention provides the combination of use of a low-temperature density gradient and the use of transcriptional and/or protein synthesis inhibitor(s). A desired leukocyte population is separated using a density gradient solution for cell separation that maintains the required density and viscosity for cell separation at 0-4° C. Blood is drawn into a tube containing this solution and may be refrigerated before and during processing as the low temperatures slow cellular processes and minimize expression profile changes. Leukocytes are separated, and RNA is isolated using standard methods. Alternately, a cell pellet or extract is frozen until further processing of RNA is convenient. Care must be taken to avoid rewarming the sample during further processing steps.

Alternatively, the invention provides a method of using low-temperature density gradient separation, combined with the use of actinomycin A and cyclohexamide, as described above.

Assessing Expression for Diagnostics

Expression profiles for the diagnostic oligonucleotide or the set of diagnostic oligonucleotide sequences in a subject sample can be evaluated by any technique that determines the expression of each component oligonucleotide sequence. Methods suitable for expression analysis are known in the art, and numerous examples are discussed in the Sections titled "Methods of obtaining expression data" and "high throughput expression Assays", found in U.S. patent application Ser. No. 10/006,290 (such sections are herein incorporated by reference in their entirety for the methods therein disclosed).

In many cases, evaluation of expression profiles is most efficiently, and cost effectively, performed by analyzing RNA expression. Alternatively, the proteins encoded by each component of the diagnostic oligonucleotide set are detected for diagnostic purposes by any technique capable of determining protein expression, e.g., as described above. Expression profiles can be assessed in subject leukocyte sample using the same or different techniques as those used to identify and validate the diagnostic oligonucleotide set. For example, a diagnostic oligonucleotide set or a diagnostic oligonucleotide set identified as a subset of sequences on a cDNA microarray can be utilized for diagnostic (or prognostic, or monitoring, etc.) purposes on the same array from which they were identified. Alternatively, the diagnostic oligonucleotide sets for a given disease or condition can be organized onto a dedicated sub-array for the indicated purpose. It is important to note that if diagnostic oligonucleotide sets are discovered using one technology, e.g. RNA expression profiling, but applied as a diagnostic using another technology, e.g. protein expression profiling, the nucleotide (or gene, or protein) sets must generally be validated for diagnostic purposes with the new technology. In addition, it is appreciated that diagnostic oligonucleotide sets that are developed for one use, e.g. to diagnose a particular disease or inflammation related disorder, may later be found to be useful for a different application, e.g. to predict the likelihood that the particular disease or inflammation related disorder will occur. Generally, the diagnostic oligonucleotide set will need to be validated for use in the second circumstance. As discussed herein, the sequence of diagnostic oligonucleotide set members may be amplified from RNA or cDNA using methods known in the art providing specific amplification of the nucleotide sequences.

General Protein Methods

Protein products of the nucleotide sequences of the invention may include proteins that represent functionally equivalent gene products. Such an equivalent gene product may contain deletions, additions or substitutions of amino acid residues within the amino acid sequence encoded by the nucleotide sequences described, above, but which result in a silent change, thus producing a functionally equivalent nucleotide sequence product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Functionally equivalent", as utilized herein, refers to a protein capable of exhibiting a substantially similar in vivo activity as the endogenous gene products encoded by the oligonucleotides described, herein.

The gene products (protein products of the nucleotide sequences) may be produced by recombinant DNA technology using techniques well known in the art. Thus, methods for preparing the gene polypeptides and peptides of the invention by expressing nucleic acid encoding nucleotide sequences are described herein. Methods which are well known to those skilled in the art can be used to construct expression vectors containing nucleotide sequence protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding nucleotide sequence protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety A variety of host-expression vector systems may be utilized to express the nucleotide sequence coding sequences of the invention. Such host-expression systems represent vehicles by which the coding sequences of interest may be produced and subsequently purified, but also represent cells which may, when transformed or transfected with the appropriate nucleotide coding sequences, exhibit the protein encoded by the nucleotide sequence of the invention in situ. These include but are not limited to microorganisms such as bacteria (e.g., *E. coli, B. subtilis*) transformed with recombinant bacteriophage DNA, plasmid DNA or cosmid DNA expression vectors containing nucleotide sequence protein coding sequences; yeast (e.g. *Saccharomyces, Pichia*) transformed with recombinant yeast expression vectors containing the nucleotide sequence protein coding sequences; insect cell systems infected with recombinant virus expression vectors (e.g., baculovirus) containing the nucleotide sequence protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing nucleotide sequence protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5 K promoter).

In bacterial systems, a number of expression vectors may be advantageously selected depending upon the use intended for the nucleotide sequence protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the nucleotide sequence protein coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 264:5503-5509); and the likes of pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target nucleotide sequence protein can be released from the GST moiety. Other systems useful in the invention include use of the FLAG epitope or the 6-HIS systems.

In an insect system, Autographa californica nuclear polyhedrosis virus (AcNPV) is used as a vector to express foreign nucleotide sequences. The virus grows in Spodoptera frugiperda cells. The nucleotide sequence coding sequence may be cloned individually into non-essential regions (for example the polyhedrin gene) of the virus and placed under control of an AcNPV promoter (for example the polyhedrin promoter). Successful insertion of nucleotide sequence coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted nucleotide sequence is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the nucleotide sequence coding sequence of interest may be ligated to an adenovirus transcription/translation control complex, e.g., the late promoter and tripartite leader sequence. This chimeric nucleotide sequence may then be inserted in the adenovirus genome by in vitro or in vivo recombination. Insertion in a non-essential region of the viral genome (e.g., region E1 or E3) will result in a recombinant virus that is viable and capable of expressing nucleotide sequence encoded protein in infected hosts. (E.g., See Logan & Shenk, 1984, Proc. Natl. Acad. Sci. USA 81:3655-3659). Specific initiation signals may also be required for efficient translation of inserted nucleotide sequence coding sequences. These signals include the ATG initiation codon and adjacent sequences. In cases where an entire nucleotide sequence, including its own initiation codon and adjacent sequences, is inserted into the appropriate expression vector, no additional translational control signals may be needed. However, in cases where only a portion of the nucleotide sequence coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In addition, a host cell strain may be chosen which modulates the expression of the inserted sequences, or modifies and processes the product of the nucleotide sequence in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the nucleotide sequence encoded protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express nucleotide sequence encoded protein. Such engineered cell lines may be particularly useful in screening and evaluation of compounds that affect the endogenous activity of the nucleotide sequence encoded protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972-8976). In this system, the nucleotide sequence of interest is subcloned into a vaccinia recombination plasmid such that the nucleotide sequence's open reading frame is translationally fused to an amino-terminal tag consisting of six histidine residues. Extracts from cells infected with recombinant vaccinia virus are loaded onto Ni.sup.2+-nitriloacetic acid-agarose columns and histidine-tagged proteins are selectively eluted with imidazole-containing buffers.

Where recombinant DNA technology is used to produce the protein encoded by the nucleotide sequence for such assay systems, it may be advantageous to engineer fusion proteins that can facilitate labeling, immobilization and/or detection.

Antibodies

Indirect labeling involves the use of a protein, such as a labeled antibody, which specifically binds to the protein encoded by the nucleotide sequence. Such antibodies include but are not limited to polyclonal, monoclonal, chimeric, single chain, Fab fragments and fragments produced by an Fab expression library.

The invention also provides for antibodies to the protein encoded by the nucleotide sequences. Described herein are methods for the production of antibodies capable of specifically recognizing one or more nucleotide sequence epitopes. Such antibodies may include, but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Such antibodies may be used, for example, in the detection of a nucleotide sequence in a biological sample, or, alternatively, as a method for the inhibition of abnormal gene activity, for example, the inhibition of a disease or inflammation related disorder target nucleotide sequence, as further described below. Thus, such antibodies may be utilized as part of cardiovascular or other disease or inflammation related disorder treatment method, and/or may be used as part of diagnostic techniques whereby patients may be tested for abnormal levels of nucleotide sequence encoded proteins, or for the presence of abnormal forms of the such proteins.

For the production of antibodies to a nucleotide sequence, various host animals may be immunized by injection with a protein encoded by the nucleotide sequence, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Polyclonal antibodies are heterogeneous populations of antibody molecules derived from the sera of animals immunized with an antigen, such as gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026-2030), and the EBV-hybridoma technique (Cole et al., 1985, Monoclonal Antibodies And Cancer Therapy, Alan R. Liss, Inc., pp. 77-96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334: 544-546) can be adapted to produce nucleotide sequence-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275-1281) to allow rapid and easy identification of monoclonal Fab fragments with the desired specificity.

Disease or Inflammation Related Disorder Specific Target Oligonucleotide Sequences The invention also provides disease or inflammation related disorder specific target oligonucleotide sequences, and sets of disease or inflammation related disorder specific target nucleotide sequences. The diagnostic oligonucleotide sets, subsets thereof, nucleotide sequences, and individual members of the diagnostic oligonucleotide sets identified as described above are also disease or inflammation related disorder specific target nucleotide sequences. In particular, individual nucleotide sequences that are differentially regulated or have predictive value that is strongly correlated with a disease or inflammation related disorder or criterion thereof are especially favorable as disease or inflammation related disorder specific target nucleotide sequences. Sets of genes that are co-regulated may also be identified as disease or inflammation related disorder specific target oligonucleotide sets. Such oligonucleotide sequences and/or oligonucleotide sequence products are targets for modulation by a variety of agents and techniques. For example, disease or inflammation related disorder specific target oligonucleotide sequences (or the products of such oligonucleotide sequences, or sets of disease or inflammation related disorder specific target oligonucleotide sequences) can be inhibited or activated by, e.g., target specific monoclonal antibodies or small molecule inhibitors, or delivery of the oligonucleotide sequence or gene product of the oligonucleotide sequence to patients. Also, sets of genes can be inhibited or activated by a variety of agents and techniques. The specific usefulness of the target oligonucleotide sequence(s) depends on the subject groups from which they were discovered, and the disease or inflammation related disorder or criterion thereof with which they correlate.

Imaging

The invention also provides for imaging reagents. The differentially expressed leukocyte nucleotide sequences, diagnostic oligonucleotide sets, or portions thereof, and nucleotide sequences of the invention are nucleotide sequences expressed in cells with or without disease or inflammation related disorder. Leukocytes expressing a nucleotide sequence(s) that is differentially expressed in a disease condition or inflammation related disorder may localize within the body to sites that are of interest for imaging purposes. For example, a leukocyte expressing a nucleotide sequence(s) that are differentially expressed in an individual having atherosclerosis may localize or accumulate at the site of an atherosclerotic plaque. Such leukocytes, when labeled, may provide a detection reagent for use in imaging regions of the body where labeled leukocyte accumulate or localize, for example, at the atherosclerotic plaque in the case of atherosclerosis. For example, leukocytes are collected from a subject, labeled in vitro, and reintroduced into a subject. Alternatively, the labeled reagent is introduced into the subject individual, and leukocyte labeling occurs within the patient.

Imaging agents that detect the imaging targets of the invention are produced by well-known molecular and immunological methods (for exemplary protocols, see, e.g., Ausubel, Berger, and Sambrook, as well as Harlow and Lane, supra).

For example, a full-length nucleic acid sequence, or alternatively, a gene fragment encoding an immunogenic peptide or polypeptide fragments, is cloned into a convenient expression vector, for example, a vector including an in-frame epitope or substrate binding tag to facilitate subsequent purification. Protein is then expressed from the cloned cDNA sequence and used to generate antibodies, or other specific binding molecules, to one or more antigens of the imaging target protein. Alternatively, a natural or synthetic polypeptide (or peptide) or small molecule that specifically binds (or is specifically bound to) the expressed imaging target can be identified through well established techniques (see, e.g., Mendel et al. (2000) Anticancer Drug Des 15:29-41; Wilson (2000) Curr Med Chem 7:73-98; Hamby and Showwalter (1999) Pharmacol Ther 82:169-93; and Shimazawa et al. (1998) Curr Opin Struct Biol 8:451-8). The binding molecule, e.g., antibody, small molecule ligand, etc., is labeled with a contrast agent or other detectable label, e.g., gadolinium, iodine, or a gamma-emitting source. For in-vivo imaging of a disease or inflammation related disorder process that involved leukocytes, the labeled antibody is infused into a subject, e.g., a human patient or animal subject, and a sufficient period of time is passed to permit binding of the antibody to target cells. The subject is then imaged with appropriate technology such as MRI (when the label is gadolinium) or with a gamma counter (when the label is a gamma emitter).

Identification of Nucleotide Sequence Involved in Leukocyte Adhesion

The invention also encompasses a method of identifying nucleotide sequences involved in leukocyte adhesion. The interaction between the endothelial cell and leukocyte is a fundamental mechanism of all inflammatory disorders, including the diagnosis and prognosis of allograft rejection the disorders listed in Table 1. For example, the first visible abnormality in atherosclerosis is the adhesion to the endothelium and diapedesis of mononuclear cells (e.g., T-cell and monocyte). Insults to the endothelium (for example, cytokines, tobacco, diabetes, hypertension and many more) lead to endothelial cell activation. The endothelium then expresses adhesion molecules, which have counter receptors on mononuclear cells. Once the leukocyte receptors have bound the endothelial adhesion molecules, they stick to the endothelium, roll a short distance, stop and transmigrate across the endothelium. A similar set of events occurs in both acute and chronic inflammation. When the leukocyte binds the endothelial adhesion molecule, or to soluble cytokines secreted by endothelial or other cells, a program of gene expression is activated in the leukocyte. This program of expression leads to leukocyte rolling, firm adhesion and transmigration into the vessel wall or tissue parenchyma. Inhibition of this process is highly desirable goal in anti-inflammatory drug development. In addition, leukocyte nucleotide sequences and epithelial cell nucleotide sequences, that are differentially expressed during this process may be disease or inflammation related disorder specific target nucleotide sequences.

Human endothelial cells, e.g. derived from human coronary arteries, human aorta, human pulmonary artery, human umbilical vein or microvascular endothelial cells, are cultured as a confluent monolayer, using standard methods. Some of the endothelial cells are then exposed to cytokines or another activating stimuli such as oxidized LDL, hyperglycemia, shear stress, or hypoxia (Moser et al. 1992). Some endothelial cells are not exposed to such stimuli and serve as controls. For example, the endothelial cell monolayer is incubated with culture medium containing 5 U/ml of human recombinant IL-1alpha or 10 ng/ml TNF (tumor necrosis factor), for a period of minutes to overnight. The culture medium composition is changed or the flask is sealed to induce hypoxia. In addition, tissue culture plate is rotated to induce sheer stress.

Human T-cells and/or monocytes are cultured in tissue culture flasks or plates, with LGM-3 media from Clonetics. Cells are incubated at 37 degree C., 5% CO2 and 95% humidity. These leukocytes are exposed to the activated or control endothelial layer by adding a suspension of leukocytes on to the endothelial cell monolayer. The endothelial cell monolayer is cultured on a tissue culture treated plate/flask or on a microporous membrane. After a variable duration of exposures, the endothelial cells and leukocytes are harvested separately by treating all cells with trypsin and then sorting the endothelial cells from the leukocytes by magnetic affinity reagents to an endothelial cell specific marker such as PECAM-1 (Stem Cell Technologies). RNA is extracted from the isolated cells by standard techniques. Leukocyte RNA is labeled as described above, and hybridized to leukocyte diagnostic gene library. Epithelial cell RNA is also labeled and hybridized to the leukocyte diagnostic gene library. Alternatively, the epithelial cell RNA is hybridized to a epithelial cell derived diagnostic gene library, prepared according to the methods described for leukocyte derived diagnostic gene libraries, above.

Hybridization to diagnostic gene libraries will reveal nucleotide sequences that are up-regulated or down-regulated in leukocyte and/or epithelial cells undergoing adhesion. The differentially regulated nucleotide sequences are further characterized, e.g. by isolating and sequencing the full-length sequence, analysis of the DNA and predicted protein sequence, and functional characterization of the protein product of the nucleotide sequence, as described above. Further characterization may result in the identification of leukocyte adhesion specific target nucleotide sequences, which may be candidate targets for regulation of the inflammatory process. Small molecule or antibody inhibitors can be developed to inhibit the target nucleotide sequence function. Such inhibitors are tested for their ability to inhibit leukocyte adhesion in the in vitro test described above.

Integrated Systems

Integrated systems for the collection and analysis of expression profiles, and molecular signatures, as well as for the compilation, storage and access of the databases of the invention, typically include a digital computer with software including an instruction set for sequence searching and analysis, and, optionally, high-throughput liquid control software, image analysis software, data interpretation software, a robotic control armature for transferring solutions from a source to a destination (such as a detection device) operably linked to the digital computer, an input device (e.g., a computer keyboard) for entering subject data to the digital computer, or to control analysis operations or high throughput sample transfer by the robotic control armature. Optionally, the integrated system further comprises an image scanner for digitizing label signals from labeled assay components, e.g., labeled nucleic acid hybridized to a diagnostic gene library or diagnostic oligonucleotide set microarray. The image scanner can interface with image analysis software to provide a measurement of the presence or intensity of the hybridized label, i.e., indicative of an on/off expression pattern or an increase or decrease in expression.

Readily available computational hardware resources using standard operating systems are fully adequate, e.g., a PC (Intel x86 or Pentium™ chip-compatible WINDOWS 2000™, WINDOWS XP™, LINUX) or even Macintosh™ or Sun™ will suffice for use in the integrated systems of the invention. Current art in software technology is similarly adequate (i.e., there are a multitude of mature programming languages and source code suppliers) for design, e.g., of an upgradeable open-architecture object-oriented heuristic algorithm, or instruction set for expression analysis, as described herein. For example, software for aligning or otherwise manipulating molecular signatures can be constructed by one of skill using a standard programming language such as Visual basic, Fortran, Basic, Java, or the like, according to the methods herein.

Various methods and algorithms, including genetic algorithms and neural networks, can be used to perform the data collection, correlation, and storage functions, as well as other desirable functions, as described herein. In addition, digital or analog systems such as digital or analog computer systems can control a variety of other functions such as the display and/or control of input and output files.

For example, standard desktop applications such as word processing software (e.g., Corel WordPerfect™ or Microsoft Word™) and database software (e.g., spreadsheet software such as Corel Quattro Pro™, Microsoft Excel™, or database programs such as Microsoft Access™ or Paradox™) can be adapted to the present invention by inputting one or more character string corresponding, e.g., to an expression pattern or profile, subject medical or historical data, molecular signature, or the like, into the software which is loaded into the memory of a digital system, and carrying out the operations indicated in an instruction set. For example, systems can include the foregoing software having the appropriate character string information, e.g., used in conjunction with a user interface in conjunction with a standard operating system such as a Windows, Macintosh or LINUX system. For example, an instruction set for manipulating strings of characters, either by programming the required operations into the applications or with the required operations performed manually by a user (or both). For example, specialized sequence alignment programs such as PILEUP or BLAST can also be incorporated into the systems of the invention, e.g., for alignment of nucleic acids or proteins (or corresponding character strings).

Software for performing the statistical methods required for the invention, e.g., to determine correlations between expression profiles and subsets of members of the diagnostic oligonucleotide libraries, such as programmed embodiments of the statistical methods described above, are also included in the computer systems of the invention. Alternatively, programming elements for performing such methods as principle component analysis (PCA) or least squares analysis can also be included in the digital system to identify relationships between data. Exemplary software for such methods is provided by Partek, Inc., St. Peter, Mo.; at the web site partek.com.

Any controller or computer optionally includes a monitor which can include, e.g., a flat panel display (e.g., active matrix liquid crystal display, liquid crystal display), a cathode ray tube ("CRT") display, or another display system which serves as a user interface, e.g., to output predictive data. Computer circuitry, including numerous integrated circuit chips, such as a microprocessor, memory, interface circuits, and the like, is often placed in a casing or box which optionally also includes a hard disk drive, a floppy disk drive, a high capacity removable drive such as a writeable CD-ROM, and other common peripheral elements.

Inputting devices such as a keyboard, mouse, or touch sensitive screen, optionally provide for input from a user and for user selection, e.g., of sequences or data sets to be compared or otherwise manipulated in the relevant computer system. The computer typically includes appropriate software for receiving user instructions, either in the form of user input into a set parameter or data fields (e.g., to input relevant subject data), or in the form of preprogrammed instructions, e.g., preprogrammed for a variety of different specific operations. The software then converts these instructions to appropriate language for instructing the system to carry out any desired operation.

The integrated system may also be embodied within the circuitry of an application specific integrated circuit (ASIC) or programmable logic device (PLD). In such a case, the invention is embodied in a computer readable descriptor language that can be used to create an ASIC or PLD. The integrated system can also be embodied within the circuitry or logic processors of a variety of other digital apparatus, such as PDAs, laptop computer systems, displays, image editing equipment, etc.

The digital system can comprise a learning component where expression profiles, and relevant subject data are compiled and monitored in conjunction with physical assays, and where correlations, e.g., molecular signatures with predictive value for a disease or inflammation related disorder, are established or refined. Successful and unsuccessful combinations are optionally documented in a database to provide justification/preferences for user-base or digital system based selection of diagnostic oligonucleotide sets with high predictive accuracy for a specified disease or condition.

The integrated systems can also include an automated workstation. For example, such a workstation can prepare and analyze leukocyte RNA samples by performing a sequence of events including: preparing RNA from a human blood sample; labeling the RNA with an isotopic or non-isotopic label; hybridizing the labeled RNA to at least one array comprising all or part of the diagnostic gene library or diagnostic oligonucleotide set; and detecting the hybridization pattern. The hybridization pattern is digitized and recorded in the appropriate database.

Automated RNA Preparation Tool

The invention also includes an automated RNA preparation tool for the preparation of mononuclear cells from whole blood samples, and preparation of RNA from the mononuclear cells. In a preferred embodiment, the use of the RNA preparation tool is fully automated, so that the cell separation and RNA isolation would require no human manipulations. Full automation is advantageous because it minimizes delay, and standardizes sample preparation across different laboratories. This standardization increases the reproducibility of the results.

The processes performed by the RNA preparation tool of the invention are as follows. A primary component of the device is a centrifuge (A). Tubes of whole blood containing a density gradient solution, transcription/translation inhibitors, and a gel barrier that separates erythrocytes from mononuclear cells and serum after centrifugation are placed in the centrifuge (B). The barrier is permeable to erythrocytes and granulocytes during centrifugation, but does not allow mononuclear cells to pass through (or the barrier substance has a density such that mononuclear cells remain above the level of the barrier during the centrifugation). After centrifugation, the erythrocytes and granulocytes are trapped beneath the barrier, facilitating isolation of the mononuclear cell and serum layers. A mechanical arm removes the tube and inverts it to mix the mononuclear cell layer and the serum (C). The arm next pours the supernatant into a fresh tube (D), while the erythrocytes and granulocytes remained below the barrier. Alternatively, a needle is used to aspirate the supernatant and transfer it to a fresh tube. The mechanical arms of the device opens and closes lids, dispenses PBS to aid in the collection of the mononuclear cells by centrifugation, and moves the tubes in and out of the centrifuge. Following centrifugation, the supernatant is poured off or removed by a vacuum device (E), leaving an isolated mononuclear cell pellet. Purification of the RNA from the cells is performed automatically, with lysis buffer and other purification solutions (F) automatically dispensed and removed before and after centrifugation steps. The result is a purified RNA solution. In another embodiment, RNA isolation is performed using a column or filter method. In yet another embodiment, the invention includes an on-board homogenizer for use in cell lysis.

Other Automated Systems

Automated and/or semi-automated methods for solid and liquid phase high-throughput sample preparation and evaluation are available, and supported by commercially available devices. For example, robotic devices for preparation of nucleic acids from bacterial colonies, e.g., to facilitate production and characterization of the diagnostic gene library or diagnostic oligonucleotide geneset include, for example, an automated colony picker (e.g., the Q-bot, Genetix, U.K.) capable of identifying, sampling, and inoculating up to 10,000/4 hrs different clones into 96 well microtiter dishes. Alternatively, or in addition, robotic systems for liquid handling are available from a variety of sources, e.g., automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Beckman Coulter, Inc. (Fullerton, Calif.)) which mimic the manual operations performed by a scientist. Any of the above devices are suitable for use with the present invention, e.g., for high-throughput analysis of library components or subject leukocyte samples. The nature and implementation of modifications to these devices (if any) so that they can operate as discussed herein will be apparent to persons skilled in the relevant art.

High throughput screening systems that automate entire procedures, e.g., sample and reagent pipetting, liquid dispensing, timed incubations, and final readings of the microplate in detector(s) appropriate for the relevant assay are commercially available. (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These configurable systems provide high throughput and rapid start up as well as a high degree of flexibility and customization. Similarly, arrays and array readers are available, e.g., from Affymetrix, PE Biosystems, and others.

The manufacturers of such systems provide detailed protocols the various high throughput. Thus, for example, Zymark Corp. provides technical bulletins describing screening systems for detecting the modulation of gene transcription, ligand binding, and the like.

A variety of commercially available peripheral equipment, including, e.g., optical and fluorescent detectors, optical and fluorescent microscopes, plate readers, CCD arrays, phosphorimagers, scintillation counters, phototubes, photodiodes, and the like, and software is available for digitizing, storing and analyzing a digitized video or digitized optical or other assay results, e.g., using PC (Intel x86 or pentium chip-compatible WINDOWS 2000™ or WINDOWS XP™ based machines), MACINTOSH™, or UNIX based (e.g., SUN™ work station) computers.

Embodiment in a Web Site

The methods described above can be implemented in a localized or distributed computing environment. For example, if a localized computing environment is used, an array comprising a diagnostic gene library, or diagnostic oligonucleotide set, is configured in proximity to a detector, which is, in turn, linked to a computational device equipped with user input and output features.

In a distributed environment, the methods can be implemented on a single computer with multiple processors or, alternatively, on multiple computers. The computers can be linked, e.g. through a shared bus, but more commonly, the computer(s) are nodes on a network. The network can be generalized or dedicated, at a local level or distributed over a wide geographic area. In certain embodiments, the computers are components of an intra-net or an internet.

The predictive data corresponding to subject molecular signatures (e.g., expression profiles, and related diagnostic, prognostic, or monitoring results) can be shared by a variety of parties. In particular, such information can be utilized by the subject, the subject's health care practitioner or provider, a company or other institution, or a scientist. An individual subject's data, a subset of the database or the entire database recorded in a computer readable medium can be accessed directly by a user by any method of communication, including, but not limited to, the internet. With appropriate computational devices, integrated systems, communications networks, users at remote locations, as well as users located in proximity to, e.g., at the same physical facility, the database can access the recorded information. Optionally, access to the database can be controlled using unique alphanumeric passwords that provide access to a subset of the data. Such provisions can be used, e.g., to ensure privacy, anonymity, etc.

Typically, a client (e.g., a patient, practitioner, provider, scientist, or the like) executes a Web browser and is linked to a server computer executing a Web server. The Web browser is, for example, a program such as IBM's Web Explorer, Internet explorer, NetScape or Mosaic, or the like. The Web server is typically, but not necessarily, a program such as IBM's HTTP Daemon or other WWW daemon (e.g., LINUX-based forms of the program). The client computer is bi-directionally coupled with the server computer over a line or via a wireless system. In turn, the server computer is bi-directionally coupled with a website (server hosting the website) providing access to software implementing the methods of this invention.

A user of a client connected to the Intranet or Internet may cause the client to request resources that are part of the web site(s) hosting the application(s) providing an implementation of the methods described herein. Server program(s) then process the request to return the specified resources (assuming they are currently available). A standard naming convention has been adopted, known as a Uniform Resource Locator ("URL"). This convention encompasses several types of location names, presently including subclasses such as Hypertext Transport Protocol ("http"), File Transport Protocol ("ftp"), gopher, and Wide Area Information Service ("WAIS"). When a resource is downloaded, it may include the URLs of additional resources. Thus, the user of the client can easily learn of the existence of new resources that he or she had not specifically requested.

Methods of implementing Intranet and/or Intranet embodiments of computational and/or data access processes are well known to those of skill in the art and are documented, e.g., in ACM Press, pp. 383-392; ISO-ANSI, Working Draft, "Information Technology-Database Language SQL", Jim Melton, Editor, International Organization for Standardization and American National Standards Institute, July 1992; ISO Working Draft, "Database Language SQL-Part 2:Foundation (SQL/Foundation)", CD9075-2:199.chi.SQL, Sep. 11, 1997; and Cluer et al. (1992) A General Framework for the Optimization of Object-Oriented Queries, Proc SIGMOD International Conference on Management of Data, San Diego, Calif., Jun. 2-5, 1992, SIGMOD Record, vol. 21, Issue 2, June, 1992; Stonebraker, M., Editor;. Other resources are available, e.g., from Microsoft, IBM, Sun and other software development companies.

Using the tools described above, users of the reagents, methods and database as discovery or diagnostic tools can query a centrally located database with expression and subject data. Each submission of data adds to the sum of expression and subject information in the database. As data is added, a new correlation statistical analysis is automatically run that incorporates the added clinical and expression data. Accordingly, the predictive accuracy and the types of correlations of the recorded molecular signatures increases as the database grows.

For example, subjects, such as patients, can access the results of the expression analysis of their leukocyte samples and any accrued knowledge regarding the likelihood of the patient's belonging to any specified diagnostic (or prognostic, or monitoring, or risk group), i.e., their expression profiles, and/or molecular signatures. Optionally, subjects can add to the predictive accuracy of the database by providing additional information to the database regarding diagnoses, test results, clinical or other related events that have occurred since the time of the expression profiling. Such information can be provided to the database via any form of communication, including, but not limited to, the internet. Such data can be used to continually define (and redefine) diagnostic groups. For example, if 1000 patients submit data regarding the occurrence of myocardial infarction over the 5 years since their expression profiling, and 300 of these patients report that they have experienced a myocardial infarction and 700 report that they have not, then the 300 patients define a new "group A." As the algorithm is used to continually query and revise the database, a new diagnostic oligonucleotide set that differentiates groups A and B (i.e., with and without myocardial infarction within a five year period) is identified. This newly defined nucleotide set is then be used (in the manner described above) as a test that predicts the occurrence of myocardial infarction over a five-year period. While submission directly by the patient is exemplified above, any individual with access and authority to submit the relevant data e.g., the patient's physician, a laboratory technician, a health care or study administrator, or the like, can do so.

As will be apparent from the above examples, transmission of information via the internet (or via an intranet) is optionally bidirectional. That is, for example, data regarding expression profiles, subject data, and the like are transmitted via a communication system to the database, while information regarding molecular signatures, predictive analysis, and the like, are transmitted from the database to the user. For example, using appropriate configurations of an integrated system including a microarray comprising a diagnostic oligonucleotide set, a detector linked to a computational device can directly transmit (locally or from a remote workstation at great distance, e.g., hundreds or thousands of miles distant from the database) expression profiles and a corresponding individual identifier to a central database for analysis according to the methods of the invention. According to, e.g., the algorithms described above, the individual identifier is assigned to one or more diagnostic (or prognostic, or monitoring, etc.) categories. The results of this classification are then relayed back, via, e.g., the same mode of communication, to a recipient at the same or different internet (or intranet) address.

Kits

The present invention is optionally provided to a user as a kit. Typically, a kit contains one or more diagnostic oligonucleotide sets of the invention. Alternatively, the kit contains the diagnostic gene library of the invention. Most often, the kit contains a diagnostic oligonucleotide probe set, or other subset of a diagnostic gene library, e.g., as a cDNA or antibody microarray packaged in a suitable container. The kit may further comprise, one or more additional reagents, e.g., substrates, labels, primers, for labeling expression products, tubes and/or other accessories, reagents for collecting blood samples, buffers, e.g., erythrocyte lysis buffer, leukocyte lysis buffer, hybridization chambers, cover slips, etc., as well as a software package, e.g., including the statistical methods of the invention, e.g., as described above, and a password and/or account number for accessing the compiled database. The kit optionally further comprises an instruction set or user manual detailing preferred methods of using the diagnostic oligonucleotide sets in the methods of the invention. In one embodiment, the kit may include contents useful for the discovery of diagnostic oligonucleotide sets using microarrays. The kit may include sterile, endotoxin and RNAse free blood collection tubes. The kit may also include alcohol swabs, tourniquet, blood collection set, and/or PBS (phosphate buffer saline; needed when method of example 2 is used to derived mononuclear RNA). The kit may also include cell lysis buffer. The kit may include RNA isolation kit, substrates for labeling of RNA (may vary for various expression profiling techniques). The kit may also include materials for fluorescence microarray expression profiling, including one or more of the following: reverse transcriptase and 10×RT buffer, T7(dT)24 primer (primer with T7 promoter at 5' end), DTT, deoxynucleotides, optionally 100 mM each, RNAse inhibitor, second strand cDNA buffer, DNA polymerase, Rnase H, T7 RNA polymerase ribonucleotides, in vitro transcription buffer, and/or Cy3 and Cy5 labeled ribonucleotides. The kit may also include microarrays containing diagnostic gene libraries, cover slips for slides, and/or hybridization chambers. The kit may further include software package for identification of diagnostic gene set from data, that contains statistical methods, and/or allows alteration in desired sensitivity and specificity of gene set. The software may further facilitate access to and data analysis by centrally a located database server. The software may further include a password and account number to access central database server. In addition, the kit may include a kit user manual.

In another embodiment, the kit may include contents useful for the application of diagnostic oligonucleotide sets using microarrays. The kit may include sterile, endotoxin and/or RNAse free blood collection tubes. The kit may also include, alcohol swabs, tourniquet, and/or a blood collection set. The kit may further include PBS (phosphate buffer saline; needed when method of example 2 is used to derived mononuclear RNA), cell lysis buffer, and/or an RNA isolation kit. In addition, the kit may include substrates for labeling of RNA (may vary for various expression profiling techniques). For fluorescence microarray expression profiling, components may include reverse transcriptase and 10× RT buffer, T7(dT)24 primer (primer with T7 promoter at 5' end), DTT, deoxynucleotides (optionally 100 mM each), RNAse inhibitor, second strand cDNA buffer, DNA polymerase, Rnase H, T7 RNA polymerase, ribonucleotides, in vitro transcription buffer, and/or Cy3 and Cy5 labeled ribonucleotides. The kit may further include microarrays containing diagnostic gene libraries. The kit may also include cover slips for slides, and/or hybridization chambers. The kit may include a software package for identification of diagnostic gene set from data. The software package may contain statistical methods, allow alteration in desired sensitivity and specificity of gene set, and/or facilitate access to and data analysis by centrally located database server. The software package may include a password and account number to access central database server. In addition, the kit may include a kit user manual.

In another embodiment, the kit may include contents useful for the application of diagnostic oligonucleotide sets using real-time PCR. This kit may include terile, endotoxin and/or RNAse free blood collection tubes. The kit may further include alcohol swabs, tourniquet, and/or a blood collection set. The kit may also include PBS (phosphate buffer saline; needed when method of example 2 is used to derived mononuclear RNA). In addition, the kit may include cell lysis buffer and/or an RNA isolation kit. The kit may laso include substrates for real time RT-PCR, which may vary for various real-time PCR techniques, including poly dT primers, random hexamer primers, reverse Transcriptase and RT buffer, DTT, deoxynucleotides 100 mM, RNase H, primer pairs for diagnostic and control gene set, 10×PCR reaction buffer, and/or Taq DNA polymerase. The kit may also include fluorescent probes for diagnostic and control gene set (alternatively, fluorescent dye that binds to only double stranded DNA). The kit may further include reaction tubes with or without barcode for sample tracking, 96-well plates with barcode for sample identification, one barcode for entire set, or individual barcode per reaction tube in plate. The kit may also include a software package for identification of diagnostic gene set from data, and/or statistical methods. The software package may allow alteration in desired sensitivity and specificity of gene set, and/or facilitate access to and data analysis by centrally located database server. The kit may include a password and account number to access central database server. Finally, the kit may include a kit user manual.

This invention will be better understood by reference to the following non-limiting Examples:

List of Example Titles

Example 1: Discussion of data validating the four genes

Example 2: Preparation of RNA from mononuclear cells for expression profiling

Example 3: Preparation of Universal Control RNA for use in leukocyte expression profiling Example 4: Real-time PCR validation of array expression results Example 5: Correlation and Classification Analysis Example 6: Assay sample preparation Example 7: Detection of proteins expressed by diagnostic gene sequences

EXAMPLES

Example 1

Discussion of Data Validating the Four Genes

The four diagnostic genes disclosed herein were identified and validated using the methods described in the Examples section. This Example 1 summarizes the results of that validation. These four diagnostic genes may be used alone, with each other, or with additional diagnostic genes to monitor inflammation related disorders as described herein. The techniques described in these Examples as well as other techniques known to those of skill in the art may be used to identify diagnostic gene sets and diagnostic oligonucleotide sets that include the four diagnostic genes of the present invention that are particularly effective in monitoring various inflammation related disorders.

Definition of HR and Q.

"High-grade Rejection" (HR) for a sample is defined by an ISHLT biopsy rejection grade of 3A or greater (i.e. 3A, 3B or 4) as called by at least 2 of the 4 local and central cardiac pathologists "Quiescent" (Q) for a sample is defined by an ISHLT biopsy rejection grade of 0 as called by 3 of the 4 local and central cardiac pathologists, and no biopsy rejection grade above 0 for the period 3 weeks prior to 3 weeks after the current sample, and no current graft dysfunction (defined by PCW>20 or CI<2 or EF<40), and no biopsy rejection grade of 3A or greater within 3 months, and no rejection therapy administered within 3 months The Cardiac Allograft Rejection Gene Expression Observational study (CARGO) was initiated in 2001 to study the utility of peripheral blood gene expression for cardiac transplantation acute rejection management and to clinically validate gene expression testing in this population. A sensitive real-time Quantitative PCR technology, as described in Example 4, was used to measure gene expression levels of roughly 250 genes on a set of 36 High Grade Acute Rejection (HR) and 109 Quiescent samples (Q) chosen from the CARGO study. The Study provided quantitative and reproducible measures of gene expression levels for these genes and this data was used to identify gene expression patterns in peripheral blood that correlated with acute rejection.

Characteristics of the Study Population:

As shown in the following table, several factors could have affected the gene expression profiles in a given sample including the age of the patient, Days post transplant, Days followed after the collection of peripheral blood, Cyclosporine and FK-506 dose. Therefore, selection of the Q and HR samples was carefully balanced so that these factors are not statistically significant to rule out any effects of these factors on gene expression patterns in peripheral blood.

|  | Mean Q | Mean HR | t-value | df | p |
|---|---|---|---|---|---|
| AgeAtVisit | 55.624 | 53.861 | 0.77617 | 143 | 0.438929 |
| DaysPostTx | 206.294 | 253.861 | −0.59938 | 143 | 0.549869 |
| DaysFollowed | 251.294 | 286.944 | −1.02756 | 143 | 0.305890 |
| Cyclosporine | 408.333 | 406.579 | 0.01841 | 65 | 0.985371 |
| FK-506 | 72.873 | 5.765 | 0.52946 | 74 | 0.598073 |

|  | Valid N Q | Valid N HR | Std.Dev. Q | Std.Dev. HR |
|---|---|---|---|---|
| AgeAtVisit | 109 | 36 | 11.7944 | 11.8759 |
| DaysPostTx | 109 | 36 | 408.3182 | 426.5220 |
| DaysFollowed | 109 | 36 | 176.5282 | 192.1832 |
| Cyclosporine | 48 | 19 | 400.3766 | 167.2577 |
| FK-506 | 59 | 17 | 520.0967 | 5.0686 |

Correlation of Expression of Genes with Acute Rejection

As shown in the following table, the four diagnostic genes of the present invention can significantly distinguish biopsy-proven HR, defined by a 3A or greater ISHLT grade, from Q, defined by a 0 ISHLT grade, both grades determined by both local and centralized cardio-pathological examination.

|  | Mean Q | Mean HR | t-value | df | p |
|---|---|---|---|---|---|
| SIRPB1 | 27.887 | 28.236 | −3.04149 | 143 | 0.002801 |
| S100A9 | 22.003 | 22.431 | −2.62285 | 143 | 0.009665 |
| ZNFN1A | 26.916 | 26.704 | 3.90105 | 143 | 0.000147 |
| IGJ | 30.58960 | 29.99403 | 2.409554 | 143 | 0.017244 |

|  | Valid N Q | Valid N HR | Std.Dev. Q | Std.Dev. HR |
|---|---|---|---|---|
| SIRPB1 | 109 | 36 | 0.6040 | 0.5749 |
| S100A9 | 109 | 36 | 0.8896 | 0.7030 |
| ZNFN1A | 109 | 36 | 0.3025 | 0.2099 |
| IGJ | 109 | 36 | 1.279300 | 1.305704 |

In the above table, SIRPB1 is the diagnostic gene corresponding to SEQ ID NO:5; S100A9 is the diagnostic gene corresponding to SEQ ID NO:11; ZNFN1A is the diagnostic gene corresponding to SEQ ID NO:17; and IGJ is the diagnostic gene corresponding to SEQ ID NO:23. Mean Q is the mean Ct for the diagnostic gene in the Quiescent samples. Mean HR is the mean Ct for the diagnostic gene in the High Grade Acute Rejection samples.

Example 2

Preparation of RNA from Mononuclear Cells for Expression Profiling

Blood was isolated from the subject for leukocyte expression profiling using the following methods:

Two tubes were drawn per patient. Blood was drawn from either a standard peripheral venous blood draw or directly from a large-bore intra-arterial or intravenous catheter inserted in the femoral artery, femoral vein, subclavian vein or internal jugular vein. Care was taken to avoid sample contamination with heparin from the intravascular catheters, as heparin can interfere with subsequent RNA reactions.

For each tube, 8 ml of whole blood was drawn into a tube (CPT, Becton-Dickinson order #362753) containing the anti-coagulant Citrate, 25° C. density gradient solution (e.g. Ficoll, Percoll) and a polyester gel barrier that upon centrifugation was permeable to RBCs and granulocytes but not to mononuclear cells. The tube was inverted several times to mix the blood with the anticoagulant. The tubes were centrifuged at 1750×g in a swing-out rotor at room temperature for 20 minutes. The tubes were removed from the centrifuge and inverted 5-10 times to mix the plasma with the mononuclear cells, while trapping the RBCs and the granulocytes beneath the gel barrier. The plasma/mononuclear cell mix was decanted into a 15 ml tube and 5 ml of phosphate-buffered saline (PBS) is added. The 15 ml tubes were spun for 5 minutes at 1750×g to pellet the cells. The supernatant was discarded and 1.8 ml of RLT lysis buffer is added to the mononuclear cell pellet. The buffer and cells were pipetted up and down to ensure complete lysis of the pellet. The cell lysate was frozen and stored until it is convenient to proceed with isolation of total RNA.

Total RNA was purified from the lysed mononuclear cells using the Qiagen Rneasy Miniprep kit, as directed by the manufacturer (10/99 version) for total RNA isolation, including homogenization (Qiashredder columns) and on-column DNase treatment. The purified RNA was eluted in 50 ul of water. Some samples were prepared by a different protocol, as follows:

Two 8 ml blood samples were drawn from a peripheral vein into a tube (CPT, Becton-Dickinson order #362753) containing anticoagulant (Citrate), 25° C. density gradient solution (Ficoll) and a polyester gel barrier that upon centrifugation is permeable to RBCs and granulocytes but not to mononuclear cells. The mononuclear cells and plasma remained above the barrier while the RBCs and granulocytes were trapped below. The tube was inverted several times to mix the blood with the anticoagulant, and the tubes were subjected to centrifugation at 1750×g in a swing-out rotor at room temperature for 20 min. The tubes were removed from the centrifuge, and the clear plasma layer above the cloudy mononuclear cell layer was aspirated and discarded. The cloudy mononuclear cell layer was aspirated, with care taken to rinse all of the mononuclear cells from the surface of the gel barrier with PBS (phosphate buffered saline). Approximately 2 mls of mononuclear cell suspension was transferred to a 2 ml microcentrifuge tube, and centrifuged for 3 min. at 16,000 rpm in a microcentrifuge to pellet the cells. The supernatant was discarded and 1.8 ml of RLT lysis buffer (Qiagen) were added to the mononuclear cell pellet, which lysed the cells and inactivated Rnases. The cells and lysis buffer were pipetted up and down to ensure complete lysis of the pellet. Cell lysate was frozen and stored until it was convenient to proceed with isolation of total RNA.

RNA samples were isolated from 8 mL of whole blood. Yields ranged from 2 ug to 20 ug total RNA for 8 mL blood. A260/A280 spectrophotometric ratios were between 1.6 and 2.0, indicating purity of sample. 2 ul of each sample were run on an agarose gel in the presence of ethidium bromide. No degradation of the RNA sample and no DNA contamination was visible.

In some cases, specific subsets of mononuclear cells were isolated from peripheral blood of human subjects. When this was done, the StemSep cell separation kits (manual version 6.0.0) were used from StemCell Technologies (Vancouver, Canada). This same protocol can be applied to the isolation of T cells, CD4 T cells, CD8 T cells, B cells, monocytes, NK cells and other cells. Isolation of cell types using negative selection with antibodies may be desirable to avoid activation of target cells by antibodies.

Example 3

Preparation of Universal Control RNA for use in Leukocyte Expression Profiling

Control RNA was prepared using total RNA from Buffy coats and/or total RNA from enriched mononuclear cells isolated from Buffy coats, both with and without stimulation with ionomycin and PMA. The following control RNAs were prepared:

Control 1: Buffy Coat Total RNA

Control 2: Mononuclear cell Total RNA

Control 3: Stimulated buffy coat Total RNA

Control 4: Stimulated mononuclear Total RNA

Control 5: 50% Buffy coat Total RNA/50% Stimulated buffy coat Total RNA

Control 6: 50% Mononuclear cell Total RNA/50% Stimulated Mononuclear Total RNA

Some samples were prepared using the following protocol: Buffy coats from 38 individuals were obtained from Stanford Blood Center. Each buffy coat is derived from ~350 mL whole blood from one individual. 10 ml buffy coat was removed from the bag, and placed into a 50 ml tube. 40 ml of Buffer EL (Qiagen) was added, the tube was mixed and placed on ice for 15 minutes, then cells were pelleted by centrifugation at 2000×g for 10 minutes at 4° C. The supernatant was decanted and the cell pellet was re-suspended in 10 ml of Qiagen Buffer EL. The tube was then centrifuged at 2000×g for 10 minutes at 4° C. The cell pellet was then re-suspended in 20 ml TRIZOL (GibcoBRL) per Buffy coat sample, the mixture was shredded using a rotary homogenizer, and the lysate was then frozen at −80° C. prior to proceeding to RNA isolation.

Other control RNAs were prepared from enriched mononuclear cells prepared from Buffy coats. Buffy coats from Stanford Blood Center were obtained, as described above. 10 ml buffy coat was added to a 50 ml polypropylene tube, and 10 ml of phosphate buffer saline (PBS) was added to each tube. A polysucrose (5.7 g/dL) and sodium diatrizoate (9.0 g/dL) solution at a 1.077+/−0.0001 g/ml density solution of equal volume to diluted sample was prepared (Histopaque 1077, Sigma cat. no 1077-1). This and all subsequent steps were performed at room temperature. 15 ml of diluted buffy coat/PBS was layered on top of 15 ml of the histopaque solution in a 50 ml tube. The tube was centrifuged at 400×g for 30 minutes at room temperature. After centrifugation, the upper layer of the solution to within 0.5 cm of the opaque interface containing the mononuclear cells was discarded. The opaque interface was transferred into a clean centrifuge tube. An equal volume of PBS was added to each tube and centrifuged at 350×g for 10 minutes at room temperature. The supernatant was discarded. 5 ml of Buffer EL (Qiagen) was used to resuspend the remaining cell pellet and the tube was centrifuged at 2000×g for 10 minutes at room temperature. The supernatant was discarded. The pellet was resuspended in 20 ml of TRIZOL (GibcoBRL) for each individual buffy coat that was processed. The sample was homogenized using a rotary homogenizer and frozen at −80 C until RNA was isolated.

RNA was isolated from frozen lysed Buffy coat samples as follows: frozen samples were thawed, and 4 ml of chloroform was added to each buffy coat sample. The sample was mixed by vortexing and centrifuged at 2000×g for 5 minutes. The aqueous layer was moved to new tube and then repurified by using the RNeasy Maxi RNA clean up kit, according to the manufacturer's instruction (Qiagen, PN 75162). The yield, purity and integrity were assessed by spectrophotometer and gel electrophoresis.

Some samples were prepared by a different protocol, as follows.

50 whole blood samples were randomly selected from consented blood donors at the Stanford Medical School Blood Center. Each buffy coat sample was produced from ~350 mL of an individual's donated blood. The whole blood sample was centrifuged at ~4,400×g for 8 minutes at room temperature, resulting in three distinct layers: a top layer of plasma, a second layer of buffy coat, and a third layer of red blood cells. 25 ml of the buffy coat fraction was obtained and diluted with an equal volume of PBS (phosphate buffered saline). 30 ml of diluted buffy coat was layered onto 15 ml of sodium diatrizoate solution adjusted to a density of 1.077±0.001 g/ml (Histopaque 1077, Sigma) in a 50 mL plastic tube. The tube was spun at 800 g for 10 minutes at room temperature. The plasma layer was removed to the 30 ml mark on the tube, and the mononuclear cell layer removed into a new tube and washed with an equal volume of PBS, and collected by centrifugation at 2000 g for 10 minutes at room temperature. The cell pellet was resuspended in 10 ml of Buffer EL (Qiagen) by vortexing and incubated on ice for 10 minutes to remove any remaining erthythrocytes. The mononuclear cells were spun at 2000 g for 10 minutes at 4 degrees Celsius. The cell pellet was lysed in 25 ml of a phenol/guanidinium thiocyanate solution (TRIZOL Reagent, Invitrogen). The sample was homogenized using a PowerGene 5 rotary homogenizer (Fisher Scientific) and Omini disposable generator probes (Fisher Scientific). The Trizol lysate was frozen at −80 degrees C. until the next step.

The samples were thawed out and incubated at room temperature for 5 minutes. 5 ml chloroform was added to each sample, mixed by vortexing, and incubated at room temperature for 3 minutes. The aqueous layers were transferred to new 50 ml tubes. The aqueous layer containing total RNA was further purified using the Qiagen RNeasy Maxi kit (PN 75162), per the manufacturer's protocol (October 1999). The columns were eluted twice with 1 ml Rnase-free water, with a minute incubation before each spin. Quantity and quality of RNA was assessed using standard methods. Generally, RNA was isolated from batches of 10 buffy coats at a time, with an average yield per buffy coat of 870 µg, and an estimated total yield of 43.5 mg total RNA with a 260/280 ratio of 1.56 and a 28S/18S ratio of 1.78.

Quality of the RNA was tested using the Agilent 2100 Bioanalyzer using RNA 6000 microfluidics chips. Analysis of the electrophorgrams from the Bioanalyzer for five different batches demonstrated the reproducibility in quality between the batches.

Total RNA from all five batches were combined and mixed in a 50 ml tube, then aliquoted as follows: 2×10 ml aliquots in 15 ml tubes, and the rest in 100 µl aliquots in 1.5 ml microcentrifuge tubes. The aliquots gave highly reproducible results with respect to RNA purity, size and integrity. The RNA was stored at −80° C.

Example 4

Real-Time PCR Validation of Array Expression Results

While gene expression may be measured using a microarray especially for identifying and validating different sets of diagnostic genes, it is desirable to further validate the gene expression results for each diagnostic gene or set of diagnostic genes using a more sensitive and quantitative technology such as real-time PCR. Further, it is possible for the diagnostic oligonucleotide sets to be implemented as a diagnostic test as a real-time PCR panel. Alternatively, the quantitative information provided by real-time PCR validation can be used to design a diagnostic test using any alternative quantitative or semi-quantitative gene expression technology. The following example demonstrates one example of such validation.

To validate the results of various microarray experiments we used real-time, or kinetic, PCR. In this type of experiment the amplification product is measured during the PCR reaction. This enables the researcher to observe the amplification before any reagent becomes rate limiting for amplification. In kinetic PCR the measurement is of $C_T$ (threshold cycle) or $C_P$ (crossing point). This measurement ($C_T=C_P$) is the point at which an amplification curve crosses a threshold fluorescence value. The threshold is set to a point within the area where all of the reactions were in their linear phase of amplification. When measuring $C_T$, a lower $C_T$ value is indicative of a higher amount of starting material since an earlier cycle number means the threshold was crossed more quickly.

Several fluorescence methodologies are available to measure amplification product in real-time PCR. Taqman (Applied BioSystems, Foster City, Calif.) uses fluorescence resonance energy transfer (FRET) to inhibit signal from a probe until the probe is degraded by the sequence specific binding and Taq 3' exonuclease activity. Molecular Beacons (Stratagene, La Jolla, Calif.) also use FRET technology, whereby the fluorescence is measured when a hairpin structure is relaxed by the specific probe binding to the amplified DNA. The third commonly used chemistry is Sybr Green, a DNA-binding dye (Molecular Probes, Eugene, Oreg.). The more amplified product that is produced, the higher the signal. The Sybr Green method is sensitive to non-specific amplification products, increasing the importance of primer design and selection. Other detection chemistries can also been used, such as ethedium bromide or other DNA-binding dyes and many modifications of the fluorescent dye/quencher dye Taqman chemistry.

Sample Prep and cDNA Synthesis

The inputs for real time PCR reaction are gene-specific primers, cDNA from specific patient samples, and standard reagents. The cDNA was produced from mononuclear RNA (prepared as in example 2) or whole blood RNA by reverse transcription using Oligo dT primers (Invitrogen, 18418-012) and random hexamers (Invitrogen, 48190-011) at a final concentration of 0.5 ng/µl and 3 ng/µl respectively. For the first strand reaction mix, 0.5 µg of mononuclear total RNA or 2 µg of whole blood RNA and 1 µl of the Oligo dT/Random Hexamer Mix, were added to water to a final volume of 11.5 µl. The sample mix was then placed at 70° C. for 10 minutes. Following the 70° C. incubation, the samples were chilled on ice, spun down, and 88.5 µl of first strand buffer mix dispensed into the reaction tube. The final first strand buffer mix produced final concentrations of 1× first strand buffer (Invitrogen, Y00146, Carlsbad, Calif.), 10 mM DTT (Invitrogen, Y00147), 0.5 mM dATP (NEB, N0440S, Beverly, Mass.), 0.5 mM dGTP (NEB, N0442S), 0.5 mM dTTP (NEB, N0443S), 0.5 mM dCTP (NEB, N0441S), 200 U of reverse transcriptase (Superscript II, Invitrogen, 18064-014), and 18 U of RNase inhibitor (RNAGaurd Amersham Pharmacia, 27-0815-01, Piscataway, N.J.). The reaction was incubated at 42° C. for 90 minutes. After incubation the enzyme was heat inactivated at 70° C. for 15 minutes, 2 U of RNAse H added to the reaction tube, and incubated at 37° C. for 20 minutes.

Primer Design

Two methods were used to design primers. The first was to use the software, Primer Express™ and recommendations for primer design that are provided with the GeneAmp® 7700 Sequence Detection System supplied by Applied BioSystems (Foster City, Calif.). The second method used to design primers was the PRIMER3 ver 0.9 program that is available from the Whitehead Research Institute, Cambridge, Mass. at the Whitehead Research web site. The program can also be accessed on the World Wide Web at the web site at the Massechusetts Institute of Technology website. Primers and Taqman/hybridization probes were designed as described below using both programs.

The Primer Express literature explains that primers should be designed with a melting temperature between 58 and 60 degrees C. while the Taqman probes should have a melting temperature of 68 to 70 under the salt conditions of the supplied reagents. The salt concentration is fixed in the software. Primers should be between 15 and 30 basepairs long. The primers should produce and amplicon in size between 50 and 150 base pairs, have a C-G content between 20% and 80%, have no more than 4 identical base pairs next to one another, and no more than 2 C's and G's in the last 5 bases of the 3' end. The probe cannot have a G on the 5' end and the strand with the fewest G's should be used for the probe.

Primer3 has a large number of parameters. The defaults were used for all except for melting temperature and the optimal size of the amplicon was set at 100 bases. One of the most critical is salt concentration as it affects the melting temperature of the probes and primers. In order to produce primers and probes with melting temperatures equivalent to Primer Express, a number of primers and probes designed by Primer Express were examined using PRIMER3. Using a salt concentration of 50 mM these primers had an average melting temperature of 3.7 degrees higher than predicted by Primer Express. In order to design primers and probes with equivalent melting temperatures as Primer Express using PRIMER3, a melting temperature of 62.7 plus/minus 1.0 degree was used in PRIMER3 for primers and 72.7 plus/minus 1.0 degrees for probes with a salt concentration of 50 mM.

The C source code for Primer3 was downloaded and complied on a Sun Enterprise 250 server using the GCC complier. The program was then used from the command line using a input file that contained the sequence for which we wanted to design primers and probes along with the input parameters as described by help files that accompany the software. Using scripting it was possible to input a number of sequences and automatically generate a number of possible probes and primers. Primers for β-Actin (Beta Actin, Genbank Locus: NM_001101) and β-GUS: glucuronidase, beta, (GUSB, Genbank Locus: NM_000181), two reference genes, were designed using both methods and are shown here as examples:

The first step was to mask out repetitive sequences found in the mRNA sequences using RepeatMasker program that can be accessed at: the web site University of Washington Genome Repeatmasker website. (Smit, A. F. A. & Green, P.).

The last 500 basepairs on the last 3' end of masked sequence was then submitted to PRIMER3 using the following exemplary input sequences:

(SEQ ID NO:25)
PRIMER_SEQUENCE_ID => ACTB Beta Actin

SEQUENCE = TTGGCTTGACTCAGGATTTAAAAACTGGAACGGTGAAGG

TGACAGCAGTCGGTTGGACGAGCATCCCCCAAAGTTCACAATGTGGCCGA

GGACTTTGATTGCACATTGTTGTTTTTTAATAGTCATTCCAAATATGAGA

TGCATTGTTACAGGAAGTCCCTTGCCATCCTAAAAGCACCCCACTTCTCT

CTAAGGAGAATGGCCCAGTCCTCTCCCAAGTCCACACAGGGGAGGGATAG

CATTGCTTTCGTGTAAATTATGTAATGCAAAATTTTTTAATCTTCGCCT

TAATCTTTTTATTTTGTTTTATTTTGAATGATGAGCCTTCGTGCCCCCC

CTTCCCCCTTTTTCCCCCAACTTGAGATGTATGAAGGCTTTTGGTCTCC

CTGGGAGTGGGTGGAGGCAGCCGGGCTTACCTGTACACTGACTTGAGACC

AGTTGAATAAAAGTGCACACCTTA (SEQ ID NO:26)
PRIMER_SEQUENCE_ID => GUSB

SEQUENCE = GAAGAGTACCAGAAAAGTCTGCTAGAGCAGTACCATCTG

GGTCTGGATCAAAAACGCAGAAAATATGTGGTTGGAGAGCTCATTTGGAA

TTTTGCCGATTTCATGACTGAACAGTCACCGACGAGAGTGCTGGGAATA

AAAAGGGGATCTTCACTCGGCAGAGACAACCAAAAAGTGCAGCGTTCCTT

TTGCGAGAGAGATACTGGAAGATTGCCAATGAAACCAGGTATCCCCACTC

AGTAGCCAAGTCACAATGTTTGGAAAACAGCCCGTTTACTTGAGCAAGAC

TGATACCACCTGCGTGTCCCTTCCTCCCCGAGTCAGGGCGACTTCCACAG

CAGCAGAACAAGTGCCTCCTGGACTGTTCACGGCAGACCAGAACGTTTCT

GGCCTGGGTTTTGTGGTCATCTATTCTAGCAGGGAACACTAAAGGTGGAA

ATAAAAGATTTTCTATTATGGAAATAAAGAGTTGGCATGAAAGTCGCTAC

TG

After running PRIMER3, 100 sets of primers and probes were generated for ACTB and GUSB. From this set, nested primers were chosen based on whether both left primers could be paired with both right primers and a single Taqman probe could be used on an insert of the correct size. With more experience we have decided not use the mix and match approach to primer selection and just use several of the top pairs of predicted primers.

For ACTB this turned out to be:

Forward 75 CACAATGTGGCCGAGGACTT(SEQ ID NO:27),

Forward 80 TGTGGCCGAGGACTTTGATT(SEQ ID NO:28),

Reverse 178 TGGCTTTTAGGATGGCAAGG(SEQ ID NO:29), and

Reverse 168 GGGGGCTTAGTTTGCTTCCT(SEQ ID NO:30).

Upon testing, the F75 and R178 pair worked best.

For GUSB the following primers were chosen:

Forward 59 AAGTGCAGCGTTCCTTTTGC(SEQ ID NO:31),

Forward 65 AGCGTTCCTTTTGCGAGAGA (SEQ ID NO:32),

Reverse 158 CGGGCTGTTTTCCAAACATT (SEQ ID NO:33), and

Reverse 197 GAAGGGACACGCAGGTGGTA (SEQ ID NO:34).

No combination of these GUSB pairs worked well.

In addition to the primer pairs above, Primer Express predicted the following primers for GUSB: Forward 178 TACCACCTGCGTGTCCCTTC (SEQ ID NO:35) and Reverse 242 GAGGCACTTGTTCTGCTGCTG (SEQ ID NO:36). This pair of primers worked to amplify the GUSB mRNA.

The parameters used to predict these primers in Primer Express were:

Primer Tm: min 58, Max=60, opt 59, max difference=2 degrees

Primer GC: min=20% Max=80% no 3' G/C clamp

Primer: Length: min=9 max=40 opt=20

Amplicon: min Tm=0 max Tm=85 min=50 bp max=150 bp

Probe: Tm 10 degrees>primers, do not begin with a G on 5' end

Other: max base pair repeat=3 max number of ambiguous residues=0 secondary structure: max consecutive bp=4, max total bp=8

Uniqueness: max consecutive match=9 max % match=75 max 3' consecutive match=7

Granzyme B is a marker of transplant rejection.

For Granzyme B the following sequence (NM_004131) (SEQ ID NO:37) was used as input for Primer3:

GGGGACTCTGGAGGCCCTCTTGTGTGTAACAAGGTGGCCCAGGGCATTGT

CTCCTATGGACGAAACAATGGCATGCCTCCACGAGCCTGCACCAAAGTCT

CAAGCTTTGTACACTGGATAAAGAAAACCATGAAACGCTACTAACTACAG

GAAGCAAACTAAGCCCCGCTGTAATGAAACACCTTCTCTGGAGCCAAGT

CCAGATTTACACTGGGAGAGGTGCCAGCAACTGAATAAATACCTCTCCCA

GTGTAAATCTGGAGCCAAGTCCAGATTTACACTGGGAGAGGTGCCAGCAA

CTGAATAAATACCTCTTAGCTGAGTGG

For Granzyme B the following primers were chosen for testing:

Forward 81 ACGAGCCTGCACCAAAGTCT (SEQ ID NO: 38)

Forward 63 AAACAATGGCATGCCTCCAC (SEQ ID NO: 39)

Reverse 178 TCATTACAGCGGGGGCTTAG (SEQ ID NO:40)

Reverse 168 GGGGGCTTAGTTTGCTTCCT (SEQ ID NO:41)

Testing demonstrated that F81 and R178 worked well.

Using this approach, primers were designed for all the genes that were shown to have expression patterns that correlated with allograft rejection. Primers can be designed from any region of a target gene using this approach.

Primer Endpoint Testing

Primers were first tested to examine whether they would produce the correct size product without non-specific amplification. The standard real-time PCR protocol was used without the Rox and Sybr green dyes. Each primer pair was tested on cDNA made from universal mononuclear leukocyte reference RNA that was produced from 50 individuals as described in Example 3 (R50).

The PCR reaction consisted of 1× RealTime PCR Buffer (Ambion, Austin, Tex.), 2 mM MgCl2 (Applied BioSystems, B02953), 0.2 mM dATP (NEB), 0.2 mM dTTP (NEB), 0.2 mM dCTP (NEB), 0.2 mM dGTP (NEB), 0.625 U AmpliTaq Gold (Applied BioSystems, Foster City, Calif.), 0.3 μM of each primer to be used (Sigma Genosys, The Woodlands, Tex.), 5 μl of the R50 reverse-transcription reaction and water to a final volume of 19 μl.

Following 40 cycles of PCR, 10 microliters of each product was combined with Sybr green at a final dilution of 1:72,000. Melt curves for each PCR product were determined on an ABI 7900 (Applied BioSystems, Foster City, Calif.), and primer pairs yielding a product with one clean peak were chosen for further analysis. One microliter of the product from these primer pairs was examined by agarose gel electrophoresis on an Agilent Bioanalyzer, DNA1000 chip (Palo Alto, Calif.). Results for 2 genes are shown in FIG. 1. From the primer design and the sequence of the target gene, one can calculate the expected size of the amplified DNA product. Only primer pairs with amplification of the desired product and minimal amplification of contaminants were used for real-time PCR. Primers that produced multiple products of different sizes are likely not specific for the gene of interest and may amplify multiple genes or chromosomal loci.

Primer Optimization Efficiency

Once primers passed the end-point PCR, the primers were tested to determine the efficiency of the reaction in a real-time PCR reaction. cDNA was synthesized from starting total RNA as described above. A set of 5 serial dilutions of the R50 reverse-transcribed cDNA (as described above) were made in water: 1:10, 1:20, 1:40, 1:80, and 1:160.

The Sybr Green real-time PCR reaction was performed using the Taqman PCR Reagent kit (Applied BioSystems, Foster City, Calif., N808-0228). A master mix was made that consisted of all reagents except the primes and template. The final concentration of all ingredients in the reaction was 1× Taqman Buffer A (Applied BioSystems), 2 mM MgCl2 (Applied BioSystems), 200 μM dATP (Applied BioSystems), 200 μM dCTP (Applied BioSystems), 200 μM dGTP (Applied BioSystems), 400 μM dUTP (Applied BioSystems), 1:400,000 diluted Sybr Green dye (Molecular Probes), 1.25 U AmpliTaq Gold (Applied BioSystems). The PCR master mix was dispensed into two, light-tight tubes. Each β-Actin primer F75 and R178 (Sigma-Genosys, The Woodlands, Tex.), was added to one tube of PCR master mix and Each β-GUS primer F178 and R242 (Sigma-Genosys), was added to the other tube of PCR master mix to a final primer concentration of 300 nM. 45 μl of the β-Actin or β-GUS master mix was dispensed into wells, in a 96-well plate (Applied BioSystems). 5 μl of the template dilution series was dispensed into triplicate wells for each primer. The reaction was run on an ABI 7900 Sequence Detection System (Applied BioSystems) with the following conditions: 10 min. at 95° C.; 40 cycles of 95° C. for 15 sec, 60° C. for 1 min; following disassociation curve starting at 50° C. and ending at 95° C.

The Sequence Detection System v2.0 software was used to analyze the fluorescent signal from each well. The high end of the baseline was adjusted to between 8 and 20 cycles to reduce the impact on any data curves, yet be as high as possible to reduce baseline drift. A threshold value was selected that allowed the majority of the amplification curves to cross the threshold during the linear phase of amplification. The disassociation curve for each well was compared to other wells for that marker. This comparison allowed identification of "bad" wells, those that did not amplify, that amplified the wrong size product, or that amplified multiple products. The cycle number at which each amplification curve crossed the threshold ($C_T$) was recorded and the file transferred to MS Excel for further analysis. The $C_T$ values for triplicate wells were averaged. The data were plotted as a function of the $\log_{10}$ of the calculated starting concentration of RNA. The starting RNA concentration for each cDNA dilution was determined based on the original amount of RNA used in the RT reaction, the dilution of the RT reaction, and the amount used (5 μl) in the real-time PCR reaction. For each gene, a linear regression line was plotted through all of the dilutions series points. The slope of the line was used to calculate the efficiency of the reaction for each primer set using the equation:

$$E = 10^{\left(\frac{-1}{slope}\right)} - 1$$

Figure 2:
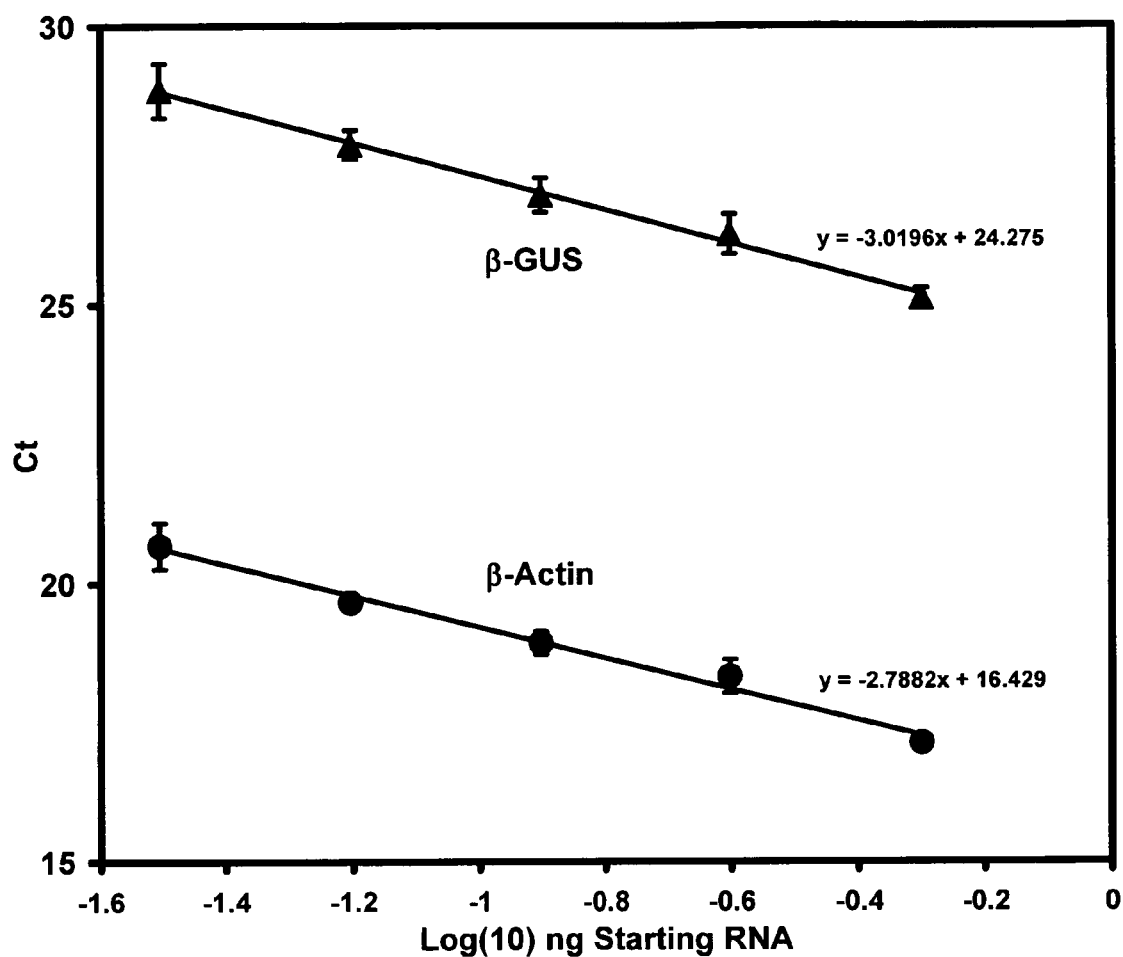
FIG. 2 shows PCR Primer efficiency testing. A standard curve of Ct versus log of the starting RNA amount is shown for 2 genes, β-GUS and β-Actin

Using this equation (Pfaffl 2001, Applied Biosystems User Bulletin #2), the efficiency for these 13-actin primers is 1.28 and the efficiency for these β-GUS primers is 1.14 (FIG. 2). This efficiency was used when comparing the expression levels among multiple genes and multiple samples. This same method was used to calculate reaction efficiency for primer pairs for each gene studied. A primer pair was considered successful if the efficiency was reproducibly determined to be between 0.7 and 2.4.

Sybr Green Assays

Once markers passed the Primer Efficiency QPCR (as stated above), they were used in real-time PCR assays. Patient RNA samples were reverse-transcribed to cDNA (as described above) and 1:10 dilutions made in water. In addition to the patient samples, a no template control (NTC) and a pooled reference RNA (see example 2) described in were included on every plate.

The Sybr Green real-time PCR reaction was performed using the Taqman Core PCR Reagent kit (Applied BioSystems, Foster City, Calif., N808-0228). A master mix was made that consisted of all reagents except the primers and template. The final concentration of all ingredients in the reaction was 1× Taqman Buffer A (Applied BioSystems), 2 mM MgCl2 (Applied BioSystems), 200 μM dATP (Applied BioSystems), 200 μM dCTP (Applied BioSystems), 200 μM dGTP (Applied BioSystems), 400 μM dUTP (Applied BioSystems), 1:400,000 diluted Sybr Green dye (Molecular Probes), 1.25 U AmpliTaq Gold (Applied BioSystems). The PCR master mix was aliquotted into eight light-tight tubes, one for each marker to be examined across a set of samples. The optimized primer pair for each marker was then added to the PCR master mix to a final primer concentration of 300 nM. 18 μl of the each marker master mix was dispensed into wells in a 384 well plate (Applied BioSystems). 2 μl of the 1:10 diluted control or patient cDNA sample was dispensed into triplicate wells for each primer pair. The reaction was run on an ABI 7900 Sequence Detection System (Applied BioSystems) using the cycling conditions described above.

The Sequence Detection System v2.0 software (Applied BioSystems) was used to analyze the fluorescent signal from each well. The high end of the baseline was adjusted to between 8 and 20 cycles to reduce the impact on any data curves, yet be as high as possible to reduce baseline drift. A threshold value was selected that allowed the majority of the amplification curves to cross the threshold during the linear phase of amplification. The disassociation curve for each well was compared to other wells for that marker. This comparison allowed identification of "bad" wells, those that did not amplify, that amplified the wrong size product, or that amplified multiple products. The cycle number at which each amplification curve crossed the threshold ($C_T$) was recorded and the file transferred to MS Excel for further analysis. The $C_T$ value representing any well identified as bad by analysis of disassociation curves was deleted. The $C_T$ values for triplicate wells were averaged. A standard deviation (Stdev) and a coefficient of variation (CV) were calculated for the triplicate wells. If the CV was greater than 2, an outlier among the three wells was identified and deleted. Then the average was re-calculated. In each plate, $\Delta C_T$ was calculated for each marker-control combination by subtracting the average $C_T$ of the target marker from the average $C_T$ of the control (β-Actin or β-GUS). The expression relative to the control marker was calculated by taking two to the power of the $\Delta C_T$ of the target marker. For example, expression relative to β-Actin was calculated by the equation:

$$ErA = 2^{(C_{T,Actin} - C_{T,target})}$$

All plates were run in duplicate and analyzed in the same manner. The percent variation was determined for each sample-marker combination (relative expression) by taking the absolute value of the value of the RE for the second plate from the RE for the first plate, and dividing that by the average. If more than 25% of the variation calculations on a plate are greater than 50%, then a third plate was run.

Taqman Protocol

Real-time PCR assays were also done using Taqman PCR chemistry.

The Taqman real-time PCR reaction was performed using the Taqman Universal PCR Master Mix (Applied BioSystems, Foster City, Calif., #4324018). The master mix was aliquoted into eight, light-tight tubes, one for each marker. The optimized primer pair for each marker was then added to the correctly labeled tube of PCR master mix. A FAM/TAMRA dual-labeled Taqman probe (Biosearch Technologies, Navoto, Calif., DLO-FT-2) was then added to the correctly labeled tube of PCR master mix. Alternatively, different combinations of fluorescent reporter dyes and quenchers can be used such that the absorption wavelength for the quencher matches the emission wavelength for the reporter, as shown in Table 3. 18 μl of the each marker master mix was dispensed into a 384 well plate (Applied BioSystems). 2 μl of the template sample was dispensed into triplicate wells for each primer pair. The final concentration of each reagent was: 1× TaqMan Universal PCR Master Mix, 300 nM each primer, 0.25 nM probe, 2 μl 1:10 diluted template. The reaction was run on an ABI 7900 Sequence Detection System (Applied Biosystems) using standard conditions (95° C. for 10 min., 40 cycles of 95° C. for 15 sec, 60° C. for 1 min.).

TABLE 3

| Reporter | Quencher |
|----------|----------|
| FAM | TAMRA |
|  | BHQ1 |
| TET | TAMRA |
|  | BHQ1 |
| JOE | TAMRA |
|  | BHQ1 |
| HEX | TAMRA |
|  | BHQ1 |
| VIC | TAMRA |
|  | BHQ1 |
| ROX | BHQ2 |
| TAMRA | BHQ2 |

The Sequence Detector v2.0 software (Applied BioSystems) was used to analyze the fluorescent signal from each well. The high end of the baseline was adjusted to between 8 and 20 cycles to reduce the impact on any data curves, yet be as high as possible to reduce baseline drift. A threshold value was selected that allowed most of the amplification curves to cross the threshold during the linear phase of amplification. The cycle number at which each amplification curve crossed the threshold ($C_T$) was recorded and the file transferred to MS Excel for further analysis. The $C_T$ values for triplicate wells were averaged. A standard deviation (Stdev) and a coefficient of variation (CV) were calculated for the triplicate wells. If the CV was greater than 2, an outlier among the three wells was identified and deleted. Then the average was re-calculated. In each plate, $\Delta C_T$ was calculated for each marker-control combination by subtracting the average $C_T$ of the target marker from the average $C_T$ of the control (β-Actin or β-GUS). The expression relative to the control marker was calculated by taking two to the power of the $\Delta C_T$ of the target marker. All plates were run in duplicate and analyzed in the same manner. The percent variation was determined for each sample-marker combination (relative expression) by taking the absolute value of the value of the RE for the second plate from the RE for the first plate, and dividing that by the average. If more than 25% of the variation calculations on a plate are greater than 50%, then a third plate was run.

Bi-Plexing

Variation of real-time PCR assays can arise from unequal amounts of RNA starting material between reactions. In some assays, to reduce variation, the control gene amplification was included in the same reaction well as the target gene. To differentiate the signal from the two genes, different fluorescent dyes were used for the control gene. β-Actin was used as the control gene and the TaqMan probe used was labeled with the fluorescent dye VIC and the quencher TAMRA (Biosearch Technologies, Navoto, Calif., DLO-FT-2). Alternatively, other combinations of fluorescent reporter dyes and quenchers (Table 3) can be used as long as the emission wavelength of the reporter for the control gene is sufficiently different from the wavelength of the reporter dye used for the target. The control gene primers and probe were used at limiting concentrations in the reaction (150 nM primers and 0.125 nM probe) to ensure that there were enough reagents to amplify the target marker. The plates were run under the same protocol and the data are analyzed in the same way, but with a separate baseline and threshold for the VIC signal. Outliers were removed as above from both the FAM and VIC signal channels. The expression relative to control was calculated as above, using the VIC signal from the control gene.

Absolute Quantitation

Instead of calculating the expression relative to a reference marker, an absolute quantitation can be performed using real-time PCR. To determine the absolute quantity of each marker, a standard curve is constructed using serial dilutions from a known amount of template for each marker on the plate. The standard curve may be made using cloned genes purified from bacteria or using synthetic complimentary oligonucleotides. In either case, a dilution series that covers the expected range of expression is used as template in a series of wells in the plate. From the average $C_T$ values for these known amounts of template a standard curve can be plotted. From this curve the $C_T$ values for the unknowns are used to identify the starting concentration of cDNA. These absolute quantities can be compared between disease classes (i.e. rejection vs. no-rejection) or can be taken as expression relative to a control gene to correct for variation among samples in sample collection, RNA purification and quantification, cDNA synthesis, and the PCR amplification.

Cell Type Specific Expression

Some markers are expressed only in specific types of cells. These markers may be useful markers for differentiation of rejection samples from no-rejection samples or may be used to identify differential expression of other markers in a single cell type. A specific marker for cytotoxic T-lymphocytes (such as CD8) can be used to identify differences in cell proportions in the sample. Other markers that are known to be expressed in this cell type can be compared to the level of CD8 to indicate differential gene expression within CD8 T-cells.

Control Genes for PCR

As discussed above, PCR expression measurements can be made as either absolute quantification of gene expression using a standard curve or relative expression of a gene of interest compared to a control gene. In the latter case, the gene of interest and the control gene are measured in the same sample. This can be done in separate reactions or in the same reaction (biplex format, see above). In either case, the final measurement for expression of a gene is expressed as a ratio of gene expression to control gene expression. It is important for a control gene to be constitutively expressed in the target tissue of interest and have minimal variation in expression on a per cell basis between individuals or between samples derived from an individual. If the gene has this type of expression behavior, the relative expression ratio will help correct for variability in the amount of sample RNA used in an assay. In addition, an ideal control gene has a high level of expression in the sample of interest compared to the genes being assayed. This is important if the gene of interest and control gene are used in a biplex format. The assay is set up so that the control gene reaches its threshold Ct value early and its amplification is limited by primers so that it does not compete for limiting reagents with the gene of interest.

Figure 3A:
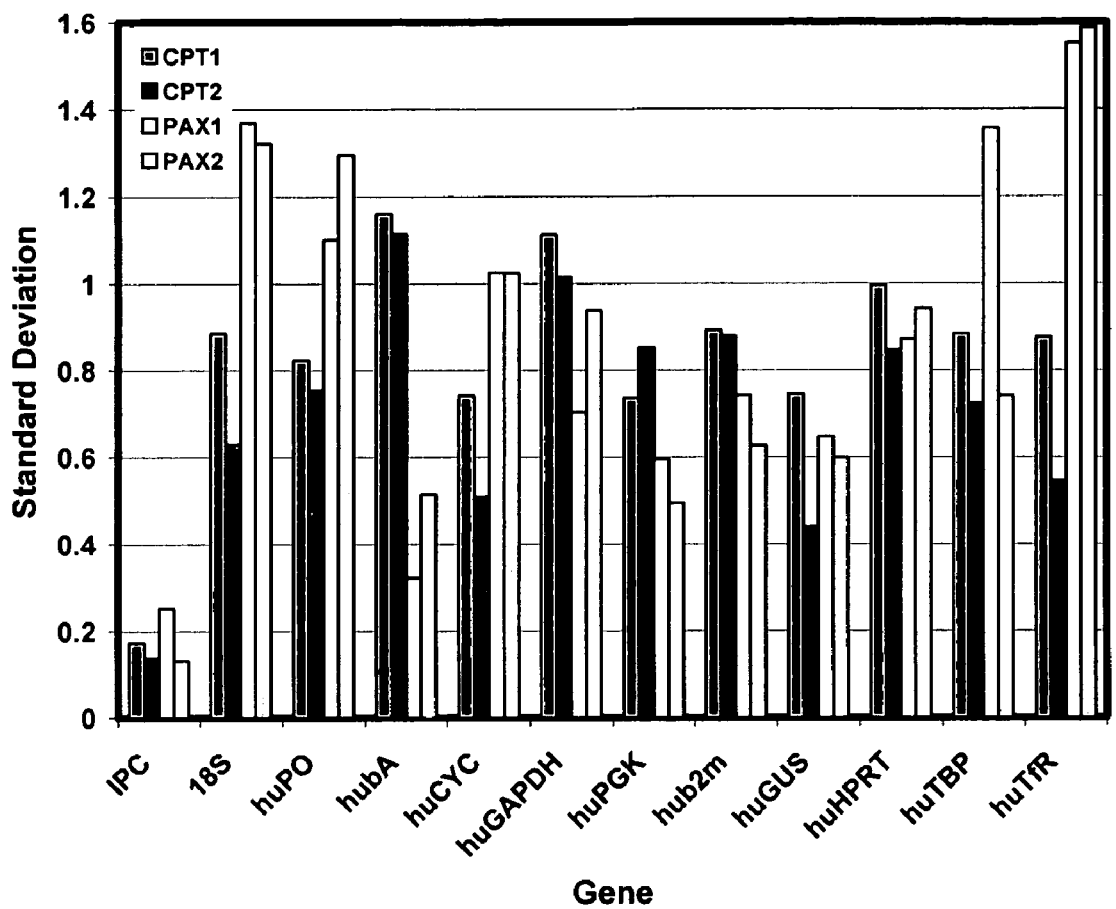
FIG. 3A shows the variation of control genes from PAX RNA (2 μg) and CPT RNA (0.5 μg).
Figure 3B:
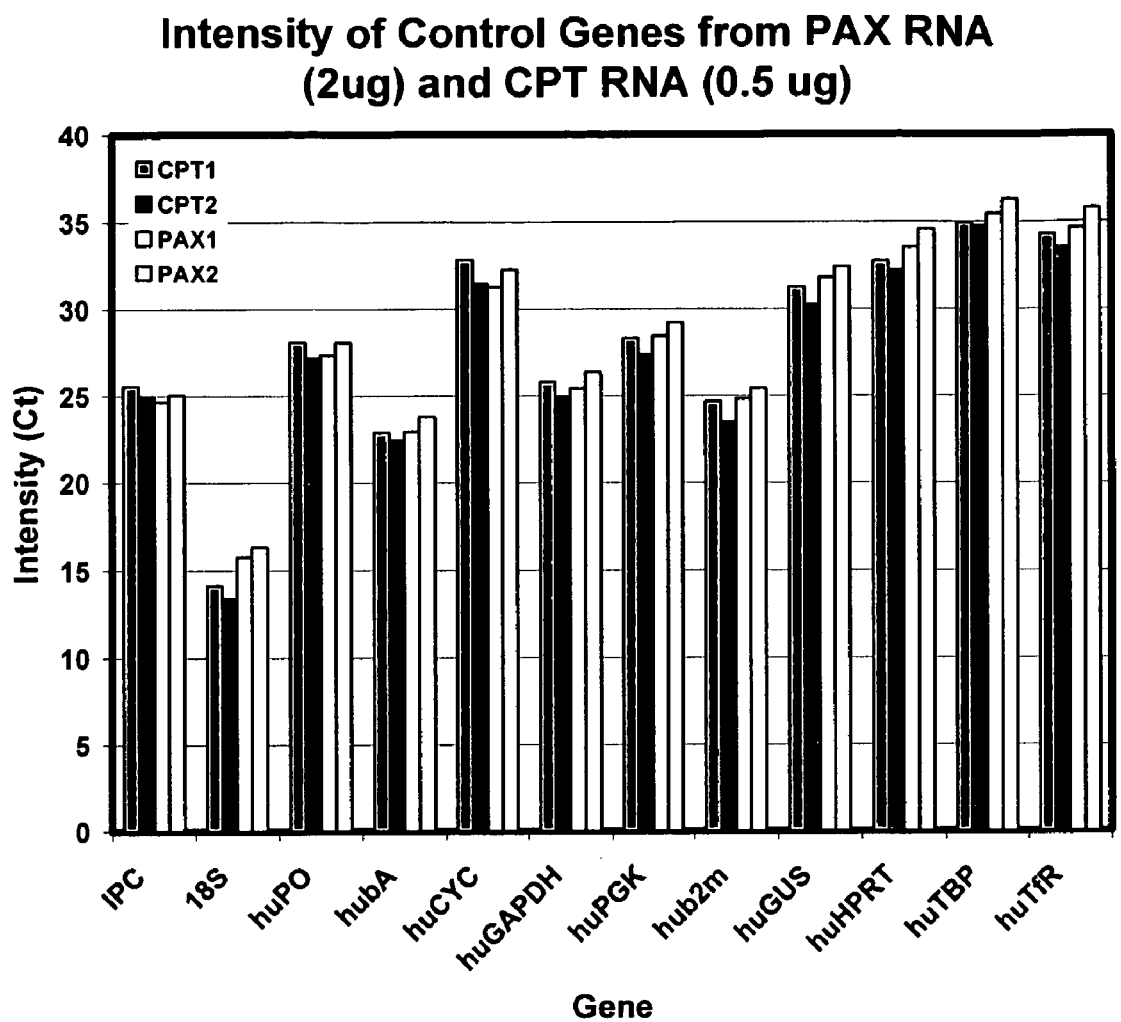
FIG. 3B shows the intensity of control genes from PAX RNA (2 μg) and CPT RNA (0.5 μg).

To identify an ideal control gene for an assay, a number of genes were tested for variability between samples and expression in both mononuclear RNA samples and whole blood RNA samples using the RNA procurement and preparation methods and real-time PCR assays described above. 6 whole-blood and 6 mononuclear RNA samples from transplant recipients were tested. The intensity levels and variability of each gene in duplicate experiments on both sample types are shown in FIG. 3.

Based on criteria of low variability and high expression across samples, β-actin, 18 s, GAPDH, b2 microglobulin were found to be good examples of control genes for the PAX samples. A single control gene may be incorporated as an internal biplex control is assays.

Controlling for Variation in Real Time PCR

Due to differences in reagents, experimenters, and preparation methods, and the variability of pipetting steps, there is significant plate-to-plate variation in real-time PCR experiments. This variation can be reduced by automation (to reduce variability and error), reagent lot quality control, and optimal data handling. However, the results on replicate plates are still likely to be different since they are run in the machine at different times.

Variation can also enter in data extraction and analysis. Real-time PCR results are measured as the time (measured in PCR cycles) at which the fluorescence intensity ($\Delta$Rn in Applied Biosystems SDS v2.1 software) crosses a user-determined threshold (CT). When performing relative quantification, the CT value for the target gene is subtracted from the CT value for a control gene. This difference, called $\Delta$CT, is the value compared among experiments to determine whether there is a difference between samples. Variation in setting the threshold can introduce additional error. This is especially true in the duplexed experimental format, where both the target gene and the control gene are measured in the same reaction tube. Duplexing is performed using dyes specific to each of the two genes. Since two different fluorescent dyes are used on the plate, two different thresholds are set. Both of these thresholds contribute to each $\Delta$CT. Slight differences in the each dye's threshold settings (relative to the other dye) from one plate to the next can have significant effects on the $\Delta$CT.

There are several methods for setting the threshold for a PCR plate. Older versions of SDS software (Applied Biosystems) determine the average baseline fluorescence for the plate and the standard deviation of the baseline. The threshold is set to 10× the standard deviation of the baseline. In SDS 2.0 the users must set the baseline by themselves. Software from other machine manufacturers either requires the user to set the threshold themselves or uses different algorithms. The latest version of the SDS software (SDS 2.1) contains Automatic baseline and threshold setting. The software sets the baseline separately for each well on the plate using the $\Delta$Rn at cycles preceding detectable levels.

Variability among plates is dependent on reproducible threshold setting. This requires a mathematical or experimental data driven threshold setting protocol. Reproducibly setting the threshold according to a standard formula will minimize variation that might be introduced in the threshold setting process.

Additionally, there may be experimental variation among plates that can be reduced by setting the threshold to a component of the data. We have developed a system that uses a set of reactions on each plate that are called the threshold calibrator (TCb). The TCb wells are used to set the threshold on all plates.

1. The TCb wells contain a template, primers, and probes that are common among all plates within an experiment.

2. The threshold is set within the minimum threshold and maximum threshold determined above.

3. The threshold is set to a value in this range that results in the average CT value for the TCb wells to be the same on all plates.

Example 5

Correlation and Classification Analysis

After generation and processing of expression data sets from microarrays, a log ratio value is used for most subsequent analysis. This is the logarithm of the expression ratio for each gene between sample and universal reference. The processing algorithm assigns a number of flags to data that are of low signal to noise, saturated signal or are in some other way of low or uncertain quality. Correlation analysis can proceed with all the data (including the flagged data) or can be done on filtered data sets where the flagged data is removed from the set. Filtered data should have less variability and noise and may result in more significant or predictive results. Flagged data contains all information available and may allow discovery of genes that are missed with the filtered data set.

After filtering the data for quality as described above, missing data are common in microarray data sets. Some algorithms don't require complete data sets and can thus tolerate missing values. Other algorithms are optimal with or require imputed values for missing data. Analysis of data sets with missing values can proceed by filtering all genes from the analysis that have more than 5%, 10%, 20%, 40%, 50%, 60% or other % of values missing across all samples in the analysis. Imputation of data for missing values can be done by a variety of methods such as using the row mean, the column mean, the nearest neighbor or some other calculated number. Except when noted, default settings for filtering and imputation were used to prepare the data for all analytical software packages.

In addition to expression data, clinical data are included in the analysis. Continuous variables, such as the ejection fraction of the heart measured by echocardiography or the white blood cell count can be used for correlation analysis. Any piece of clinical data collected on study subjects can be used in a correlation or classification analysis. In some cases, it may be desirable to take the logarithm of the values before analysis. These variables can be included in an analysis along with gene expression values, in which case they are treated as another "gene". Sets of markers can be discovered that work to diagnose a patient condition and these can include both genes and clinical parameters. Categorical variables such as male or female can also be used as variables for correlation analysis. For example, the sex of a patient may be an important splitter for a classification tree.

Clinical data are used as supervising vectors (dependent variables) for the significance or classification analysis of expression data. In this case, clinical data associated with the samples are used to divide samples in to clinically meaningful diagnostic categories for correlation or classification analysis. For example, pathologic specimens from kidney biopsies can be used to divide lupus patients into groups with and without kidney disease. A third or more categories can also be included (for example "unknown" or "not reported"). After generation of expression data and definition of supervising vectors, correlation, significance and classification analysis are used to determine which set of genes and set of genes are most appropriate for diagnosis and classification of patients and patient samples.

Two main types of expression data analyses are commonly performed on the expression data with differing results and purposes. The first is significance analyses or analyses of difference. In this case, the goal of the analysis is to identify genes that are differentially expressed between sample groups and to assign a statistical confidence to those genes that are identified. These genes may be markers of the disease process in question and are further studied and developed as diagnostic tools for the indication.

The second major type of analysis is classification analysis. While significance analysis identifies individual genes that are differentially expressed between sample groups, classification analysis identifies gene sets and an algorithm for their gene expression values that best distinguish sample (patient) groups. The resulting gene expression panel and algorithm can be used to create and implement a diagnostic test. The set of genes and the algorithm for their use as a diagnostic tool are often referred to herein as a "model". Individual markers can also be used to create a gene expression diagnostic model. However, multiple genes (or gene sets) are often more useful and accurate diagnostic tools.

Significance Analysis for Microarrays (SAM)

Significance analysis for microarrays (SAM) (Tusher 2001) is a method through which genes with a correlation between their expression values and the response vector are statistically discovered and assigned a statistical significance. The ratio of false significant to significant genes is the False Discovery Rate (FDR). This means that for each threshold there are some number of genes that are called significant, and the FDR gives a confidence level for this claim. If a gene is called differentially expressed between two classes by SAM, with a FDR of 5%, there is a 95% chance that the gene is actually differentially expressed between the classes. SAM will identify genes that are differentially expressed between the classes. The algorithm selects genes with low variance within a class and large variance between classes. The algorithm may not identify genes that are useful in classification, but are not differentially expressed in many of the samples. For example, a gene that is a useful marker for disease in women and not men, may not be a highly significant marker in a SAM analysis, but may be useful as part of a gene set for diagnosis of a multi-gene algorithm.

After generation of data from patient samples and definition of categories using clinical data as supervising vectors, SAM is used to detect genes that are likely to be differentially expressed between the groupings. Those genes with the highest significance can be validated by real-time PCR (Example 4) or can be used to build a classification algorithm as described here.

Classification

Classification algorithms are used to identify sets of genes and formulas for the expression levels of those genes that can be applied as diagnostic and disease monitoring tests. The same classification algorithms can be applied to all types of expression and proteomic data, including microarray and PCR based expression data. The discussion below describes the algorithms that were used and how they were used.

Classification and Regression Trees (CART) is a decision tree classification algorithm (Breiman 1984). From gene expression and or other data, CART can develop a decision tree for the classification of samples. Each node on the decision tree involves a query about the expression level of one or more genes or variables. Samples that are above the threshold go down one branch of the decision tree and samples that are not go down the other branch. Genes from expression data sets can be selected for classification building with CART by significant differential expression in SAM analysis (or other significance test), identification by supervised tree-harvesting analysis, high fold change between sample groups, or known relevance to classification of the target diseases. In addition, clinical data can be used as independent variables for CART that are of known importance to the clinical question or are found to be significant predictors by multivariate analysis or some other technique. CART identifies predictive variables and their associated decision rules for classification (diagnosis). CART also identifies surrogates for each splitter (genes that are the next best substitute for a useful gene in classification). Analysis is performed in CART by weighting misclassification costs to optimize desired performance of the assay. For example, it may be most important that the sensitivity of a test for a given diagnosis be >90%. CART models can be built and tested using 10 fold cross-validation or v-fold cross validation (see below). CART works best with a smaller number of variables (5-50).

Multiple Additive Regression Trees (Friedman, J H 1999, MART) is similar to CART in that it is a classification algorithm that builds decision trees to distinguish groups. MART builds numerous trees for any classification problem and the resulting model involves a combination of the multiple trees. MART can select variables as it build models and thus can be used on large data sets, such as those derived from an 8000 gene microarray. Because MART uses a combination of many trees and does not take too much information from any one tree, it resists over training. MART identifies a set of genes and an algorithm for their use as a classifier.

A Nearest Shrunken Centroids Classifier can be applied to microarray or other data sets by the methods described by Tibshirani et al. 2002. This algorithms also identified gene sets for classification and determines their 10 fold cross validation error rates for each class of samples. The algorithm determines the error rates for models of any size, from one gene to all genes in the set. The error rates for either or both sample classes can are minimized when a particular number of genes are used. When this gene number is determined, the algorithm associated with the selected genes can be identified and employed as a classifier on prospective sample.

For each classification algorithm and for significance analysis, gene sets and diagnostic algorithms that are built are tested by cross validation and prospective validation. Validation of the algorithm by these means yields an estimate of the predictive value of the algorithm on the target population. There are many approaches, including a 10 fold cross validation analysis in which 10% of the training samples are left out of the analysis and the classification algorithm is built with the remaining 90%. The 10% are then used as a test set for the algorithm. The process is repeated 10 times with 10% of the samples being left out as a test set each time. Through this analysis, one can derive a cross validation error which helps estimate the robustness of the algorithm for use on prospective (test) samples. Any % of the samples can be left out for cross validation (v-fold cross validation, LOOCV). When a gene set is established for a diagnosis with an acceptable cross validation error, this set of genes is tested using samples that were not included in the initial analysis (test samples). These samples may be taken from archives generated during the clinical study. Alternatively, a new prospective clinical study can be initiated, where samples are obtained and the gene set is used to predict patient diagnoses.

Example 6

Assay Sample Preparation

In order to show that leukocyte-specific markers can be detected in whole blood, we collected whole blood RNA using the PAXgene whole blood collection, stabilization, and RNA isolation kit (PreAnalytix). Varying amounts of the whole blood RNA were used in the initial RT reaction (1, 2, 4, and 8 ug), and varying dilutions of the different RT reactions were tested (1:5, 1:10, 1:20, 1:40, 1:80, 1:160). We did real-time PCR assays with primers specific to leukocyte markers and showed that we can reliably detect these markers in whole blood.

Total RNA was prepared from 14 mononuclear samples (CPT, BD) paired with 14 whole blood samples (PAXgene, PreAnalytix) from transplant recipients. cDNA was prepared from each sample using 2 ug total RNA as starting material. Resulting cDNA was diluted 1:10 and Sybr green real-time PCR assays were performed.

For real-time PCR assays, Ct values of 15-30 are desired for each gene. If a gene's Ct value is much above 30, the result may be variable and non-linear. For PAX

| Gene | Ct PAX | Ct CPT |
|---|---|---|
| CD20 | 27.41512 | 26.70474 |
| 4761 | 28.45656 | 26.52635 |
| 3096 | 29.09821 | 27.83281 |
| GranzymeB | 31.18779 | 30.56954 |
| IL4 | 33.11774 | 34.8002 |
| Actin | 19.17622 | 18.32966 |
| B-GUS | 26.89142 | 26.92735 | sample, target RNA will be more dilute than in CPT samples. cDNA dilutions must be appropriate to bring Ct values to less than 30. Ct values for the first 5 genes tested in this way are shown in the table below for both whole blood RNA (PAX) and mononuclear RNA (CPT).

With one exception, the genes have higher Ct values in whole blood. Using this protocol, all genes can be detected with Cts<35. For genes found to have Ct values above 30 in target samples, less diluted cDNA may be needed.

Example 7

Detection of Proteins Expressed by Diagnostic Gene Sequences

One of ordinary skill in the art is aware of many possible methods of protein detection. The following example illustrates one possible method.

The designated coding region of the sequence is amplified by PCR with adapter sequences at either end for subcloning. An epitope or other affinity "tag" such as a "His-tag" may be added to facilitate purification and/or detection of the protein. The amplified sequence is inserted into an appropriate expression vector, most typically a shuttle vector which can replicate in either bacteria, most typically *E. coli*, and the organism/cell of choice for expression such as a yeast or mammalian cell. Such shuttle vectors typically contain origins of replication for bacteria and an antibiotic resistance marker for selection in bacteria, as well as the relevant replication and selection sequences for transformation/transfection into the ultimate expression cell type. In addition, the sequence of interest is inserted into the vector so that the signals necessary for transcription (a promoter) and translation operably linked to the coding region. Said expression could be accomplished in bacteria, fungi, or mammalian cells, or by in vitro translation.

The expression vector would then typically be used to transform bacteria and clones analyzed to ensure that the proper sequence had been inserted into the expression vector in the productive orientation for expression. Said verified expression vector is then transfected into a host cell and transformants selected by a variety of methods including antibiotic resistance or nutritional complementation of an auxotrophic marker. Said transformed cells are then grown under conditions conducive to expression of the protein of interest, the cells and conditioned media harvested, and the protein of interest isolated from the most enriched source, either the cell pellet or media.

The protein is then be isolated by standard of chromatographic or other methods, including immunoaffinity chromatography using the affinity "tag" sequence or other methods, including cell fractionation, ion exchange, size exclusion chromatography, or selective precipitation. The isolated and purified protein is then be used as an antigen to generate specific antibodies. This is accomplished by standard methods including injection into heterologous species with an adjuvant, isolation of monoclonal antibodies from mice, or in vitro selection of antibodies from bacteriophage display antibody libraries. These antibodies are then used to detect the presence of the indicated protein of interest in a complex bodily fluid using standard methods such as ELISA or RIA.

Example 8

Efficacy of Transplant Rejection Drugs in Transplant Patients

FIGS. 1-3 illustrate that distinct molecular pathways are associated with differences in efficacy of tacrolimus and cyclosporin in cardiac transplant rejection.

We claim:

1. A method for determining the likelihood of a human patient to reject a cardiac transplant comprising detecting the level of a RNA that encodes SEQ ID NO: 24 in a blood sample from said patient and determining that said patient is likely to reject said cardiac transplant when the level of said RNA that encodes SEQ ID NO: 24 is increased relative to the mean level of said RNA that encodes SEQ ID NO: 24 in quiescent samples.

2. The method of claim 1 further comprising isolating said RNA from said patient prior to detecting.

3. The method of claim 2 wherein said RNA is detected by PCR.

4. The method of claim 2 wherein said RNA is detected by hybridization.

5. The method of claim 2 wherein said RNA is detected by hybridization to an oligonucleotide.

6. The method of claim 5 wherein said oligonucleotide comprises DNA, RNA, cDNA, PNA, genomic DNA, or synthetic oligonucleotides.

* * * * *

UNITED STATES PATENT AND TRADEMARK OFFICE
CERTIFICATE OF CORRECTION

PATENT NO. : 7,645,575 B2
APPLICATION NO. : 11/223492
DATED : January 12, 2010
INVENTOR(S) : Wohlgemuth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 51 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 41

<210> SEQ ID NO 1
<211> LENGTH: 20
<212> TYPE: DNA
<213> ORGANISM: Homo sapiens

<400> SEQUENCE: 1
ctcacaggag tggcaggtga                                           20

<210> SEQ ID NO 2
<211> LENGTH: 20
<212> TYPE: DNA
<213> ORGANISM: Homo sapiens

<400> SEQUENCE: 2
catagcacag cgcagagtgg                                           20

<210> SEQ ID NO 3
<211> LENGTH: 27
<212> TYPE: DNA
<213> ORGANISM: Homo sapiens

<400> SEQUENCE: 3
ccgactctcc agctgcaact gatacgg                                   27

<210> SEQ ID NO 4
<211> LENGTH: 99
<212> TYPE: DNA
<213> ORGANISM: Homo sapiens

<400> SEQUENCE: 4
ctcacaggag tggcaggtga ggacgagcta caggtgattc agcctgaaaa gtccgtatca    60
gttgcagctg gagagtcggc cactctgcgc tgtgctatg                           99

<210> SEQ ID NO 5
<211> LENGTH: 3804
<212> TYPE: DNA
<213> ORGANISM: Homo sapiens

<400> SEQUENCE: 5
cacagacgtt tggacagagc aggctcctaa ggtctccaga atgcccgtgc cagcctcctg    60
gccccacctt cctagtcctt tcctgctgat gacgctactg ctggggagac tcacaggagt   120
ggcaggtgag gacgagctac aggtgattca gcctgaaaag tccgtatcag ttgcagctgg   180
agagtcggcc actctgcgct gtgctatgac gtccctgatc cctgtggggc ccatcatgtg   240
```

-continued

```
gtttagagga gctggagcag gccgggaatt aatctacaat cagaaagaag gccacttccc    300
acgggtaaca actgtttcag aactcacaaa gagaaacaac ctgaactttt ccatcagcat    360
cagtaacatc accccagcag acgccggcac ctactactgt gtgaagttcc ggaaagggag    420
ccctgacgac gtggagttta gtctggagc aggcactgag ctgtctgtgc gcgccaaacc     480
ctctgccccc gtggtatcgg gccctgcggt gagggccaca cctgagcaca cagtgagctt    540
cacctgcgag tcccatggct tctctcccag agacatcacc ctgaaatggt tcaaaaatgg    600
gaatgagctc tcagacttcc agaccaacgt ggaccccgca ggagacagtg tgtcctacag    660
catccacagc acagccaggg tggtgctgac ccgtggggac gttcactctc aagtcatctg    720
cgagatggcc cacatcacct tgcagggggga ccctcttcgt gggactgcca acttgtctga   780
ggccatccga gttccaccca ccttggaggt tactcaacag cccatgaggg cagagaacca    840
ggcaaacgtc acctgccagg tgagcaattt ctaccccgg ggactacagc tgacctggtt     900
ggagaatgga aatgtgtccc ggacagaaac agcttcgacc ctcatagaga acaaggatgg    960
cacctacaac tggatgagct ggctcctggt gaacacctgt gcccacaggg acgatgtggt    1020
gctcacctgt caggtggagc atgatgggca gcaagcagtc agcaaaagct atgccctgga   1080
gatctcagca caccgaagg agcacggctc agatatcacc catgaaccag cgctggctcc    1140
tactgctcca ctcctcgtag ctcctcctcct gggccccaag ctgctactgg tggttggtgt   1200
ctctgccatc tacatctgct ggaaacagaa ggcctgactg accctcagtc tctgctgcct    1260
cctcctttct tgagaagctc agcctgagag aaggagctgg cgagaacctt ccccacactc    1320
agctccaaac gcctcctctc ccaggtcatc tgcctgccca cacgctcctg ttccaccttc    1380
acaagaccat gatgccccaa agcagtgtct ctattcacgg tcctgagcag gggccatggg    1440
attgggctct gggcactgac tcatggcacc tccctagaag gtgagaaaca ctccaaatct    1500
aaacacacca ggacttctcc catccgtcgc cttgggactg ccataaaacc acagactctc    1560
tccaggctct caagagttat cctgtcttct ggattcctgc ctaccccaac tcccccagcc    1620
ttgttgaggt tctctactgc ctcctgaata cacatgaacc cctataccaa ttttaagaaa    1680
aaaatgattc tctttcctct ttgtccaagc atcctatccc tcaaacccaa aaagaaagaa    1740
gctctccctt ctctctctgt gatggagaca gtatttcttc tagtatcctg cagccttccc    1800
agtcctgctg cttgtggtag aaattgctgc cacagcccaa cattgaggag ccctcgatga    1860
ctgccccttta caactcatat tcagttctgc ctccaaaatg catgtgtcca cttacatgag    1920
atggtaaatg tttaacaatg gactttctga aagggaaaaa ccaaaagctg ttttgcagtg    1980
cttgccaatt tctctagtgt aataactccc aacctgacca atttcagcac tgccaacagt    2040
taaacaacca gattcgaaga ttcctgaaat ttaacaattg gttttcaggg cccagtccaa    2100
gcctgctgct ggaaacctca gagttaaatc cctattctcc acacctctca cctccaccac    2160
ccctccctgt cccagccagc atcatctctt tggggaccac tcctctggct ttcattttc     2220
agccacagtg attctttgga aaagtcaaat catatcactt ctctgcttct tccccaacac    2280
agctgcatgg tcccgctctc cctccttcaa gtctctgctc aatgtcactt cattaaaggc    2340
ggccttctat aaactacctt gtataaaata ttatttattt tctctatccc ggcattctaa    2400
tttctcttat cctaattaat ttttctttag cccttatttt gatgagtatt atgccgaata    2460
caggcagccc tcacttttca tggccagtgc aagattgcaa aaagactgtg caacctgaaa    2520
cccaggaaag cagtctccat agtcaatcag aaaaacaatg atcattctgt gacctttacc    2580
```

```
attttttgtc aaaatattag aaactctcac actctcagtt acaaatgtag aggacaatga    2640
aaatataatg aaataaatat ttatttgtgc actacaattc aaagcattag aaacattgaa    2700
gtcaatggcg tttcttgtaa atgtatccag atgaggttgg aagagtgctt gacctttttg    2760
tatatttcta atatggagtg atatagtttg gctctgtgtc tccatccaaa tctcatctta    2820
aattgtaatc tgcatgtgtt gtgggaatgg gacctaggta ggaggtgact gaatacatgg    2880
gggcggactt cccccttgct gttcttgtga tagtgagttc tcataagatc tcagtgagtt    2940
ctcatgagat ctggtttttt gaaagtgtgt ggcaagtccc ccttcgctct ctctctctct    3000
ctccctcctg ccaccatgtg aagaaggtgc ctgcttcctt ttctccttcc accatggttg    3060
taagtttcct gaggcctccc agtcatgctt cctgttaagc ctgtggaact gtgagtccaa    3120
ttaaacctct tttattcata aaatatccag tttctggtag ttctttatag cagtgtgaga    3180
atgggctaat acacggagca agcatcgttc tttcattttt atttatttta ttttttgaga    3240
tggagtttca ccttattccc aggctggagt gcaatgtcgt gatcttggct cactgcaacc    3300
cccgcctcca gggttcaagt gattctcctg cctcagcctc ctgagtagct gggattacag    3360
gcatgtacca ccacacccag ctaattttgt attttagta gagatggggt ttctccatgt    3420
tgatcagact agtcttgaac tcccgacctc aggtgatcca cctgtcttgg cctcccaaag    3480
tgctgggatt acaggcatga gccaccatgc ctagccagca agcatcattt ctattatacc    3540
ttggtgtttg cctctttcta gtttggact agcttccaac atcttatccc ttgaattttc    3600
aatattgtgg aatcactcca gaagatcctt tcatgtgaag tttttgctg gcatttcaac    3660 ctttgggaca tcttcagccc ttttattacc actcctctcc catttgtggc agtttgcgtt    3720
tactacctcc ctctggctgc ctatctgaag ttcctgcatc agggtctaca ttgccacagt    3780
caactatttg tacttctaga attc                                          3804
```

<210> SEQ ID NO 6
<211> LENGTH: 398
<212> TYPE: PRT
<213> ORGANISM: Homo sapiens

<400> SEQUENCE: 6

```
Met Pro Val Pro Ala Ser Trp Pro His Leu Pro Ser Pro Phe Leu Leu
 1               5                  10                  15

Met Thr Leu Leu Leu Gly Arg Leu Thr Gly Val Ala Gly Glu Asp Glu
                20                  25                  30

Leu Gln Val Ile Gln Pro Glu Lys Ser Val Ser Val Ala Ala Gly Glu
            35                  40                  45

Ser Ala Thr Leu Arg Cys Ala Met Thr Ser Leu Ile Pro Val Gly Pro
        50                  55                  60

Ile Met Trp Phe Arg Gly Ala Gly Ala Gly Arg Glu Leu Ile Tyr Asn
65                  70                  75                  80

Gln Lys Glu Gly His Phe Pro Arg Val Thr Thr Val Ser Glu Leu Thr
                85                  90                  95

Lys Arg Asn Asn Leu Asn Phe Ser Ile Ser Ile Ser Asn Ile Thr Pro
            100                 105                 110

Ala Asp Ala Gly Thr Tyr Tyr Cys Val Lys Phe Arg Lys Gly Ser Pro
        115                 120                 125

Asp Asp Val Glu Phe Lys Ser Gly Ala Gly Thr Glu Leu Ser Val Arg
    130                 135                 140

Ala Lys Pro Ser Ala Pro Val Val Ser Gly Pro Ala Val Arg Ala Thr
145                 150                 155                 160
```

```
Pro Glu His Thr Val Ser Phe Thr Cys Glu Ser His Gly Phe Ser Pro
            165                 170                 175

Arg Asp Ile Thr Leu Lys Trp Phe Lys Asn Gly Asn Glu Leu Ser Asp
            180                 185                 190

Phe Gln Thr Asn Val Asp Pro Ala Gly Asp Ser Val Ser Tyr Ser Ile
            195                 200                 205

His Ser Thr Ala Arg Val Val Leu Thr Arg Gly Asp Val His Ser Gln
            210                 215                 220

Val Ile Cys Glu Met Ala His Ile Thr Leu Gln Gly Asp Pro Leu Arg
225                 230                 235                 240

Gly Thr Ala Asn Leu Ser Glu Ala Ile Arg Val Pro Pro Thr Leu Glu
            245                 250                 255

Val Thr Gln Gln Pro Met Arg Ala Glu Asn Gln Ala Asn Val Thr Cys
            260                 265                 270

Gln Val Ser Asn Phe Tyr Pro Arg Gly Leu Gln Leu Thr Trp Leu Glu
            275                 280                 285

Asn Gly Asn Val Ser Arg Thr Glu Thr Ala Ser Thr Leu Ile Glu Asn
290                 295                 300

Lys Asp Gly Thr Tyr Asn Trp Met Ser Trp Leu Leu Val Asn Thr Cys
305                 310                 315                 320

Ala His Arg Asp Asp Val Val Leu Thr Cys Gln Val Glu His Asp Gly
            325                 330                 335

Gln Gln Ala Val Ser Lys Ser Tyr Ala Leu Glu Ile Ser Ala His Gln
            340                 345                 350

Lys Glu His Gly Ser Asp Ile Thr His Glu Pro Ala Leu Ala Pro Thr
            355                 360                 365

Ala Pro Leu Leu Val Ala Leu Leu Gly Pro Lys Leu Leu Leu Val
            370                 375                 380

Val Gly Val Ser Ala Ile Tyr Ile Cys Trp Lys Gln Lys Ala
385                 390                 395

<210> SEQ ID NO 7
<211> LENGTH: 20
<212> TYPE: DNA
<213> ORGANISM: Homo sapiens

<400> SEQUENCE: 7
acccagacac cctgaaccag                                           20

<210> SEQ ID NO 8
<211> LENGTH: 20
<212> TYPE: DNA
<213> ORGANISM: Homo sapiens

<400> SEQUENCE: 8
tgtgtccagg tcctccatga                                           20

<210> SEQ ID NO 9
<211> LENGTH: 24
<212> TYPE: DNA
<213> ORGANISM: Homo sapiens

<400> SEQUENCE: 9
tcgcaccagc tctttgaatt cccc                                      24

<210> SEQ ID NO 10
<211> LENGTH: 122
```

```
<212> TYPE: DNA
<213> ORGANISM: Homo sapiens

<400> SEQUENCE: 10
acccagacac cctgaaccag ggggaattca aagagctggt gcgaaaagat ctgcaaaatt      60
ttctcaagaa ggagaataag aatgaaaagg tcatagaaca catcatggag gacctggaca     120
ca                                                                    122

<210> SEQ ID NO 11
<211> LENGTH: 576
<212> TYPE: DNA
<213> ORGANISM: Homo sapiens

<400> SEQUENCE: 11
aaacactctg tgtggctcct cggctttggg acagagtgca agacgatgac ttgcaaaatg      60
tcgcagctgg aacgcaacat agagaccatc atcaacacct tccaccaata ctctgtgaag     120
ctggggcacc cagacaccct gaaccagggg gaattcaaag agctggtgcg aaaagatctg     180
caaaattttc tcaagaagga gaataagaat gaaaaggtca tagaacacat catggaggac     240
ctggacacaa atgcagacaa gcagctgagc ttcgaggagt tcatcatgct gatggcgagg     300
ctaacctggg cctcccacga aagatgcac gagggtgacg agggccctgg ccaccaccat     360
aagccaggcc tcggggaggg cacccccta gaccacagtg ccaagatca cagtggccac     420 ggccatggcc acagtcatgg tggccacggc cacaggccac taatcaggag gccaggccac     480
cctgcctcta cccaaccagg gccccgggc ctgttatgtc aaactgtctt ggctgtgggg     540 ctagggggctg gggccaaata aagtctcttc ctccaa                             576

<210> SEQ ID NO 12
<211> LENGTH: 114
<212> TYPE: PRT
<213> ORGANISM: Homo sapiens

<400> SEQUENCE: 12

Met Thr Cys Lys Met Ser Gln Leu Glu Arg Asn Ile Glu Thr Ile Ile
 1               5                  10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
        50                  55                  60

Asp Leu Asp Thr Asn Ala Asp Lys Gln Leu Ser Phe Glu Glu Phe Ile
 65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
                100                 105                 110

Thr Pro

<210> SEQ ID NO 13
<211> LENGTH: 20
<212> TYPE: DNA
<213> ORGANISM: Homo sapiens

<400> SEQUENCE: 13
ttggttgggg aaagtcgtgt                                                  20
```

<210> SEQ ID NO 14
<211> LENGTH: 20
<212> TYPE: DNA
<213> ORGANISM: Homo sapiens

<400> SEQUENCE: 14
ctccgcaaag ccagtgaatc                                                  20

<210> SEQ ID NO 15
<211> LENGTH: 20
<212> TYPE: DNA
<213> ORGANISM: Homo sapiens

<400> SEQUENCE: 15
agcccggcgt ctccctccac                                                  20

<210> SEQ ID NO 16
<211> LENGTH: 98
<212> TYPE: DNA
<213> ORGANISM: Homo sapiens

<400> SEQUENCE: 16
ttggttgggg aaagtcgtgt ctgtcagact gccctgggtg gagggagacg ccgggctaga      60
gcctttggga tcgtcctgga ttcactggct ttgcggag                              98

<210> SEQ ID NO 17
<211> LENGTH: 3962
<212> TYPE: DNA
<213> ORGANISM: Homo sapiens

<400> SEQUENCE: 17
gaattccggc gtcgcggacg catcccagtc tgggcgggac gctcggccgc ggcgaggcgg      60
gcaagcctgg cagggcagag ggagccccgg ctccgaggtt gctcttcgcc cccgaggatc     120
agtcttggcc ccaaagcgcg acgcacaaat ccacataacc tgaggaccat ggatgctgat     180
gagggtcaag acatgtccca gtttcaggg aaggaaagcc ccctgtaag cgatactcca      240 gatgagggcg atgagcccat gccgatcccc gaggacctct ccaccacctc gggaggacag     300
caaagctcca gagtgacag agtcgtggcc agtaatgtta aagtagagac tcagagtgat     360
gaagagaatg ggcgtgcctg tgaaatgaat ggggaagaat gtgcggagga tttacgaatg     420
cttgatgcct cgggagagaa aatgaatggc tcccacaggg accaaggcag ctcggctttg     480
tcgggagttg gaggcattcg acttcctaac ggaaaactaa agtgtgatat ctgtgggatc     540
atttgcatcg ggcccaatgt gctcatggtt cacaaaagaa gccacactgg agaacggccc     600
ttccagtgca atcagtgcgg ggcctcattc acccagaagg gcaacctgct ccggcacatc     660
aagctgcatt ccggggagaa gcccttcaaa tgccacctct gcaactacgc ctgccgccgg     720
agggacgccc tcactggcca cctgaggacg cactccgttg gtaaacctca caaatgtgga     780
tattgtggcc gaagctataa acagcgaagc tctttagagg aacataaaga gcgctgccac     840
aactacttgg aaagcatggg ccttccgggc acactgtacc cagtcattaa agaagaaact     900
aatcacagtg aaatggcaga agacctgtgc aagataggat cagagagatc tctcgtgctg     960
gacagactag caagtaacgt cgccaaacgt aagagctcta tgcctcagaa atttcttggg    1020
gacaagggcc tgtccgacac gccctacgac agcagcgcca gctacgagaa ggagaacgaa    1080
atgatgaagt cccacgtgat ggaccaagcc atcaacaacg ccatcaacta cctgggggcc    1140

-continued

```
gagtccctgc gcccgctggt gcagacgccc ccgggcggtt ccgaggtggt cccggtcatc    1200
agcccgatgt accagctgca caagccgctc gcggagggca ccccgcgctc caaccactcg    1260
gcccaggaca cgccgtggaa gaacctgctg ctgctctcca aggccaagtt ggtgccctcg    1320
gagcgcgagg cgtccccgag caacagctgc caagactcca cggacaccga gagcaacaac    1380
gaggagcagc gcagcggtct catctacctg accaaccaca tcgccccgca cgcgcgcaac    1440
gggctgtcgc tcaaggagga gcaccgcgcc tacgacctgc tgcgcgccgc ctccgagaac    1500
tcgcaggacg cgctccgcgt ggtcagcacc agcggggagc agatgaaggt gtacaagtgc    1560
gaacactgcc gggtgctctt cctggatcac gtcatgtaca ccatccacat gggctgccac    1620
ggcttccgtg atccttttga gtgcaacatg tgcggctacc acagccagga ccggtacgag    1680
ttctcgtcgc acataacgcg aggggagcac cgcttccaca tgagctaaag ccctcccgcg    1740
ccccaccccc agaccccgag ccaccccagg aaaagcacaa ggactgccgc cttctcgctc    1800
ccgccagcag catagactgg actggaccag acaatgttgt gtttggattt gtaactgttt    1860
tttgtttttt gtttgagttg gttgattggg gtttgatttg cttttgaaaa gattttt att    1920 tttagaggca gggctgcatt gggagcatcc agaactgcta ccttcctaga tgtttcccca    1980
gaccgctggc tgagattccc tcacctgtcg cttcctagaa tccccttctc caaacgatta    2040
gtctaaattt tcagagagaa atagataaaa cacgccacag cctgggaagg agcgtgctct    2100
accctgtgct aagcacgggg ttcgcgcacc aggtgtcttt ttccagtccc cagaagcaga    2160
gagcacagcc cctgctgtgt gggtctgcag gtgagcagac aggacaggtg tgccgccacc    2220
caagtgccaa gacacagcag ggccaacaac ctgtgcccag gccagcttcg agctacatgc    2280
atctagggcg gagaggctgc acttgtgaga gaaaatacta tttcaagtca tattctgcgt    2340
aggaaaatga attggttggg gaaagtcgtg tctgtcagac tgccctgggt ggagggagac    2400
gccgggctag agcctttggg atcgtcctgg attcactggc tttgcggagg ctgctcagat    2460
ggcctgagcc tcccgaggct tgctgccccg taggaggaga ctgtcttccc gtgggcatat    2520
ctggggagcc ctgttccccg cttttttcact cccatacctt taatggcccc caaaatctgt    2580
cactacaatt taaacaccag tcccgaaatt tggatcttct ttcttttga atctctcaaa     2640 cggcaacatt cctcagaaac caaagcttta tttcaaatct cttccttccc tggctggttc    2700
catctagtac cagaggcctc ttttcctgaa gaaatccaat cctagccctc attttaatta    2760
tgtacatctg tttgtagcca caagcctgaa tttctcagtg ttggtaagtt tcttaccta    2820 ccctcactat atattattct cgttttaaaa cccataaagg agtgatttag aacagtcatt    2880
aattttcaac tcaatgaaat atgtgaagcc cagcatctct gttgctaaca cacagagctc    2940
acctgtttga aaccaagctt tcaaacatgt tgaagctctt tactgtaaag gcaagccagc    3000
atgtgtgtcc acacatacat aggatggctg gctctgcacc tgtaggatat tggaatgcac    3060
agggcaattg agggactgag ccagaccttc ggagagtaat gccaccagat cccctaggaa    3120
agaggaggca aatggcactg caggtgagaa ccccgcccat ccgtgctatg acatggaggc    3180
actgaagccc gaggaaggtg tgtggagatt ctaatcccaa caagcaaggg tctccttcaa    3240
gattaatgct atcaatcatt aaggtcatta ctctcaacca cctaggcaat gaagaatata    3300
ccatttcaaa tatttacagt acttgtcttc accaacactg tcccaaggtg aaatgaagca    3360
acagagagga aattgtacat aagtacctca gcatttaatc caaacagggg ttcttagtct    3420
cagcactatg acatttttggg ctgactactt atttgttagg cggagctct cctgtgcatt    3480 gtaggataat tagcagtatc cctggtggct acccaataga cgccagtagc acccccgaatt    3540
```

```
gacaacccaa actctccaga catcaccaac tgtcccctgc gaggagaaat cactcctggg    3600
ggagaaccac tgacccaaat gaattctaaa ccaatcaaat gtctgggaag ccctccaaga    3660
aaaaaaatag aaaagcactt gaagaatatt cccaatattc ccggtcagca gtatcaaggc    3720
tgacttgtgt tcatgtggag tcattataaa ttctataaat caattattcc ccttcggtct    3780
taaaaatata tttcctcata aacatttgag ttttgttgaa aagatggagt ttacaaagat    3840
accattcttg agtcatggat ttctctgctc acagaagggt gtggcatttg gaaacgggaa    3900
taaacaaaat tgctgcacca atgcactgag tgaaggaaga gagacagagg atcaagggct    3960
tt                                                                  3962
```

<210> SEQ ID NO 18
<211> LENGTH: 519
<212> TYPE: PRT
<213> ORGANISM: Homo sapiens

<400> SEQUENCE: 18

```
Met Asp Ala Asp Glu Gly Gln Asp Met Ser Gln Val Ser Gly Lys Glu
1               5                   10                  15

Ser Pro Pro Val Ser Asp Thr Pro Asp Glu Gly Asp Glu Pro Met Pro
            20                  25                  30

Ile Pro Glu Asp Leu Ser Thr Thr Ser Gly Gly Gln Gln Ser Ser Lys
        35                  40                  45

Ser Asp Arg Val Val Ala Ser Asn Val Lys Val Glu Thr Gln Ser Asp
    50                  55                  60

Glu Glu Asn Gly Arg Ala Cys Glu Met Asn Gly Glu Glu Cys Ala Glu
65                  70                  75                  80

Asp Leu Arg Met Leu Asp Ala Ser Gly Glu Lys Met Asn Gly Ser His
                85                  90                  95

Arg Asp Gln Gly Ser Ser Ala Leu Ser Gly Val Gly Gly Ile Arg Leu
            100                 105                 110

Pro Asn Gly Lys Leu Lys Cys Asp Ile Cys Gly Ile Ile Cys Ile Gly
        115                 120                 125

Pro Asn Val Leu Met Val His Lys Arg Ser His Thr Gly Glu Arg Pro
    130                 135                 140

Phe Gln Cys Asn Gln Cys Gly Ala Ser Phe Thr Gln Lys Gly Asn Leu
145                 150                 155                 160

Leu Arg His Ile Lys Leu His Ser Gly Glu Lys Pro Phe Lys Cys His
                165                 170                 175

Leu Cys Asn Tyr Ala Cys Arg Arg Arg Asp Ala Leu Thr Gly His Leu
            180                 185                 190

Arg Thr His Ser Val Gly Lys Pro His Lys Cys Gly Tyr Cys Gly Arg
        195                 200                 205

Ser Tyr Lys Gln Arg Ser Ser Leu Glu Glu His Lys Glu Arg Cys His
    210                 215                 220

Asn Tyr Leu Glu Ser Met Gly Leu Pro Gly Thr Leu Tyr Pro Val Ile
225                 230                 235                 240

Lys Glu Glu Thr Asn His Ser Glu Met Ala Glu Asp Leu Cys Lys Ile
                245                 250                 255

Gly Ser Glu Arg Ser Leu Val Leu Asp Arg Leu Ala Ser Asn Val Ala
            260                 265                 270

Lys Arg Lys Ser Ser Met Pro Gln Lys Phe Leu Gly Asp Lys Gly Leu
        275                 280                 285
```

-continued

```
Ser Asp Thr Pro Tyr Asp Ser Ser Ala Ser Tyr Glu Lys Glu Asn Glu
    290                 295                 300

Met Met Lys Ser His Val Met Asp Gln Ala Ile Asn Asn Ala Ile Asn
305                 310                 315                 320

Tyr Leu Gly Ala Glu Ser Leu Arg Pro Leu Val Gln Thr Pro Pro Gly
                325                 330                 335

Gly Ser Glu Val Val Pro Val Ile Ser Pro Met Tyr Gln Leu His Lys
            340                 345                 350

Pro Leu Ala Glu Gly Thr Pro Arg Ser Asn His Ser Ala Gln Asp Ser
        355                 360                 365

Ala Val Glu Asn Leu Leu Leu Ser Lys Ala Lys Leu Val Pro Ser
370                 375                 380

Glu Arg Glu Ala Ser Pro Ser Asn Ser Cys Gln Asp Ser Thr Asp Thr
385                 390                 395                 400

Glu Ser Asn Asn Glu Glu Gln Arg Ser Gly Leu Ile Tyr Leu Thr Asn
                405                 410                 415

His Ile Ala Pro His Ala Arg Asn Gly Leu Ser Leu Lys Glu Glu His
            420                 425                 430

Arg Ala Tyr Asp Leu Leu Arg Ala Ala Ser Glu Asn Ser Gln Asp Ala
        435                 440                 445

Leu Arg Val Val Ser Thr Ser Gly Glu Gln Met Lys Val Tyr Lys Cys
    450                 455                 460

Glu His Cys Arg Val Leu Phe Leu Asp His Val Met Tyr Thr Ile His
465                 470                 475                 480

Met Gly Cys His Gly Phe Arg Asp Pro Phe Glu Cys Asn Met Cys Gly
                485                 490                 495

Tyr His Ser Gln Asp Arg Tyr Glu Phe Ser Ser His Ile Thr Arg Gly
            500                 505                 510

Glu His Arg Phe His Met Ser
        515

<210> SEQ ID NO 19
<211> LENGTH: 20
<212> TYPE: DNA
<213> ORGANISM: Homo sapiens

<400> SEQUENCE: 19
cagctgtggt cccactcgta                                          20

<210> SEQ ID NO 20
<211> LENGTH: 21
<212> TYPE: DNA
<213> ORGANISM: Homo sapiens

<400> SEQUENCE: 20
gtcaggatag caggcatctg g                                        21

<210> SEQ ID NO 21
<211> LENGTH: 26
<212> TYPE: DNA
<213> ORGANISM: Homo sapiens

<400> SEQUENCE: 21
tttccaccat tttggtctca ccacca                                   26

<210> SEQ ID NO 22
<211> LENGTH: 80
<212> TYPE: DNA
```

<213> ORGANISM: Homo sapiens

<400> SEQUENCE: 22

```
cagctgtggt cccactcgta tatggtggtg agaccaaaat ggtggaaaca gccttaaccc    60
cagatgcctg ctatcctgac                                                80
```

<210> SEQ ID NO 23
<211> LENGTH: 948
<212> TYPE: DNA
<213> ORGANISM: Homo sapiens

<400> SEQUENCE: 23

```
cacacacctt aaccctgact tttttgctc cagtttttca gaagaagtga agtcaagatg    60
aagaaccatt tgcttttctg gggagtcctg gcggttttta ttaaggctgt tcatgtgaaa   120
gcccaagaag atgaaaggat tgttcttgtt gacaacaaat gtaagtgtgc ccggattact   180
tccaggatca tccgttcttc cgaagatcct aatgaggaca ttgtggagag aaacatccga   240
attattgttc ctctgaacaa cagggagaat atctctgatc ccacctcacc attgagaacc   300
agatttgtgt accatttgtc tgacctctgt aaaaaatgtg atcctacaga agtggagctg   360
gataatcaga tagttactgc tacccagagc aatatctgtg atgaagacag tgctacagag   420
acctgctaca cttatgacag aaacaagtgc tacacagctg tggtcccact cgtatatggt   480
ggtgagacca aaatggtgga acagccttaa ccccagatgc ctgctatcc tgactaattt   540
aagtcattgc tgactgcata gctcttttc ttgagaggct ctccattttg attcagaaag   600
ttagcatatt tattaccaat gaatttgaaa ccagggcttt ttttttttt ttgggtgatg   660
taaaccaac tccctgccac caaaataatt aaaatagtca cattgttatc tttattaggt   720
aatcacttct taattatatg ttcatactct aagtatcaaa atcttccaat tatcatgctc   780
acctgaaaga ggtatgctct cttaggaata cagtttctag cattaaacaa ataaacaagg   840
ggagaaaata aaactcaagg agtgaaaatc aggaggtgta ataaaatgtt cctcgcattc   900
aaaaaaaaaa aaaaaaaaaa aaaaaaaaaa aaaaaaaaaa aaaaaaaa                 948
```

<210> SEQ ID NO 24
<211> LENGTH: 159
<212> TYPE: PRT
<213> ORGANISM: Homo sapiens

<400> SEQUENCE: 24

```
Met Lys Asn His Leu Leu Phe Trp Gly Val Leu Ala Val Phe Ile Lys
 1               5                  10                  15

Ala Val His Val Lys Ala Gln Glu Asp Glu Arg Ile Val Leu Val Asp
            20                  25                  30

Asn Lys Cys Lys Cys Ala Arg Ile Thr Ser Arg Ile Ile Arg Ser Ser
        35                  40                  45

Glu Asp Pro Asn Glu Asp Ile Val Glu Arg Asn Ile Arg Ile Ile Val
    50                  55                  60

Pro Leu Asn Asn Arg Glu Asn Ile Ser Asp Pro Thr Ser Pro Leu Arg
65                  70                  75                  80

Thr Arg Phe Val Tyr His Leu Ser Asp Leu Cys Lys Lys Cys Asp Pro
                85                  90                  95

Thr Glu Val Glu Leu Asp Asn Gln Ile Val Thr Ala Thr Gln Ser Asn
            100                 105                 110

Ile Cys Asp Glu Asp Ser Ala Thr Glu Thr Cys Tyr Thr Tyr Asp Arg
        115                 120                 125
```

Asn Lys Cys Tyr Thr Ala Val Val Pro Leu Val Tyr Gly Gly Glu Thr
    130                 135                 140

Lys Met Val Glu Thr Ala Leu Thr Pro Asp Ala Cys Tyr Pro Asp
145                 150                 155

<210> SEQ ID NO 25
<211> LENGTH: 463
<212> TYPE: DNA
<213> ORGANISM: Homo sapiens

<400> SEQUENCE: 25

```
ttggcttgac tcaggattta aaaactggaa cggtgaaggt gacagcagtc ggttggacga      60
gcatccccca aagttcacaa tgtggccgag gactttgatt gcacattgtt gttttttaat     120
agtcattcca aatatgagat gcattgttac aggaagtccc ttgccatcct aaaagcaccc     180
cacttctctc taaggagaat ggcccagtcc tctcccaagt ccacacaggg gagggatagc     240
attgctttcg tgtaaattat gtaatgcaaa attttttaa tcttcgcctt aatcttttt     300
attttgtttt atttgaatg atgagccttc gtgcccccc ttccccttt tttccccaa     360
cttgagatgt atgaaggctt tggtctccc tgggagtggg tggaggcagc cgggcttacc      420
tgtacactga cttgagacca gttgaataaa agtgcacacc tta                       463
```

<210> SEQ ID NO 26
<211> LENGTH: 491
<212> TYPE: DNA
<213> ORGANISM: Homo sapiens

<400> SEQUENCE: 26

```
gaagagtacc agaaaagtct gctagagcag taccatctgg gtctggatca aaaacgcaga      60
aaatatgtgg ttggagagct catttggaat tttgccgatt tcatgactga acagtcaccg     120
acgagagtgc tggggaataa aaagggatc ttcactcggc agagacaacc aaaaagtgca     180
gcgttccttt tgcgagagag atactggaag attgccaatg aaaccaggta tccccactca     240
gtagccaagt cacaatgttt ggaaaacagc ccgtttactt gagcaagact gataccacct     300
gcgtgtccct tcctccccga gtcagggcga cttccacagc agcagaacaa gtgcctcctg     360
gactgttcac ggcagaccag aacgtttctg gcctgggttt gtgtggtcatc tattctagca    420
gggaacacta aaggtggaaa taaagatttt ctattatgg aaataaagag ttggcatgaa     480
agtcgctact g                                                          491
```

<210> SEQ ID NO 27
<211> LENGTH: 20
<212> TYPE: DNA
<213> ORGANISM: Homo sapiens

<400> SEQUENCE: 27

```
cacaatgtgg ccgaggactt                                                  20
```

<210> SEQ ID NO 28
<211> LENGTH: 20
<212> TYPE: DNA
<213> ORGANISM: Homo sapiens

<400> SEQUENCE: 28

```
tgtggccgag gactttgatt                                                  20
```

<210> SEQ ID NO 29

```
<211> LENGTH: 20
<212> TYPE: DNA
<213> ORGANISM: Homo sapiens

<400> SEQUENCE: 29
tggcttttag gatggcaagg                                               20

<210> SEQ ID NO 30
<211> LENGTH: 20
<212> TYPE: DNA
<213> ORGANISM: Homo sapiens

<400> SEQUENCE: 30
gggggcttag tttgcttcct                                               20

<210> SEQ ID NO 31
<211> LENGTH: 20
<212> TYPE: DNA
<213> ORGANISM: Homo sapiens

<400> SEQUENCE: 31
aagtgcagcg ttccttttgc                                               20

<210> SEQ ID NO 32
<211> LENGTH: 20
<212> TYPE: DNA
<213> ORGANISM: Homo sapiens

<400> SEQUENCE: 32
agcgttcctt ttgcgagaga                                               20

<210> SEQ ID NO 33
<211> LENGTH: 20
<212> TYPE: DNA
<213> ORGANISM: Homo sapiens

<400> SEQUENCE: 33
cgggctgttt tccaaacatt                                               20

<210> SEQ ID NO 34
<211> LENGTH: 20
<212> TYPE: DNA
<213> ORGANISM: Homo sapiens

<400> SEQUENCE: 34
gaagggacac gcaggtggta                                               20

<210> SEQ ID NO 35
<211> LENGTH: 20
<212> TYPE: DNA
<213> ORGANISM: Homo sapiens

<400> SEQUENCE: 35
taccacctgc gtgtcccttc                                               20

<210> SEQ ID NO 36
<211> LENGTH: 21
<212> TYPE: DNA
<213> ORGANISM: Homo sapiens

<400> SEQUENCE: 36
gaggcacttg ttctgctgct g                                             21
```

```
<210> SEQ ID NO 37
<211> LENGTH: 327
<212> TYPE: DNA
<213> ORGANISM: Homo sapiens

<400> SEQUENCE: 37
ggggactctg gaggccctct tgtgtgtaac aaggtggccc agggcattgt ctcctatgga    60
cgaaacaatg gcatgcctcc acgagcctgc accaaagtct caagctttgt acactggata   120
aagaaaacca tgaaacgcta ctaactacag gaagcaaact aagccccccgc tgtaatgaaa   180 caccttctct ggagccaagt ccagatttac actgggagag gtgccagcaa ctgaataaat   240
acctctccca gtgtaaatct ggagccaagt ccagatttac actgggagag gtgccagcaa   300
ctgaataaat acctcttagc tgagtgg                                        327

<210> SEQ ID NO 38
<211> LENGTH: 20
<212> TYPE: DNA
<213> ORGANISM: Homo sapiens

<400> SEQUENCE: 38
acgagcctgc accaaagtct                                                 20

<210> SEQ ID NO 39
<211> LENGTH: 20
<212> TYPE: DNA
<213> ORGANISM: Homo sapiens

<400> SEQUENCE: 39
aaacaatggc atgcctccac                                                 20

<210> SEQ ID NO 40
<211> LENGTH: 20
<212> TYPE: DNA
<213> ORGANISM: Homo sapiens

<400> SEQUENCE: 40
tcattacagc gggggcttag                                                 20

<210> SEQ ID NO 41
<211> LENGTH: 20
<212> TYPE: DNA
<213> ORGANISM: Homo sapiens

<400> SEQUENCE: 41
gggggcttag tttgcttcct                                                 20
```